United States Patent
Surleraux et al.

(10) Patent No.: US 7,659,404 B2
(45) Date of Patent: Feb. 9, 2010

(54) BROAD SPECTRUM 2-(SUBSTITUTED-AMINO)-BENZOTHIAZOLE SULFONAMIDE HIV PROTEASE INHIBITORS

(75) Inventors: Dominique Louis Nestor Ghislain Surleraux, Machelen (BE); Piet Tom Bert Paul Wigerinck, Terhagen (BE); Daniel Getman, Chesterfield, MI (US); Wim Gaston Verschueren, Berchem (BE); Sandrine Vendeville, Brussels (BE); Marie-Pierre De Bethune, Everberg (BE); Jan Octaaf Antoon De Kerpel, Lede (BE); Samuel Leo Christiaan Moors, Pellenberg (BE); Herman Augustinus De Kock, Arendonk (BE); Marieke Christiane Johanna Voets, Diepenbeek (BE)

(73) Assignee: Tibotec Pharmaceuticals Ltd. (IE)

( * ) Notice: Subject to any disclaimer, the term of this patent is extended or adjusted under 35 U.S.C. 154(b) by 401 days.

(21) Appl. No.: 10/467,609

(22) PCT Filed: Feb. 14, 2002

(86) PCT No.: PCT/EP02/01788

§ 371 (c)(1),
(2), (4) Date: Aug. 7, 2003

(87) PCT Pub. No.: WO02/083657

PCT Pub. Date: Oct. 24, 2002

(65) Prior Publication Data

US 2004/0116485 A1 Jun. 17, 2004

Related U.S. Application Data

(60) Provisional application No. 60/287,758, filed on May 2, 2001.

(30) Foreign Application Priority Data

Feb. 14, 2001 (EP) .................. 01200529

(51) Int. Cl.
*A61K 31/428* (2006.01)
*C07D 417/12* (2006.01)
(52) U.S. Cl. .................. 548/159; 548/163; 514/367
(58) Field of Classification Search .................. 548/159, 548/163; 514/367
See application file for complete search history.

(56) References Cited

U.S. PATENT DOCUMENTS

| 6,140,505 | A |   | 10/2000 | Kunda et al. |         |
|-----------|---|---|---------|--------------|---------|
| 6,143,788 | A | * | 11/2000 | Getman et al.| 514/604 |
| 6,316,496 | B1| * | 11/2001 | Getman et al.| 514/464 |
| 6,861,539 | B1| * | 3/2005  | Getman et al.| 549/437 |

FOREIGN PATENT DOCUMENTS

| EP | 0445926 B1   | 9/1991 |
| EP | 0499299 B1   | 8/1992 |
| EP | 0721331 B1   | 7/1996 |
| WO | WO 94/04492  | 3/1994 |
| WO | WO 94/05639  | 3/1994 |
| WO | WO 9405263 A1| 3/1994 |
| WO | WO 9506030 A1| 3/1995 |

(Continued)

OTHER PUBLICATIONS

Dunn et al., Genome Biology, Mar. 2002, 3(4), pp. 1-7.*

(Continued)

*Primary Examiner*—Laura L. Stockton

(57) ABSTRACT

The present invention concerns the compounds having the formula (I)

N-oxides, salts, stereoisomeric forms, racemic mixtures, prodrugs, esters and metabolites thereof, wherein $R_1$ and $R_8$ each are H, optionally substituted $C_{1-6}$alkyl, $C_{2-6}$alkenyl, $C_{3-7}$cycloalkyl, aryl, Het$^1$, Het$^2$; $R_1$ may also be a radical of formula $(R_{11a}R_{11b})NC(R_{10a}R_{10b})CR_9$—; t is 0, 1 or 2; $R_2$ is H or $C_{1-6}$alkyl; L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$; $R_3$ is $C_{1-6}$alkyl, aryl, $C_{3-7}$cycloalkyl, $C_{3-7}$cycloalkylC$_{1-4}$alkyl, or arylC$_{1-4}$alkyl; $R_4$ is H, $C_{1-4}$alkylOC(=O), carboxyl, aminoC(=O), mono- or di($C_{1-4}$alkyl)aminoC(=O), $C_{3-7}$cycloalkyl, $C_{2-6}$alkenyl, $C_{2-6}$alkynyl or optionally substituted $C_{1-6}$alkyl; A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; $R_5$ is H, OH, $C_{1-6}$alkyl, Het$^1$C$_{1-6}$alkyl, Het$^2$C$_{1-6}$alkyl, optionally substituted aminoC$_{1-6}$alkyl; $R_6$ is $C_{1-6}$alkylO, Het$^1$, Het$^1$O, Het$^2$, Het$^2$O, aryl, arylO, $C_{1-6}$alkyloxycarbonylamino or amino; and in case —A— is other than $C_{1-6}$alkanediyl then $R^6$ may also be $C_{1-6}$alkyl, Het$^1$C$_{1-4}$alkyl, Het$^1$OC$_{1-4}$alkyl, Het$^2$C$_{1-4}$alkyl, Het$^2$OC$_{1-4}$alkyl, arylC$_{1-4}$alkyl, arylOC$_{1-4}$alkyl or aminoC$_{1-4}$alkyl; whereby each of the amino groups in the definition of $R_6$ may optionally be substituted; $R^5$ and —A—$R^6$ taken together with the nitrogen atom to which they are attached may also form Het$^1$ or Het$^2$. It further relates to their use as broadspectrum HIV protease inhibitors, processes for their preparation as well as pharmaceutical compositions and diagnostic kits comprising them. It also concerns combinations thereof with another anti-retroviral agent, and to their use in assays as reference compounds or as reagents.

2 Claims, No Drawings

FOREIGN PATENT DOCUMENTS

| | | |
|---|---|---|
| WO | WO 9622287 A1 | 7/1996 |
| WO | WO-96/28464 A1 * | 9/1996 |
| WO | WO 9628418 A1 | 9/1996 |
| WO | WO 9628463 A1 | 9/1996 |
| WO | WO 9628464 A1 | 9/1996 |
| WO | WO 9628465 A1 | 9/1996 |
| WO | WO 9718205 A1 | 5/1997 |
| WO | WO 9744014 A1 | 11/1997 |
| WO | WO 9842318 A1 | 10/1998 |
| WO | WO 9933792 A2 | 7/1999 |
| WO | WO 9933793 A2 | 7/1999 |
| WO | WO 9933795 A1 | 7/1999 |
| WO | WO 9933815 A1 | 7/1999 |
| WO | WO 9965870 A2 | 12/1999 |
| WO | WO 9967254 A2 | 12/1999 |
| WO | WO 9967417 A2 | 12/1999 |
| WO | WO 00/76961 | 12/2000 |
| WO | WO 02/083657 A2 | 10/2002 |

OTHER PUBLICATIONS

Benet, L. et al., "Pharmacokinetics: The Dynamics of Drug Absorption, Distribution, and Elimination.", *Goodman and Gilman's The Pharmacological Basis of Therapeutics*, Eighth Edition, 1992, pp. 13-18, McGraw-Hill Inc.

Cross, et al., "Rules For The Nomenclature of Organic Chemistry, Section E: Stereochemistry." *Pure & Applied Chemistry*, 1976, pp. 13-30, vol. 45., Pergamon Press, Great Britain.

Hertogs, K. et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs.", *Antimicrobial Agents and Chemotherapy*, Feb. 1998, pp. 269-276, vol. 42, No. 2.

PCT Intl. Search Report, PCT/EP2002/01788, Oct. 25, 2002.

Pauwels et al., "Rapid an Automated Tetrazolium-based Colorimetric Assay for the Detection of Anti-HIV Compounds.", Journal of Virological Methods, 1988, vol. 20, pp. 309-321.

* cited by examiner

BROAD SPECTRUM 2-(SUBSTITUTED-AMINO)-BENZOTHIAZOLE SULFONAMIDE HIV PROTEASE INHIBITORS

CROSS REFERENCE TO RELATED APPLICATIONS

This application is a 35 U.S.C. 371 national phase application of PCT/EP021788, with an international filing date of Feb. 14, 2002, which claims priority to application EP 01200529.4, filed on Feb. 14, 2001, and to U.S. provisional application 60/287,758, filed on May 2, 2001.

The present invention relates to 2-(substituted-amino)-benzothiazole sulfonamides, their use as aspartic protease inhibitors, in particular as broadspectrum HIV protease inhibitors, processes for their preparation as well as pharmaceutical compositions and diagnostic kits comprising them. The present invention also concerns combinations of the present 2-(substituted-amino)-benzothiazole sulfonamides with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by aspartic protease. For instance with the HIV virus the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs) or other protease inhibitors. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever increasing resistance against the available drugs.

Resistance of retroviruses, and in particular the HIV virus, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV virus, but also on the increasingly more common resistant HIV viruses.

Known antiretrovirals, often administered in a combination therapy regimen, will eventually cause resistance as stated above. This often may force the physician to boost the plasma levels of the active drugs in order for said antiretrovirals to regain effectivity against the mutated HIV viruses. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favorable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Thus, there is a high medical need for protease inhibitors that are able to combat a broad spectrum of mutants of the HIV virus with little variance in fold resistance, have a good bioavailability and experience little or no effect on their potency due to plasma protein binding.

Up until now, several protease inhibitors are on the market or are being developed. One particular core structure (depicted below) has been disclosed in a number of references, such as, WO 95/06030, WO 96/22287, WO 96/28418, WO 96/28463, WO 96/28464, WO 96/28465 and WO 97/18205. The compounds disclosed therein are described as retroviral protease inhibitors.

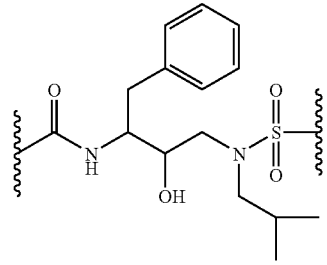

WO 99/67254 discloses 4-substituted-phenyl sulfonamides capable of inhibiting multi-drug resistant retroviral proteases.

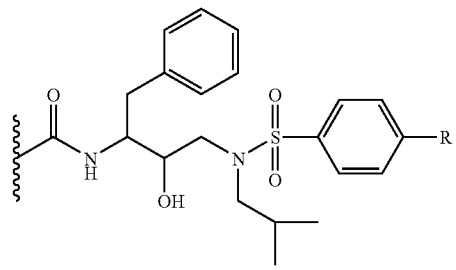

Surprisingly, the 2-(substituted-amino)-benzothiazole sulfonamides of the present invention are found to have a favorable pharmacological and pharmacokinetic profile. Not only are they active against wild-type HIV virus, but they also show a broadspectrum activity against various mutant HIV viruses exhibiting resistance against known protease inhibitors.

Though some of the present 2-(substituted-amino)-benzothiazole sulfonamides appear to fall within the generic description of some of the above cited patent publications, they are not specifically disclosed, suggested or claimed therein, nor would a person skilled in the art have been motivated to design them as broadspectrum protease inhibitors.

The present invention concerns 2-(substituted-amino)-benzothiazole protease inhibitors, having the formula

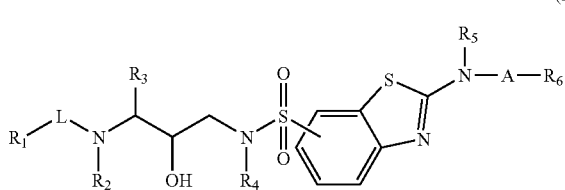

(I)

and N-oxides, salts, stereoisomeric forms, racemic mixtures, prodrugs, esters and metabolites thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, $Het^1$, $Het^1C_{1-6}$alkyl, $Het^2$ or $Het^2C_{1-6}$alkyl;

$R_1$ may also be a radical of formula

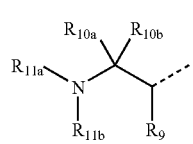

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl; whereby $R_9$, $R_{10a}$ and the carbon atoms to which they are attached may also form a $C_{3-7}$cycloalkyl radical; when L is —O—$C_{1-6}$alkanediyl-C(=O)— or —$NR_8$—$C_{1-6}$alkanediyl-C(=O)—, then R9 may also be oxo;

$R_{11a}$ is hydrogen, $C_{2-6}$alkenyl, $C_{2-6}$alkynyl, $C_{3-7}$cycloalkyl, aryl, aryl$C_{1-4}$alkyl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, $Het^1$oxycarbonyl, $Het^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkyl-carbonyl, $C_{3-7}$cycloalkyl$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, $Het^1$carbonyl, $Het^1$carbonyloxy, $Het^1C_{1-4}$alkyloxycarbonyl, $Het^2$carbonyloxy, $Het^2C_{1-4}$alkylcarbonyloxy, $Het^2C_{1-4}$alkyloxycarbonyloxy or $C_{1-4}$alkyl optionally substituted with aryl, aryloxy, $Het^2$, halogen or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

$R_{11b}$ is hydrogen, $C_{3-7}$cycloalkyl, $C_{2-6}$alkenyl, $C_{2-6}$alkynyl, aryl, $C_{1-6}$alkyloxycarbonyl, $Het^1$, $Het^2$ or $C_{1-4}$alkyl optionally substituted with halogen, hydroxy, $C_{1-4}$alkylS(=O)$_t$, aryl, $C_{3-7}$cycloalkyl, $Het^1$, $Het^2$, amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

whereby $R_{11b}$ may be linked to the remainder of the molecule via a sulfonyl group; each independently t is zero, 1 or 2;

$R_2$ is hydrogen or $C_{1-6}$alkyl;

L is —C(=O)—, —O—C(=O)—, —$NR_8$—C(=O)—, —O—$C_{1-6}$-alkanediyl-C(=O)—, —$NR_8$—$C_{1-6}$-alkanediyl-C(=O)—, —S(=O)$_2$—, —O—S(=O)$_2$—, —$NR_8$—S(=O)$_2$ whereby either the C(=O) group or the S(=O)$_2$ group is attached to the $NR_2$ moiety; and whereby the alkanediyl moiety is optionally substituted with aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

$R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-6}$alkyl optionally substituted with aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen or amino optionally mono- or disubstituted where the substituents are selected from $C_{1-4}$alkyl, aryl, aryl-$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; whereby the point of attachment to the nitrogen atom is the $C_{1-6}$alkanediyl group in those moieties containing said group;

$R_5$ is hydrogen, hydroxy, $C_{1-6}$alkyl, $Het^1C_{1-6}$alkyl, $Het^2C_{1-6}$alkyl, amino$C_{1-6}$alkyl whereby the amino group may optionally be mono- or di-substituted with $C_{1-4}$alkyl;

$R_6$ is $C_{1-6}$alkyloxy, $Het^1$, $Het^1$oxy, $Het^2$, $Het^2$oxy, aryl, aryloxy or amino; and in case —A— is other than $C_{1-6}$alkanediyl then $R^6$ may also be $C_{1-6}$alkyl, $Het^1C_{1-4}$alkyl, $Het^1$oxy$C_{1-4}$alkyl, $Het^2C_{1-4}$alkyl, $Het^2$oxy$C_{1-4}$alkyl, aryl$C_{1-4}$alkyl, aryloxy$C_{1-4}$alkyl or amino$C_{1-4}$alkyl; whereby each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, $Het^1$, $Het^2$, aryl$C_{1-4}$alkyl, $Het^1C_{1-4}$alkyl or $Het^2C_{1-4}$alkyl; and $R^5$ and —A—$R^6$ taken together with the nitrogen atom to which they are attached may also form $Het^1$ or $Het^2$.

According to one embodiment, the present invention concerns 2-(substituted-amino)-benzothiazole protease inhibitors of formula (I), and N-oxides, salts, stereoisomeric forms, racemic mixtures, prodrugs, esters and metabolites thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1C_{1-6}$alkyl, Het$^2$, Het$^2C_{1-6}$alkyl;

$R_1$ may also be a radical of formula

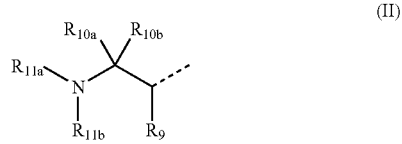

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl; whereby $R_9$, $R_{10a}$ and the carbon atoms to which they are attached may also form a $C_{3-7}$cycloalkyl radical;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, Het$^1$oxycarbonyl, Het$^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, Het$^1$carbonyl, Het$^1$carbonyloxy, Het$^1C_{1-4}$alkyloxycarbonyl, Het$^2$carbonyloxy, Het$^2C_{1-4}$alkylcarbonyloxy, Het$^2C_{1-4}$alkyloxycarbonyloxy or $C_{1-4}$alkyl optionally substituted with aryl, aryloxy, Het$^2$ or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-4}$alkyl optionally substituted with halogen, hydroxy, $C_{1-4}$alkylS(=O)$_t$, aryl, $C_{3-7}$cycloalkyl, Het$^1$, Het$^2$, amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

whereby $R_{11b}$ may be linked to the remainder of the molecule via a sulfonyl group; each independently t is zero, 1 or 2;

$R_2$ is hydrogen or $C_{1-6}$alkyl;

L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$— whereby either the C(=O) group or the S(=O)$_2$ group is attached to the NR$_2$ moiety;

$R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-6}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; whereby the point of attachment to the nitrogen atom is the $C_{1-6}$alkanediyl group in those moieties containing said group;

$R_5$ is hydrogen, hydroxy, $C_{1-6}$alkyl, Het$^1C_{1-6}$alkyl, Het$^2C_{1-6}$alkyl, amino$C_{1-6}$alkyl whereby the amino group may optionally be mono- or di-substituted with $C_{1-4}$alkyl;

$R_6$ is $C_{1-6}$alkyloxy, Het$^1$, Het$^1$oxy, Het$^2$, Het$^2$oxy, aryl, aryloxy or amino; and in case —A— is other than $C_{1-6}$alkanediyl then $R^6$ may also be $C_{1-6}$alkyl, Het$^1C_{1-4}$alkyl, Het$^1$oxy$C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-4}$alkyl; whereby each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, Het$^1$, Het$^2$, aryl$C_{1-4}$alkyl, Het$^1C_{1-4}$alkyl or Het$^2C_{1-4}$alkyl; and $R_5$ and —A—$R_6$ taken together with the nitrogen atom to which they are attached may also form Het$^1$ or Het$^2$.

This invention also envisions the quaternization of the nitrogen atoms of the present compounds. A basic nitrogen can be quaternized with any agent known to those of ordinary skill in the art including, for instance, lower alkyl halides, dialkyl sulfates, long chain halides and aralkyl halides.

Whenever the term "substituted" is used in defining the compounds of formula (I), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, for example, methyl, ethyl, propyl, butyl and 2-methyl-propyl, the like.

The term "$C_{1-6}$alkyl" as a group or part of a group defines straight and branched chained saturated hydrocarbon radicals having from 1 to 6 carbon atoms such as the groups defined for $C_{1-4}$alkyl and pentyl, hexyl, 2-methylbutyl, 3-methylpentyl and the like.

The term "$C_{1-6}$alkanediyl" as a group or part of a group defines bivalent straight and branched chained saturated hydrocarbon radicals having from 1 to 6 carbon atoms such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

The term "$C_{2-6}$alkenyl" as a group or part of a group defines straight and branched chained hydrocarbon radicals having from 2 to 6 carbon atoms containing at least one double bond such as, for example, ethenyl, propenyl, butenyl, pentenyl, hexenyl and the like.

The term "$C_{2-6}$alkynyl" as a group or part of a group defines straight and branched chained hydrocarbon radicals having from 2 to 6 carbon atoms containing at least one triple bond such as, for example, ethynyl, propynyl, butynyl, pentynyl, hexynyl and the like.

The term "$C_{3-7}$cycloalkyl" as a group or part of a group is generic to cyclopropyl, cyclobutyl, cyclopentyl, cyclohexyl or cycloheptyl.

The term "aryl" as a group or part of a group is meant to include phenyl and naphtyl which both may be optionally substituted with one or more substituents independently selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, optionally mono- or disubstituted amino$C_{1-6}$alkyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio and methylsulfonyl; whereby the optional substituents on any amino function are independently selected from $C_{1-6}$alkyl, $C_{1-6}$alkylcarbonyl, $C_{1-6}$alkyloxy-A—, Het$^1$-A—, Het$^1C_{1-6}$alkyl, Het$^1C_{1-6}$alkyl-A—, Het$^1$oxy-A—, Het$^1$oxy$C_{1-4}$akyl-A—, phenyl-A—, phenyl-oxy-A—, phenyloxy$C_{1-4}$alkyl-A—, phenyl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible di-substituted with $C_{1-4}$alkyl and whereby A is as defined above.

The term "halo$C_{1-6}$alkyl" as a group or part of a group is defined as $C_{1-6}$alkyl substituted with one or more halogen atoms, preferably, chloro or fluoro atoms, more preferably fluoro atoms. Preferred halo$C_{1-6}$alkyl groups include for instance trifluoromethyl and difluoromethyl.

The term "Het$^1$" as a group or part of a group is defined as a saturated or partially unsaturated monocyclic, bicyclic or tricyclic heterocycle having preferably 3 to 14 ring members, more preferably 5 to 10 ring members and more preferably 5 to 8 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, oxo, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, optionally mono- or disubstituted amino$C_{1-6}$alkyl, methylthio, methylsulfonyl, aryl and a saturated or partially unsaturated monocyclic, bicyclic or tricyclic heterocycle having 3 to 14 ring members which contains one or more heteroatom ring members selected from nitrogen, oxygen or sulfur and whereby the optional substituents on any amino function are independently selected from $C_{1-6}$alkyl, $C_{1-6}$alkylcarbonyl, $C_{1-6}$alkyloxy-A—, Het$^2$—A—, Het$^2C_{1-6}$alkyl, Het$^2C_{1-6}$alkyl-A—, Het$^2$oxy-A—, Het$^2$oxy$C_{1-4}$akyl-A—, aryl-A—, aryloxy-A—, aryloxy$C_{1-4}$alkyl-A—, aryl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible di-substituted with $C_{1-4}$alkyl and whereby A is as defined above.

The term "Het$^2$" as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, optionally mono- or disubstituted amino$C_{1-6}$alkyl, methylthio, methylsulfonyl, aryl, Het$^1$ and an aromatic monocyclic, bicyclic or tricyclic heterocycle having 3 to 14 ring members; whereby the optional substituents on any amino function are independently selected from $C_{1-6}$alkyl, $C_{1-6}$alkylcarbonyl, $C_{1-6}$alkyloxy-A—, Het$^1$-A—, Het$^1C_{1-6}$alkyl, Het$^1C_{1-6}$alkyl-A—, Het$^1$oxy-A—, Het$^1$oxy$C_{1-4}$akyl-A—, aryl-A—, aryloxy-A—, aryloxy$C_{1-4}$alkyl-A—, aryl$C_{1-6}$alkyl-A—, $C_{1-6}$alkyloxycarbonylamino-A—, amino-A—, amino$C_{1-6}$alkyl and amino$C_{1-6}$alkyl-A— whereby each of the amino groups may optionally be mono- or where possible di-substituted with $C_{1-4}$alkyl and whereby A is as defined above.

As used herein, the term (=O) forms a carbonyl moiety with the carbon atom to which it is attached.

As used herein before, the term "one or more" covers the possibility of all the available C-atoms, where appropriate, to be substituted, preferably, one, two or three.

When any variable (e.g. halogen or $C_{1-4}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

It is clear to a person skilled in the art that the compounds of formula (I) contain at least one asymmetric center and thus may exist as different stereoisomeric forms. This asymmetric center is indicated with a asterisk (*) in the figure below.

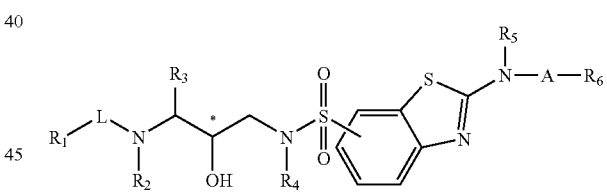

The absolute configuration of each asymmetric center that may be present in the compounds of formula (I) may be indicated by the stereochemical descriptors R and S, this R and S notation corresponding to the rules described in Pure Appl. Chem. 1976, 45, 11-30. The carbon atom marked with the asterisk (*) preferably has the R configuration.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues.

A particular group of compounds are those compounds of formula (I) wherein one or more of the following restrictions apply:

$R_1$ is hydrogen, $Het^1$, $Het^2$, aryl, $Het^1C_{1-6}$alkyl, $Het^2C_{1-6}$alkyl, arylC$_{1-6}$alkyl, more in particular, $R_1$ is hydrogen, a saturated or partially unsaturated monocyclic or bicyclic heterocycle having 5 to 8 ring members, which contains one or more heteroatom ring members selected from nitrogen, oxygen or sulfur and which is optionally substituted, phenyl optionally substituted with one or more substituents, an aromatic monocyclic heterocycle having 5 to 6 ring members, which contains one or more heteroatom ring members selected from nitrogen, oxygen or sulfur and which is optionally substituted on one or more carbon atoms, or $C_{1-6}$alkyl substituted with an aromatic monocyclic heterocycle having 5 to 6 ring members, which contains one or more heteroatom ring members selected from nitrogen, oxygen or sulfur and which is optionally substituted on one or more carbon atoms;

$R_{11a}$ is H, alkyloxycarbonyl;

$R_{11b}$ is $C_{1-4}$ alkyl optionally substituted with aryl;

$R_2$ is hydrogen;

L is —C(=O)—, —O—C(=O)—, —O—C$_{1-6}$alkanediyl-C(=O)—, —NR$_8$—C$_{1-6}$alkanediyl-C(=O)—, more in particular, L is —C(=O)—, —O—C(=O)—, —O—CH$_2$—C(=O)—, whereby in each case the C(=O) group is attached to the NR$_2$ moiety;

$R_3$ is arylC$_{1-4}$alkyl, in particular, arylmethyl, more in particular phenylmethyl;

$R_4$ is optionally substituted $C_{1-6}$alkyl, in particular $C_{1-6}$alkyl optionally substituted with aryl, Het$^1$, Het$^2$, $C_{3-7}$cycloalkyl or amino optionally mono- or disubstituted where the substituents are selected from $C_{1-4}$alkyl, aryl, Het$^1$ and Het$^2$;

A is $C_{1-6}$alkanediyl, —C(=O)— or $C_{1-6}$alkanediyl-C(=O)—, in particular, A is methylene, 1,2-ethanediyl, 1,3-propanediyl, —C(=O)— or —CH$_2$—C(=O)—;

$R_5$ is hydrogen, $C_{1-6}$alkyl, Het$^1$C$_{1-6}$alkyl, aminoC$_{1-6}$alkyl whereby the amino group may optionally be mono- or di-substituted with $C_{1-4}$alkyl;

$R_6$ is $C_{1-6}$alkyloxy, Het$^1$, aryl, amino; and in case —A— is other than $C_{1-6}$alkanediyl then $R_6$ may also be $C_{1-6}$alkyl, Het$^1$C$_{1-4}$alkyl, aryloxyC$_{1-4}$alkyl or aminoC$_{1-4}$alkyl; whereby each of the amino groups may optionally be substituted; or $R_5$ and —A—$R_6$ taken together with the nitrogen atom to which they are attached may also form Het$^1$.

A special group of compounds are those compounds of formula (I) wherein $R_1$ is Het$^1$, aryl, Het$^2C_{1-6}$alkyl; $R_2$ is hydrogen; L is —C(=O)—, —O—C(=O)—, —O—CH$_2$—C(=O)—, whereby in each case the C(=O) group is attached to the NR$_2$ moiety; $R_3$ is phenylmethyl; and $R_4$ is $C_{1-6}$alkyl.

Also a special group of compounds are those compounds of formula (I) wherein A is $C_{1-6}$alkanediyl or —C(=O)—; $R_5$ is hydrogen, methyl, Het$^1$C$_{1-6}$alkyl, aminoC$_{1-6}$alkyl whereby the amino group may optionally be mono- or di-substituted with $C_{1-4}$alkyl; $R_6$ is $C_{1-6}$alkyloxy, Het$^1$, amino; and in case —A— is other than $C_{1-6}$alkanediyl then $R^6$ may also be $C_{1-6}$alkyl, Het$^1$C$_{1-4}$alkyl or aminoC$_{1-4}$alkyl; whereby each of the amino groups may optionally be substituted.

An interesting group of compounds are those compounds of formula (I) wherein —A— is carbonyl and $R_6$ is aryl, Het$^1$C$_{1-4}$alkyl, aryloxyC$_{1-4}$alkyl or aminoC$_{1-4}$alkyl, whereby the amino groups may optionally be substituted; or —A— is carbonyl, $R_6$ is $C_{1-4}$alkyl and $R_5$ is Het$^1$C$_{1-6}$alkyl or amino C$_{1-6}$alkyl whereby the amino group may optionally be mono- or di-substituted with $C_{1-4}$alkyl.

Another interesting group of compounds are those compounds of formula (I) wherein —A— is $C_{1-6}$alkanediyl and $R_6$ is amino and Het$^1$; whereby the amino group may optionally be mono- or di-substituted with $C_{1-4}$alkyl.

Another interesting group of compounds are those compounds of formula (I) wherein $R_1$ hydrogen, $C_{1-6}$alkyl, $C_{2-6}$alkenyl, arylC$_{1-6}$alkyl, $C_{3-7}$cycloalkyl, $C_{3-7}$cycloalkylC$_{1-6}$alkyl, aryl, Het$^1$, Het$^1$C$_{1-6}$alkyl, Het$^2$, Het$^2$C$_{1-6}$alkyl; wherein Het$^1$ is a saturated or partially unsaturated monocyclic heterocycle having 5 or 6 ring members, which contains one or more heteroatom ring members selected from nitrogen, oxygen or sulfur and which is optionally substituted on one or more carbon atoms.

Another interesting group of compounds are those compounds of formula (I) wherein L is —O—C$_{1-6}$alkanediyl-C(=O)—.

Another interesting group of compounds are those compounds of formula (I) wherein A is $C_{1-6}$alkanediyl, —C(=O)— or $C_{1-6}$alkanediyl-C(=O)—; whereby the point of attachment to the nitrogen atom is the $C_{1-6}$alkanediyl group in those moieties containing said group;

$R_5$ is hydrogen, $C_{1-6}$alkyl, Het$^1$C$_{1-6}$alkyl, Het$^2$C$_{1-6}$alkyl, aminoC$_{1-6}$alkyl whereby the amino group may optionally be mono- or di-substituted with $C_{1-4}$alkyl; and in case —A— is —C(=O)— then $R^6$ is $C_{1-6}$alkyloxy, Het$^1$, Het$^1$oxy or Het$^2$oxy, aryl, Het$^1$C$_{1-4}$alkyl, Het$^1$oxyC$_{1-4}$alkyl, Het$^2$C$_{1-4}$alkyl, Het$^2$oxyC$_{1-4}$alkyl, arylC$_{1-4}$alkyl, aryloxyC$_{1-4}$alkyl or aminoC$_{1-4}$alkyl; and in case —A— is $C_{1-6}$alkanediyl then $R^6$ is amino, $C_{1-6}$alkyloxy, Het$^1$, Het$^1$oxy or Het$^2$oxy; and in case —A— is $C_{1-6}$alkanediyl-C(=O)— then $R^6$ is $C_{1-6}$alkyloxy, Het$^1$, Het$^1$oxy or Het$^2$oxy, aryl, $C_{1-6}$alkyl, Het$^1$C$_{1-4}$alkyl, Het$^1$oxyC$_{1-4}$alkyl, Het$^2$C$_{1-4}$alkyl, Het$^2$oxyC$_{1-4}$alkyl, arylC$_{1-4}$alkyl, aryloxyC$_{1-4}$alkyl or aminoC$_{1-4}$alkyl;

whereby each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, Het$^1$, Het$^2$, arylC$_{1-4}$alkyl, Het$^1$C$_{1-4}$alkyl or Het$^2$C$_{1-4}$alkyl; and $R_5$ and —A—$R^6$ taken together with the nitrogen atom to which they are attached may also form Het$^1$ whereby Het$^1$ is substituted by at least an oxo group.

Interesting compounds are those wherein L is —O—C$_{1-6}$alkanediyl-C(=O)— or —NR$_8$—C$_{1-6}$-alkanediyl-C(=O)— and $R_1$ is a radical of formula

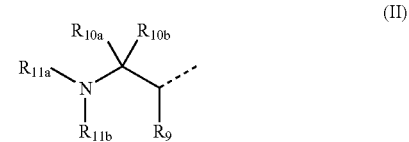

(II)

wherein $R_9$ is oxo;

$R_{10a}$ and $R_{10b}$ are, each independently, hydrogen or $C_{1-4}$alkyl optionally substituted with aryl, Het$^1$, Het$^2$, $C_{1-4}$alkyloxycarbonyl, carboxyl, aminocarbonyl, hydroxy, or amino optionally mono- or disubstituted where the substituents are selected from $C_{1-4}$alkyl, $R_{11a}$ is aryl$C_{1-4}$alkyl, or $C_{1-4}$alkyl optionally substituted with aryl or halogen and $R_{11b}$ is hydrogen, or $C_{1-6}$alkyloxycarbonyl.

Also interesting compounds are those wherein L is —O—$C_{1-6}$alkanediyl-C(=O)— or —NR$_8$—$C_{1-6}$alkanediyl-C(=O)— and $R_1$ is a radical of formula

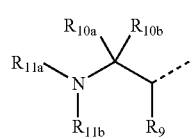

(II)

wherein $R_9$ is oxo, $R_{10a}$ and $R_{10b}$ are hydrogen, $R_{11a}$ is aryl$C_{1-4}$alkyl wherein the aryl group is substituted with a halogen and $R_{11b}$ is hydrogen, or $C_{1-6}$alkyloxycarbonyl.

Other interesting compounds are those wherein L is —O—$C_{1-6}$alkanediyl-C(=O)— or —NR$_8$—$C_{1-6}$alkanediyl-C(=O)— and $R_1$ is a radical of formula

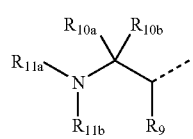

(II)

wherein $R_9$ is oxo, $R_{10a}$ and $R_{10b}$ are hydrogen, $R_{11a}$ is m-fluorobenzyl and $R_{11b}$ is hydrogen, or $C_{1-6}$alkyloxycarbonyl.

Yet other interesting compounds are those wherein L is —O—$C_{1-6}$alkanediyl-C(=O)— or —NR$_8$—$C_{1-6}$alkanediyl-C(=O)— and $R_1$ is a radical of formula

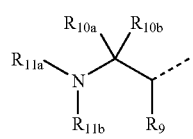

(II)

wherein $R_9$ is oxo, $R_{10a}$ and $R_{10b}$ are hydrogen, $R_{11a}$ is m-fluorobenzyl and $R_{11b}$ is hydrogen.

Other interesting compounds are those wherein L is —O—$C_{1-6}$alkanediyl-C(=O)— or —NR$_8$—$C_{1-6}$alkanediyl-C(=O)— and $R_1$ is a radical of formula

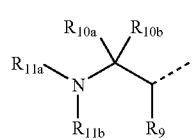

(II)

wherein $R_9$ is oxo, $R_{10a}$ and $R_{10b}$ are hydrogen, $R_{11a}$ is m-fluorobenzyl and $R_{11b}$ is tert-butyloxycarbonyl.

Interestingly, the compounds of the present invention may comprise chemically reactive moieties capable of forming covalent bonds to localized sites such that said compound have increased tissue retention and half-lives. The term "chemically reactive group" as used herein refers to chemical groups capable of forming a covalent bond. Reactive groups will generally be stable in an aqueous environment and will usually be carboxy, phosphoryl, or convenient acyl group, either as an ester or a mixed anhydride, or an imidate, or a maleimidate thereby capable of forming a covalent bond with functionalities such as an amino group, a hydroxy or a thiol at the target site on for example blood components.

Upon administration to an individual in need thereof, said compound is capable of forming covalent bonds to localized sites, with blood component for example, such that said compound according to the invention has increased tissue retention and half-lives. Usually, the covalent bond that is formed should be able to be maintained during the lifetime of the blood component, unless it is intended to be a release site. A major advantage of said new compound is the small amount of compound necessary to provide an effective effect. The reasons for this advantage are explained by the targeting of the delivery, the high yield of reaction between the reactive entity Y and reactive functionality and the irreversible nature of the bond formed after reaction. Furthermore, once bound to the membrane or tissue said compound according to the invention is not susceptible to liver metabolism, kidney filtration and excretion, and may even be protected from protease (inclusive of endopeptidase) activity which usually leads to loss of activity and accelerated elimination.

"Blood components" as used herein refers to either fixed or mobile blood components. Fixed blood components are non-mobile blood components and include tissues, membrane receptors, interstitial proteins, fibrin proteins, collagens, platelets, endothelial cells, epithelial cells and their associated membrane and membranous receptors, somatic body cells, skeletal and smooth muscle cells, neuronal components, osteocytes and osteoclasts and all body tissues especially those associated with the circulatory and lymphatic systems. Mobile blood components are blood components that do not have a fixed situs for any extended period of time, generally not exceeding 5, more usually one minute. These blood components are not membrane-associated and are present in the blood for extended periods of time and are present in a minimum concentration of at least 0.1 μg/ml. Mobile blood components include serum albumin, transferrin, ferritin and immunoglobulins such as IgM and IgG. The half-life of mobile blood components is at least about 12 hours.

The compounds of formula (I) can generally be prepared using procedures analogous to those procedures described in WO 95/06030, WO 96/22287, WO 96/28418, WO 96/28463, WO 96/28464, WO 96/28465 and WO 97/18205.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

Scheme A
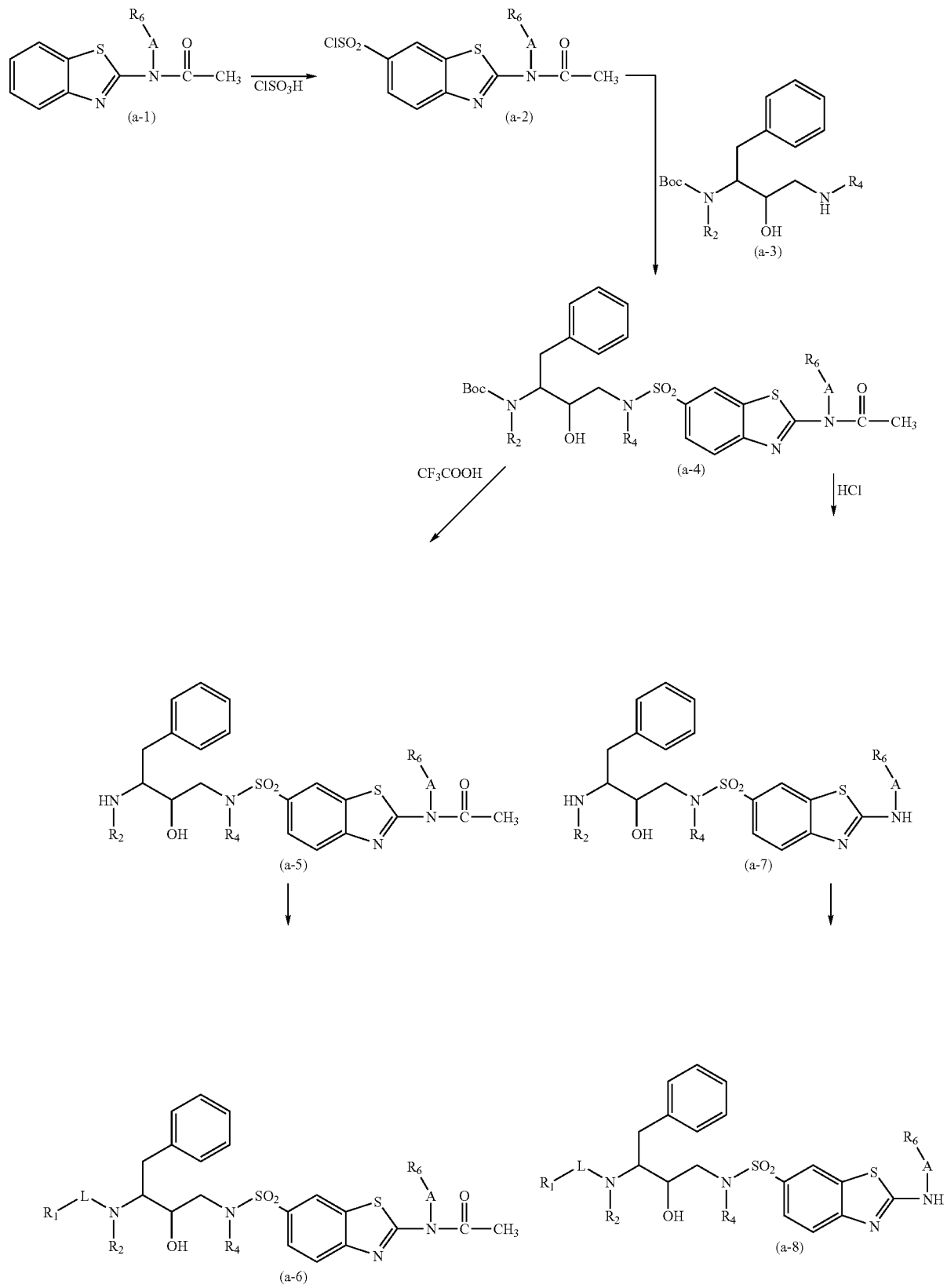

The 2-acetamido-6-chlorosulfonylbenzothiazole (intermediate a-2) was prepared following the procedure described in EP-A-0,445,926. Intermediates a-4 were prepared by reacting an intermediate a-3, prepared according to the procedure described in WO97/18205 and also depicted in scheme F, with an intermediate a-2 in a reaction-inert solvent such as dichloromethane, and in the presence of a base such as triethylamine and at low temperature, for example at 0° C. The Boc group in the intermediate a-3 is a protective tert-butyloxycarbonyl group. It may conveniently be replaced by another suitable protective group such as phtalimido or benzyloxycarbonyl. Using intermediate a-4 as a starting material, intermediate a-5 was deprotected using an acid such as trifluoroacetic acid in a suitable solvent such as dicloromethane. The resulting intermediate may be further reacted with an intermediate of formula $R_1$—L-(leaving group) in the presence of a base such as triethylamine and optionally in the presence of 1-(3-dimethylaminopropyl)-3-ethylcarbodiimide hydrochloric acid (EDC) or an alcohol such as tert-butanol, and in a suitable solvent such as dichloromethane; thus forming intermediates a-6. Particularly, intermediates of formula $R_1$—C(=O)—OH are suitable to further react with an intermediate a-5.

Alternatively, intermediates a-4 may be deprotected with a strong acid such as hydrochloric acid in isopropanol, in a suitable solvent such as a mixture of ethanol and dioxane, thus preparing an intermediate a-7. Intermediates a-8 can be prepared analogously to the procedure described for the preparation of intermediates a-6.

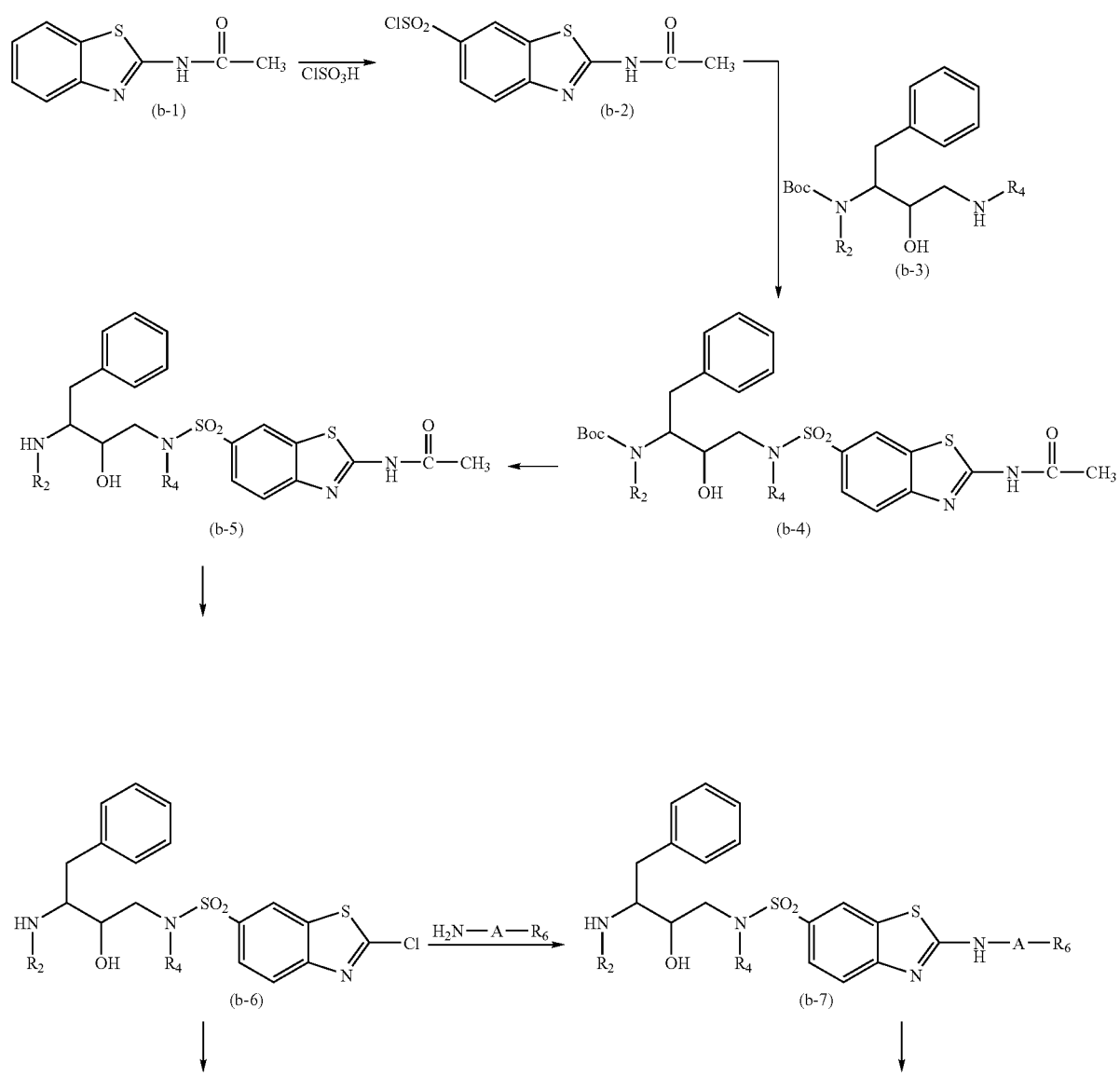

Scheme B

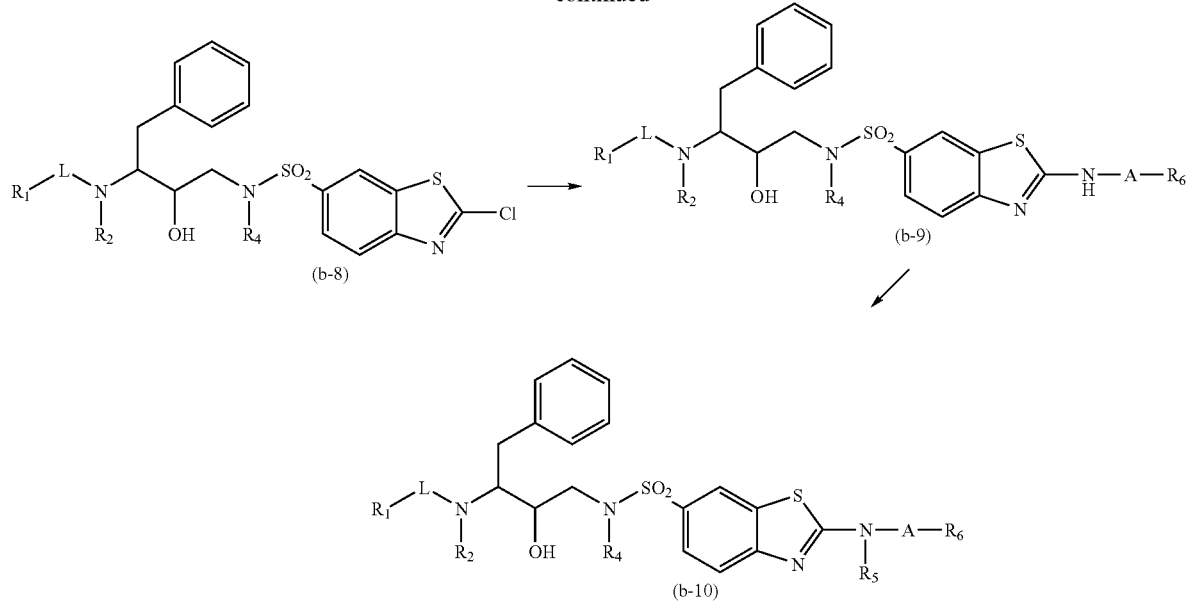

Intermediate b-5 can be prepared according to the procedure described in scheme A. The aminobenzothiazole derivative b-5 can be de-aminated by for instance treatment with sodium nitrite in combination with phosphoric acid, and subsequently with copper sulphate and sodium chloride, thus obtaining an intermediate b-6. Intermediate b-6 may then be reacted with an intermediate of formula $R_1$—L-(leaving group) in the presence of a base such as triethylamine and optionally in the presence of EDC or an alcohol such as t-butanol, and in a suitable solvent such as dichloromethane, thus obtaining an intermediate b-8. Intermediate b-8 may further be derivatized with an amine of formula $H_2N$—A—$R_6$ in a suitable solvent such as acetonitrile to obtain an intermediate b-9. Alternatively, intermediates b-6 may first be reacted with $H_2N$—A—$R_6$ and then with formula $R_1$—L-(leaving group) as is shown in scheme B. Intermediate b-9 can finally be further reacted with $R_5$COCl or a functional equivalent thereof in the presence of a base such as triethylamine and in a suitable solvent such as dichloromethane. Conveniently, said reaction is carried out under an inert atmosphere.

Scheme C

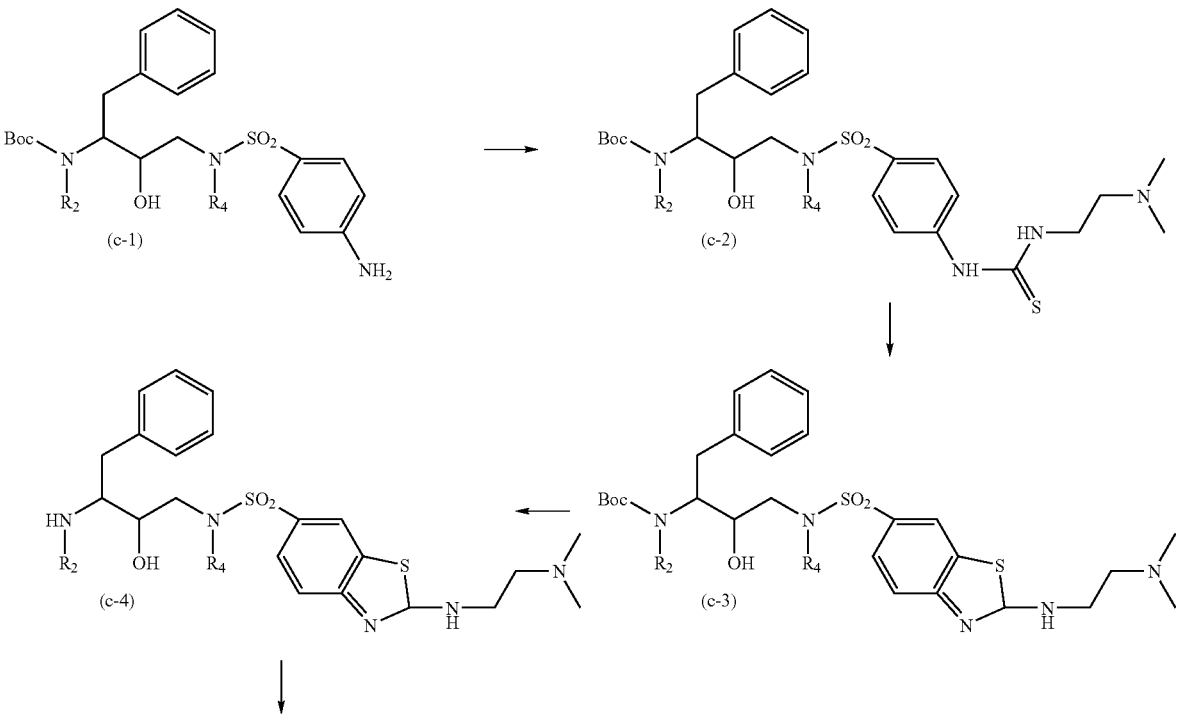

-continued

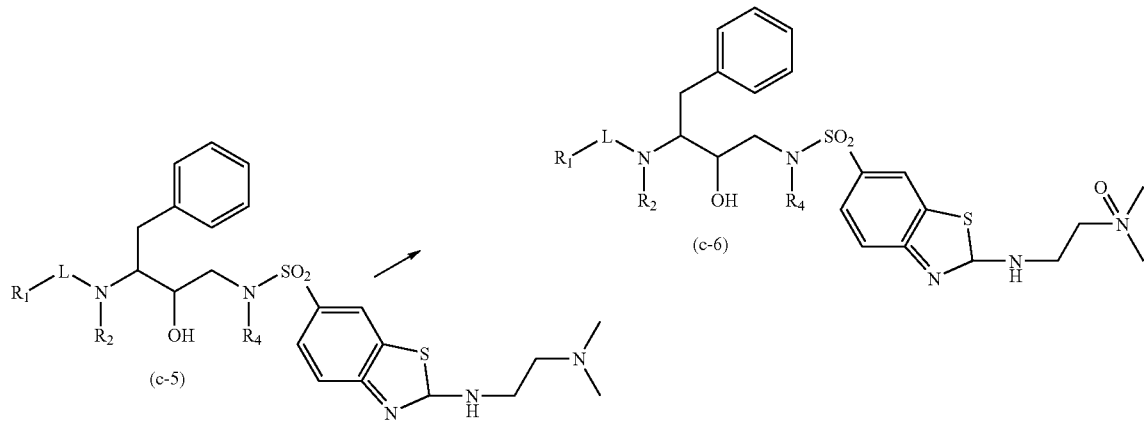

An alternative way of preparing compounds of formula (I) is exemplified in scheme C. Intermediate c-1, prepared according to the procedure described in U.S. Pat. No. 6,140,505, was reacted with thiocarbonyldiimidazole in a reaction inert solvent such as tetrahydrofuran, and the resulting intermediate was further reacted with an amine such as for instance dimethylethylamine, thus obtaining the thiourea derivative c-2. Said intermediate c-2 was then cyclized with bromine in the presence of an acid such as acetic acid, thus obtaining a benzthiazole derivative c-3. The following two steps in scheme C are analogous as those described for the preparation of intermediates a-5 and a-6 in scheme A. If so desired, intermediate c-5 can be N-oxidized using for example meta chloroperbenzoic acid in dichloromethane.

A particular way of preparing acetamide substituted benzothiazoles is depicted in scheme D.

Scheme D

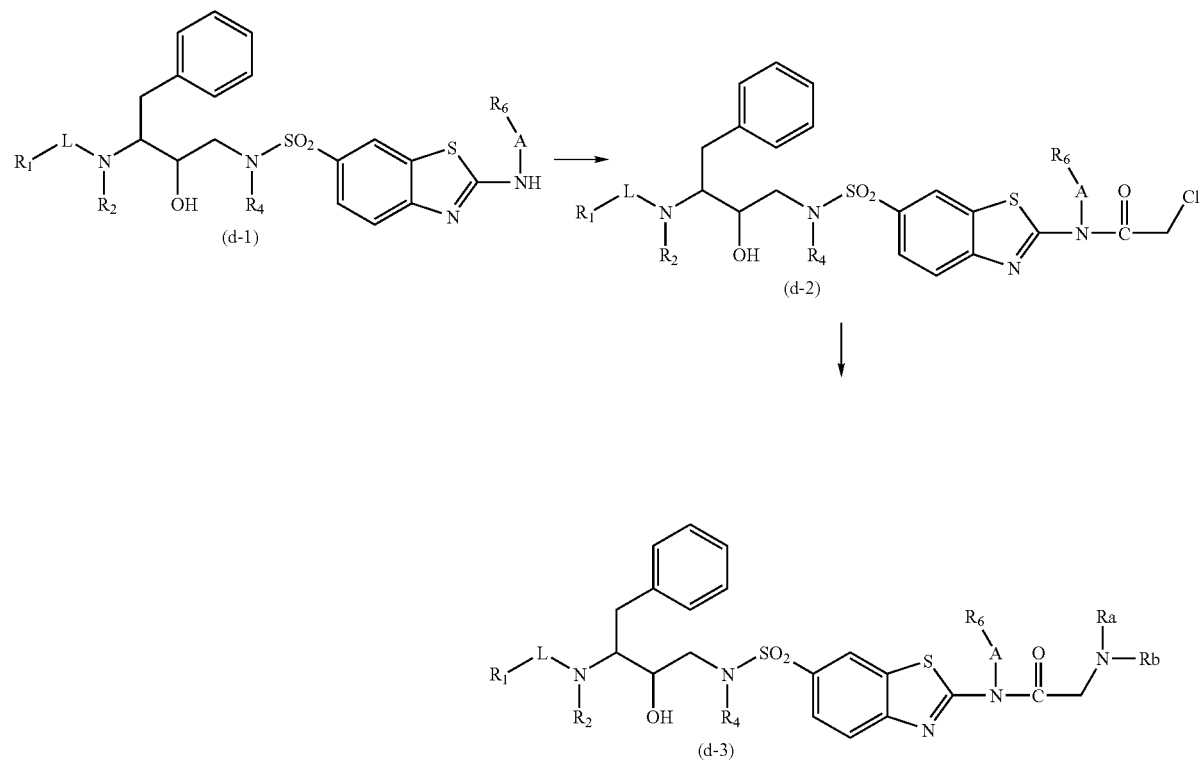

Intermediate d-1, prepared following the procedure as described in Scheme A, may be reacted with chloroacetylchloride, or a functional analogue, in the presence of a base such as triethiylamine and in a solvent such as 1,4-dioxane in order to obtain an amide of formula d-2. Said intermediate d-2 can further be reacted with an amine of formula NRaRb whereby Ra and Rb are defined as the possible substituents on an amino group in the variable $R_6$.

Another particular way of preparing acetamide substituted benzothiazoles is depicted in scheme E.

Intermediate e-2 can be prepared by treating intermediate e-1, prepared following the procedure described in scheme A, with a base such as sodiumcarbonate in an aqueous medium such as a water dioxane mixture. The synthesis steps depicted in scheme E to obtain intermediate e-6 are all analogous to reaction procedures described in the above synthesis schemes.

A number of intermediates and starting materials used in the foregoing preparations are known compounds, while others may be prepared according to art-known methodologies of preparing said or similar compounds.

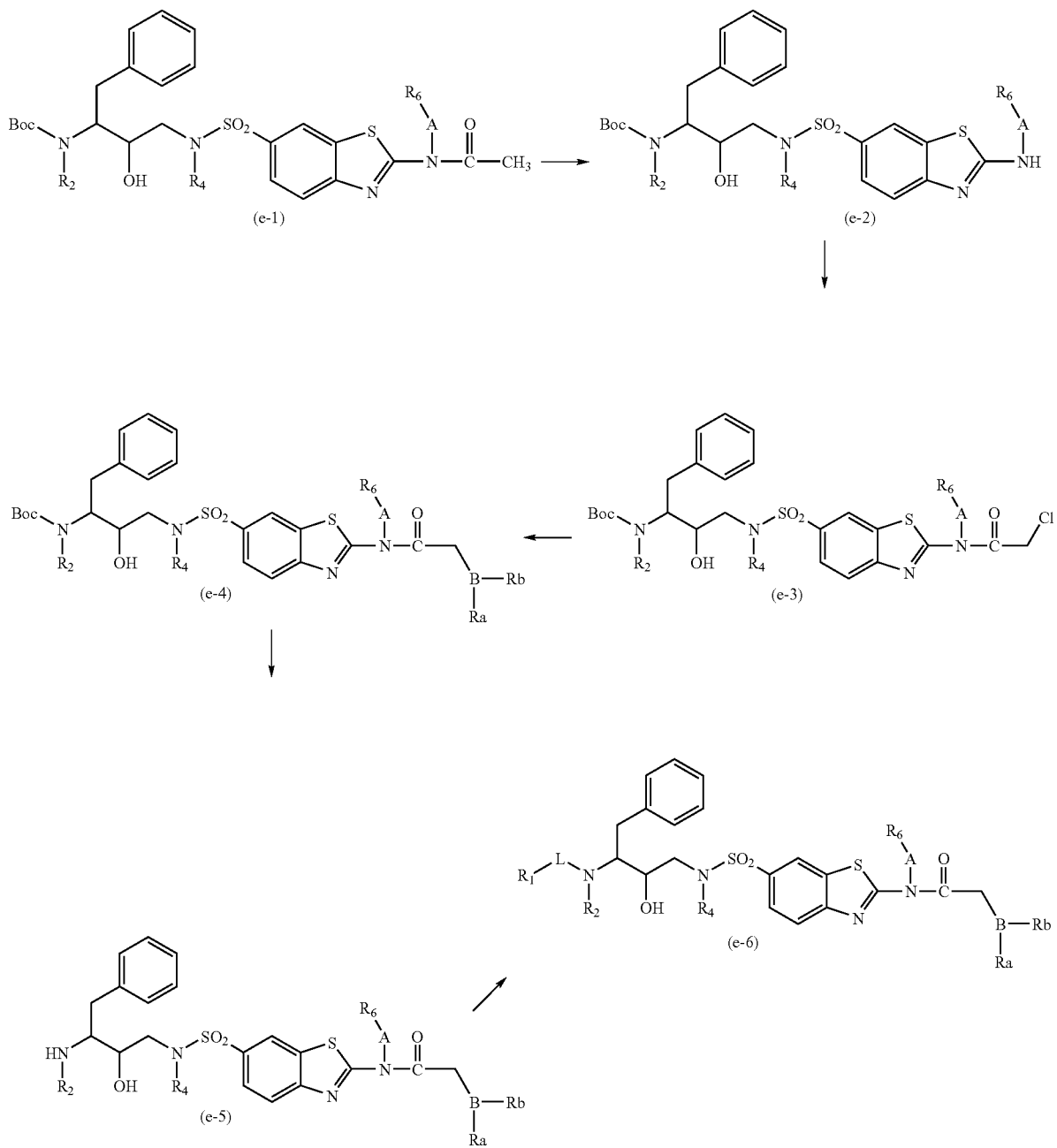

Scheme E

Scheme F
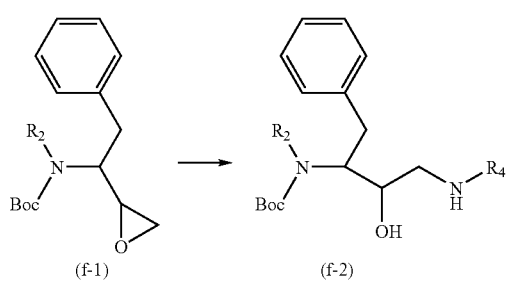
Intermediate f-2, corresponding to intermediate a-3 in scheme A, may be prepared by adding an amine of formula $H_2N-R_4$ to an intermediate f-1 in a suitable solvent such as isopropanol.
The compounds according to the present invention may also be prepared according to the method as depicted in scheme G.
Scheme G
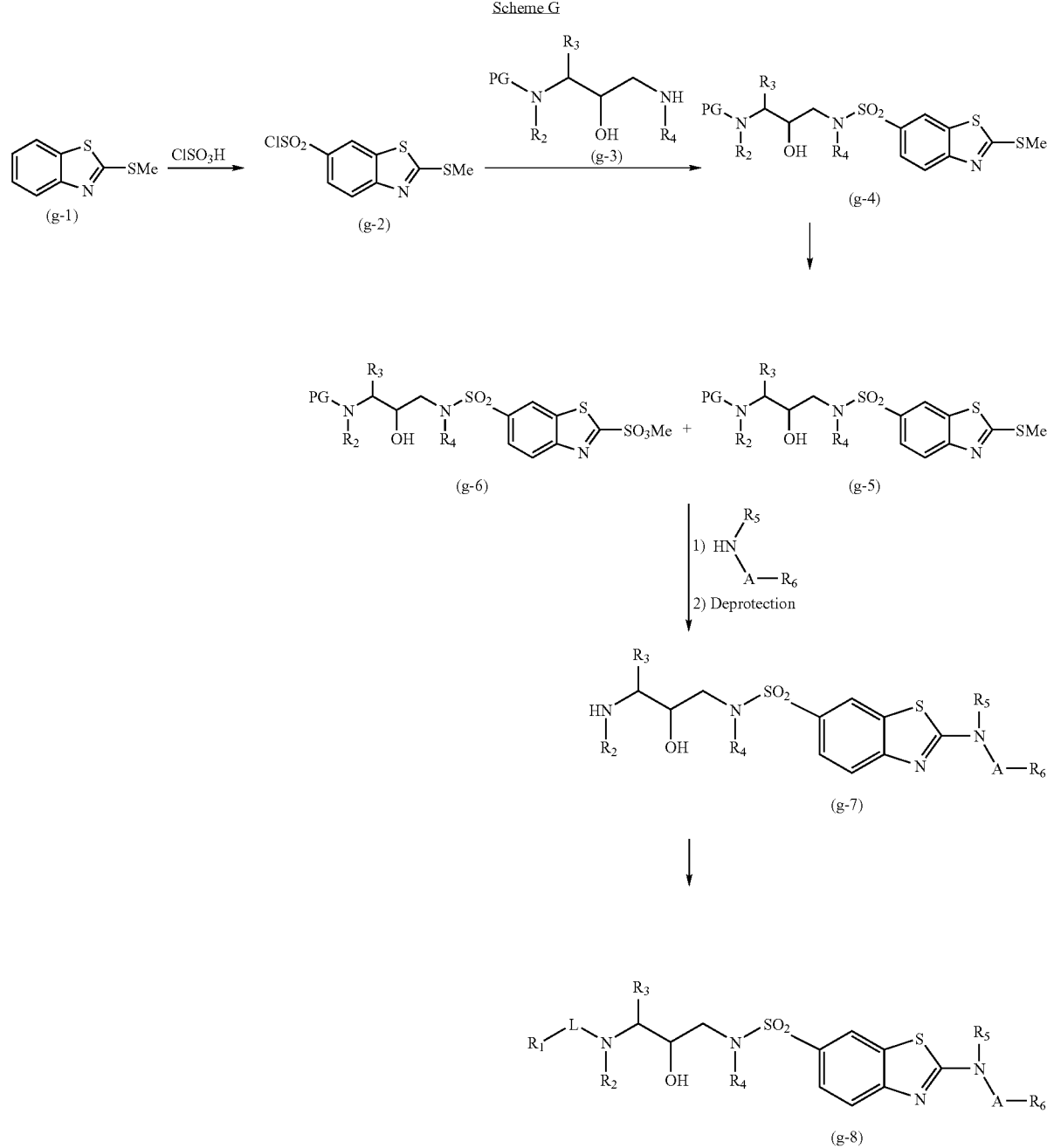

The benzothiazole derivative g-1 may be reacted with chlorosulfonic acid and subsequently treated with thionylchloride to yield intermediate g-2. Said intermediate g-2 may be further reacted with intermediate g-3 yielding an intermediate g-4 wherein PG means a suitable protecting group such as for example Boc. Said reaction may be performed in a suitable solvent such as for example 2-methyltetrahydrofuran and optionally in the presence of a suitable base such as triethylamine, The intermediate g-4 may then be reacted with a suitable reagent such as meta-chloroperoxybenzoic acid (mCPBA) or magnesium monoperoxyphtalate hexahydrate (MMPP) in the presence of a suitable solvent such as 2-methyltetrahydrofuran in ethanol thereby producing intermediates g-5 and g-6.

Intermediates g-5 and g-6 may be further derivatized with a compound of formula $HN(R_5)A\text{—}R_6$ yielding intermediate g-7 after a deprotection reaction. Intermediate g-7 may then be reacted with an intermediate of formula $R_1\text{—}L\text{-(leaving group)}$ in the present of a base such as triethylamine and optionally in the presence of EDC or an alcohol such as t-butanol, and in a suitable solvent such as dichloromethane, thus obtaining the compound g-8 which is compound of formula (I).

Another particular way of preparing some compounds according to the invention is depicted in scheme H.

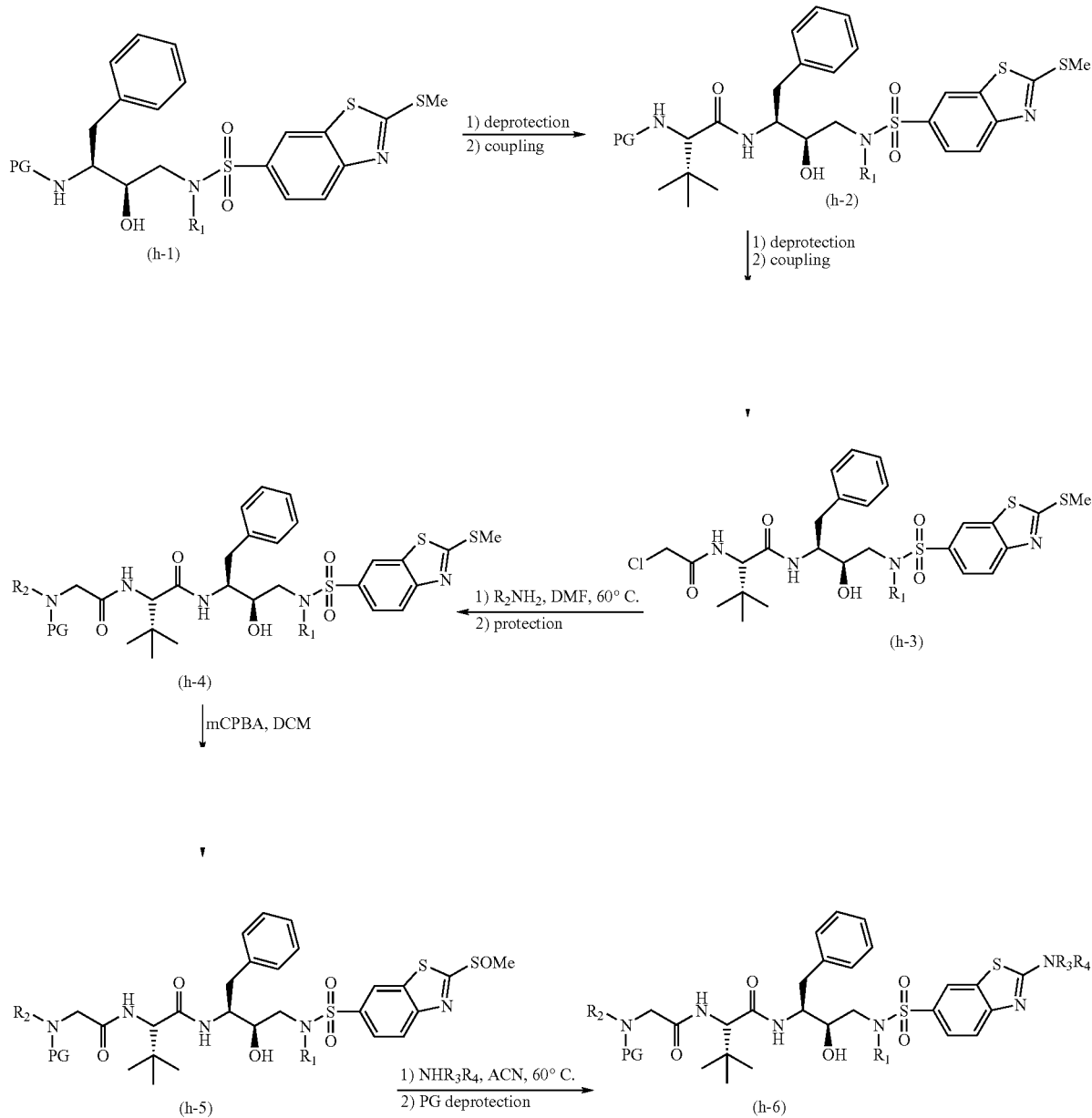

Scheme H

After deprotection of the protective group of h-1 using methods known in the art, such as HCl in isopropanol when PG is a Boc group, the free amine is reacted with a carboxylic acid, in the presence of a coupling agent such as EDC and HOBt, in an organic solvent such as dichloromethane, to yield h-2.

In one preferred embodiment, the carboxylic acid is the Boc-protected L-tert-Leucine.

h-2 is then deprotected as previously described and reacted with chloroacetic acid in the presence of EDC and HOBt, in dichloromethane, to give intermediate h-3, which is further substituted by a primary amine in an organic solvent such as dimethyl formamide (DMF), under heating conditions, then protected by an adequate protective group such as Boc, to give intermediate h-4.

Intermediate h-4 is reacted with meta-chloroperoxybenzoic acid in dichloromethane to give the sulfoxide h-5, further substituted by an amine of formula $NHR_3R_4$ in an organic solvent such as acetonitrile, under heating conditions. The final compound h-6 is obtained after removal of the protective group as previously described.

The compounds of formula (I) may also be converted to the corresponding N-oxide forms following art-known procedures for converting a trivalent nitrogen into its N-oxide form as is shown for instance for intermediate c-6 in scheme C. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

An interesting group of intermediates are those intermediates of formula a-8, b-9 or d-1 wherein —A—$R_6$ is hydrogen. Said intermediates may also have pharmacological properties similar to those pharmacological properties of the compounds of formula (I).

The present compounds can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of a compound of formula (I). The pharmaceutical preparations can be prepared in a manner known per se to one of skill in the art. For this purpose, at least one of a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Due to their favorable pharmacological properties, particularly their activity against multi-drug resistant HIV protease enzymes, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

In a preferred embodiment, the invention relates to the use of a compound of formula (I) or any subgroup thereof in the manufacture of a medicament for treating or combating infection or disease associated with multi-drug resistant retrovirus infection in a mammal, in particular HIV-1 infection. Thus, the invention also relates to a method of treating a retroviral infection, or a disease associated with multi-drug resistant retrovirus infection comprising administering to a mammal in need thereof an effective amount of a compound of formula (I) or a subgroup thereof.

In another preferred embodiment, the present invention relates to the use of formula (I) or any subgroup thereof in the manufacture of a medicament for inhibiting a protease of a multi-drug resistant retrovirus in a mammal infected with said retrovirus, in particular HIV-1 retrovirus.

In another preferred embodiment, the present invention relates to the use of formula (I) or any subgroup thereof in the manufacture of a medicament for inhibiting multi-drug resistant retroviral replication, in particular HIV-1 replication.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4; fusion inhibitors, such as, for example, T20, T1249, SHC-C, PRO542; co-receptor binding inhibitors, such as, for example, AMD 3100 (Bicyclams), TAK 779; RT inhibitors, such as, for example, foscarnet and prodrugs, MIV-310; nucleoside RTIs, such as, for example, AZT, 3TC, DDC, DDI, D4T, Abacavir, FTC, DAPD, dOTC; nucleotide RTIs, such as, for example, PMEA, PMPA, tenofovir; NNRTIs, such as, for example, nevirapine, delavirdine, efavirenz, 8 and 9-Cl TIBO (tivirapine), loviride, TMC-125, TMC-120, MKC-442, UC 781, Capravirine, DPC 961, $DPC_{963}$, DPC082, DPC083, calanolide A, SJ-3366, TSAO, 4"-deaminated TSAO; RNAse H inhibitors, such as, for example, SP1093V, PD126338; TAT inhibitors, such as, for example, RO-5-3335, K12, K37; integrase inhibitors, such as, for example, L 708906, L 731988; protease inhibitors, such as, for example, amprenavir, ritonavir, nelfinavir, saquinavir, indinavir, lopinavir, BMS 232632, BMS 186316, DPC 681, DPC 684, tipranavir, AG1776, DMP 450, L 756425, PD178390, PNU 140135; glycosylation inhibitors, such as, for example, castanospermine, deoxynojirimycine.

The combination may provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) antibiotics (e.g., pentamidine isothiorate), vaccines or hormones (e.g growth hormone) to ameliorate, combat, or eliminate HIV infection and its symptoms.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO-94/05263, PCT application No. PCT/EP98/01773, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion.

Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another aspect of the present invention concerns a kit or container comprising a compound of formula (I) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in high-throughput target-analyte assays such as those for measuring the efficacy of said compound in HIV treatment.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. *Antimicrob Agents Chemother*, 1998; 42(2):269-276, incorporated by reference).

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of formula (I) in the case of administration to a patient approximately 75 kg in weight is 1 mg to 1 g, preferably 3 mg to 0.5 g. The dose can be administered in the form of an individual dose, or divided into several, e.g. two, three, or four, individual doses.

EXPERIMENTAL PART
Preparation of the Compounds of Formula (I) and their Intermediates

Example 1
Preparation of Compound 29

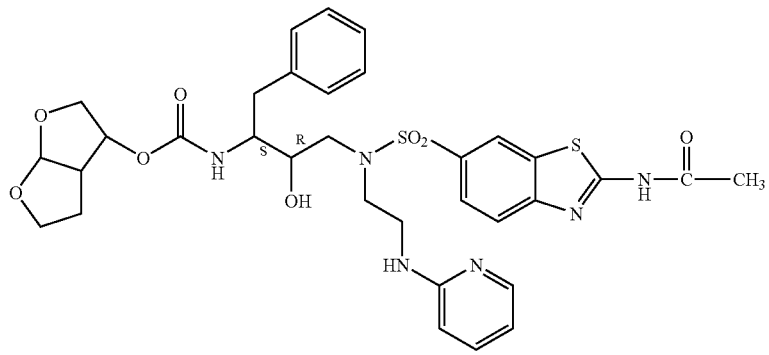

compound 29

A mixture of 1.56 g of intermediate a-3 (R$_2$=H and R$_4$=—CH$_2$—CH$_2$—NH-(2-pyridinyl)) and 0.59 g of triethylamine in 50 ml of dichloromethane was stirred at 0° C. Then 1.25 g of 2-(acetylamino)-6-benzothiazolesulfonyl chloride, was added and the reaction mixture stirred overnight at room temperature. After washing with water, the organic layer was separated, dried and the solvent evaporated. The brown solid obtained was re-dissolved in methanol at 70° C., cooled and filtered off, yielding 1.9 g (75%) of intermediate a-4 (R$_2$=H, R$_4$=—CH$_2$—CH$_2$—NH-(2-pyridinyl) and —A—R$_6$=H).

To a mixture of 6 g of intermediate a-4 (R$_2$=H, R$_4$=—CH$_2$—CH$_2$—NH-(2-pyridinyl) and —A—R$_6$=H) in 50 ml of dichloromethane, 7.3 ml of trifluoracetic acid were added. The reaction mixture was stirred at room temperature for 6 hours. Extra dichloromethane was added and washed with NaHCO$_3$ solution. The organic layer was dried and the solvent evaporated under reduced pressure, yielding 4.1 g (81%) of intermediate a-5 (R$_2$=H, R$_4$=—CH$_2$—CH$_2$—NH-(2-pyridinyl) and —A—R$_6$=H).

A mixture of 0.60 g of intermediate a-5 (R$_2$=H, R$_4$=—CH$_2$—CH$_2$—NH-(2-pyridinyl) and —A—R$_6$=H), 0.29 g of 1-[[[[(3S,3aR,6aS)+(3R,3aS,6aR)-hexahydrofuro[2,3-b]furan-3-yl]oxy]carbonyl]oxy]-2,5-pyrrolidinedione (prepared analogously to the procedure described in WO9967417) and 0.33 g of triethylamine in 15 ml of dichloromethane was stirred at room temperature for 24 hours. Solvents were evaporated and the solid obtained was redissolved in methanol at 70° C., cooled and filtered off, yielding 0.53 g (69%) of compound 29. Mass Spectral data: m/z=711 (M+H)

Example 2
Preparation of Compound 31

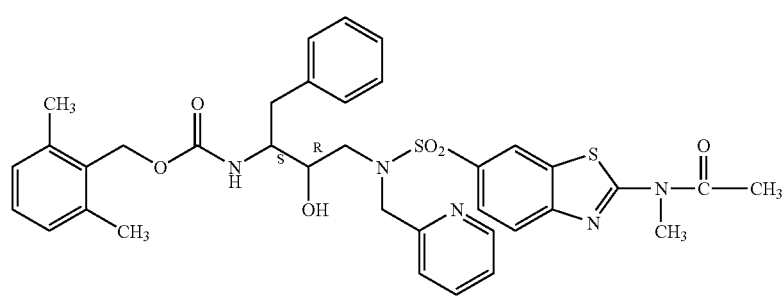

compound 31

A mixture of 540 mg of intermediate a-5 (R$_2$=H, R$_4$=—CH$_2$-(2-pyridinyl) and —A—R$_6$=H), 135 mg of tert-butanol, 192 mg of EDC and 101 mg of triethylamine in 5 ml of dichloromethane, was stirred overnight at room temperature. The reaction mixture was then washed with a Na$_2$CO$_3$ solution and brine. The organic layer was separated, dried and the solvent evaporated. The residue was purified by preparative-HPLC, yielding 184 mg (26%) of compound 31. Mass spectral data m/z=702 (M+H)

Example 3
Preparation of Compound 33

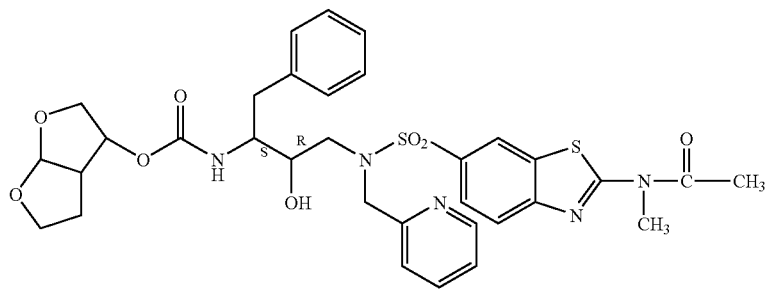

compound 33

A mixture of 540 mg of intermediate a-5 ($R_2$=H, $R_4$=—$CH_2$-(2-pyridinyl) and —A—$R_6$=H), 271 mg of 1-[[[[(3S, 3aR,6aS)+(3R,3aS,6aR)-hexahydrofuro[2,3-b]furan-3-yl]oxy]carbonyl]oxy]-2,5-pyrrolidinedione and 101 mg of triethylamine in 5 ml of dichloromethane was stirred at room temperature for 24 hours. The reaction mixture was then washed with a $Na_2CO_3$ solution and brine. The organic layer was separated, dried and the solvent evaporated. The residue was purified by preparative-HPLC, yielding 161 mg (23%) of compound 33. Mass spectral data: m/z=696 (M+H)

Example 4
Preparation of Compound 2

To a mixture of 0.3 g of racemic intermediate a-8 ($R_2$=H, $R_4$=isobutyl, —A—$R_6$=H and —L—$R_1$=[[hexahydrofuro[2, 3-b]furan-3-yl]oxy]carbonyl) and 0.061 g triethylamine in anhydrous dioxane is added in several portions 0.18 g ethyl To a mixture of 0.3 g of racemic intermediate a-8 ($R_2$=H, $R_4$=isobutyl, —A—$R_6$=H and —L—$R_1$=[[hexahydrofuro[2, chloroformate. The reaction mixture was heated overnight to 60° C. To the mixture is added 10 ml water and 0.4 g potassium carbonate followed by 2 hours of stirring. Dioxane was removed in vacuo. The aqueous phase was extracted with dichloromethane. The combined organic phase was concentrated and the obtained residue purified by chromatography yielded 0.23 g (68%) of compound 2.

compound 2

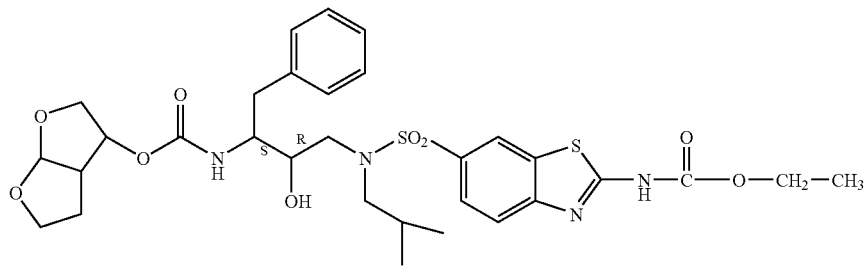

Example 5
Preparation of Compound 56 compound 56

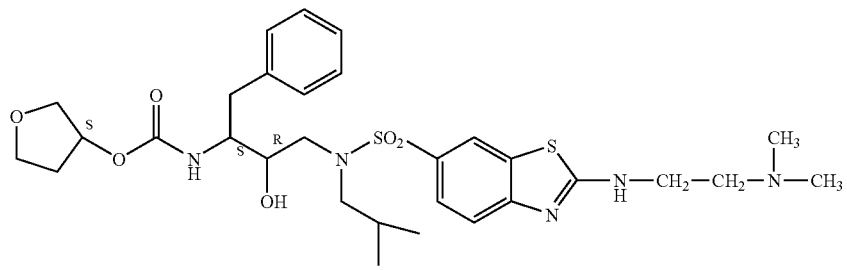

A mixture of 19.66 g of [2R-hydroxy-3-[(2-methylpropyl)amino]-1S-(phenylmethyl)-propyl]-carbamic acid, 1,1-dimethylethyl ester (described in WO97/18205) and 17.76 g of triethylamine in 200 ml of dichloromethane is stirred at 0° C. for 20 minutes under inert atmosphere. 18.72 g of 2-(acetylamino)-6-benzothiazolesulfonyl chloride was added in small portions and the mixture was then stirred at room temperature for 2 hours. After washing with 5% HCl solution, saturated sodium bicarbonate solution and brine, the organic layer was dried and the solvent evaporated under reduced pressure. The crude product was purified on silica gel eluting with 4% methanol in dichloromethane yielding 30.82 g (90%) of intermediate b-4 ($R_2$=H and $R_4$=isobutyl).

To a mixture of 13.75 g of intermediate b-4 ($R_2$=H and $R_4$=isobutyl) in 130 ml of ethanol/dioxane (1:1) 65 ml of HCl (5 to 6 N in isopropanol) was added. The reaction was stirred at 50° C. for 22 hours. After evaporating, the salt was treated with saturated sodium bicarbonate solution and extracted with dichloromethane. The organic layer was dried, the solvent evaporated and the residue purified on silica gel eluting with 3% methanol in dichloromethane yielding 18.36 g (72%) of intermediate b-5 ($R_2$=H and $R_4$=isobutyl).

A solution of 1.81 g of sodium nitrite in 10 ml of water was added over a 40-min period to a mixture of 9.80 g of intermediate b-5 ($R_2$=H and $R_4$=isobutyl) in 180 ml of 85% phosphoric acid held at −10° C. After being stirred for 1.5 hour, the mixture was added to a stirred solution of 10.90 g of copper sulphate pentahydrate and 12.67 g of sodium chloride in 80 ml of water at −10° C. The mixture was stirred for 1.5 hour, being allowed to warm to room temperature, and then made alkaline (pH=8) with an ammonium hydroxide solution under cooling. The resulting solution was extracted with ethylacetate. After drying and evaporating the solvent, 7.59 g (74%) of intermediate b-6 ($R_2$=H and $R_4$=isobutyl) was obtained.

A mixture of 1.63 g of intermediate b-6 ($R_2$=H and F4=isobutyl), 0.80 g of 1-[[[[(3S)-tetrahydro-3-furanyl]oxy]carbonyl]oxy]-2,5-pyrrolidinedione and 0.53 g of triethylamine in 50 ml of dichloromethane was stirred at room temperature for 5 hours. After evaporation of dichloromethane under reduced pressure, the crude product was purified on silica gel eluting with 3% methanol in dichloromethane yielding 0.58 g (29%) of intermediate b-8 ($R_2$=H, $R_4$=isobutyl, $R_1$—L—=[[(3S)-tetrahydro-3-furanyl]oxy]carbonyl).

To a solution of 0.23 g of intermediate b-8 ($R_2$=H, $R_4$=isobutyl, $R_1$—L—=[[(3S)-tetrahydro-3-furanyl]oxy]carbonyl) in 30 ml of acetonitrile was added 0.20 g of N,N-dimethylethylenediamine. This solution was stirred at 80° C. for 4 hours. After evaporation of acetonitrile under reduced pressure, the crude product was purified on silica gel eluting with 2% of methanol in dichloromethane yielding 0.12 g (50%) of compound 56. Mass spectral data: m/z=634 (M+H)

Example 6

Preparation of Compound 44

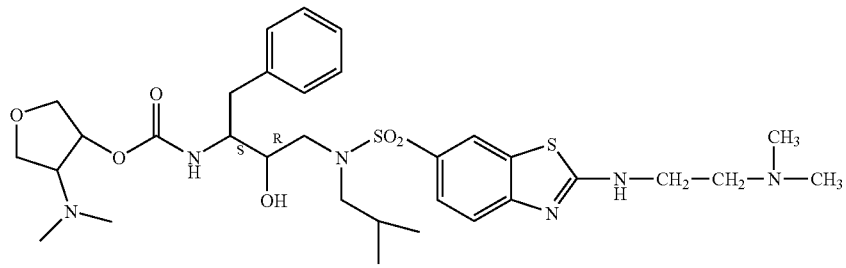

compound 44

To a solution of 0.90 g of intermediate b-6 ($R_2$=H and $R_4$=isobutyl) in 20 ml of acetonitrile was added 0.85 g of N,N-dimethylethylenediamine. This solution was stirred at 80° C. for 3 hours. After evaporation of acetonitrile under reduced pressure, the product was washed with 2% sodium carbonate and extracted with ethylacetate. The organic layer was dried, the solvent evaporated under reduced pressure and purified on silica gel eluting with 1% of ammonia in dichloromethane, yielding 0.57 g (58%) of intermediate b-7 ($R_2$=H, $R_4$=isobutyl and —A—$R_6$=$CH_2CH_2N(CH_3)_2$).

A mixture of 0.65 g of (±trans)-4-(dimethylamino)tetrahydro-3-furanol (synthesis described in U.S. Pat. No. 3,265,711), 3.78 g of disuccinimidyl carbonate and 1.50 g of triethylamine in 30 ml of dichloromethane was stirred at room temperature for 24 hours. After washing the resulting solution with saturated sodium bicarbonate, the organic layer was dried and the solvent evaporated under reduced pressure to give 0.52 g (38%) of (±trans)-1-[[[[4-(dimethylamino)-tetrahydro-furan-3-yl]oxy]-carbonyl]oxy]-2,5-pyrrolidinedione.

A mixture of 0.25 g of intermediate b-7 ($R_1$=H, $R_2$=$CH_2CH_2N(Me)_2$), 0.13 g (±trans)-1-[[[[4-(dimethylamino)-tetrahydro-furan-3-yl]oxy]carbonyl]oxy]-2,5-pyrrolidinedione and 0.07 g of triethylamine in 15 ml of dichloromethane was stirred at room temperature for 24 hours. After evaporation of dichloromethane under reduced pressure, the crude product was purified on silica gel eluting with 4% of ammonia in dichloromethane, yielding 0.14 g (43%) of compound 44. Mass spectral data: m/z=677 (M+H)

Example 7

Preparation of Compound 19

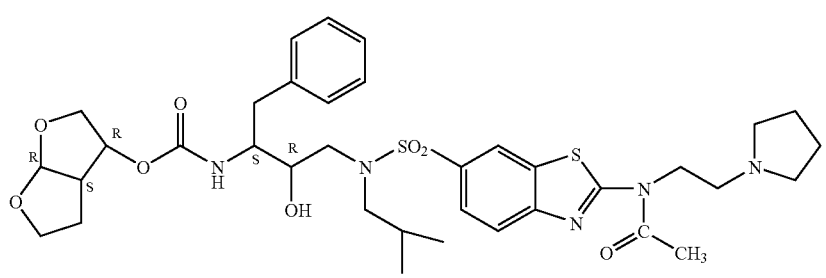
compound 19

To a solution of 0.83 g of intermediate b-6 ($R_2$=H and $R_4$=isobutyl) in 20 ml of acetonitrile was added 0.40 g of N-(2-aminoethyl)-pyrrolidine. This solution was stirred at 80° C. for 4 hours. After evaporation of acetonitrile under reduced pressure, the product was washed with 2% sodium carbonate and extracted with ethylacetate. The organic layer was dried, evaporated under reduced pressure and purified on silica gel eluting with 1% of ammonia in dichloromethane, yielding 0.47 g (49%) of intermediate b-7 ($R_2$=H, $R_4$=isobutyl and —A—$R_6$=$CH_2CH_2$-(1-pyrrolidinyl)).

A mixture of 0.47 g of intermediate b-7 ($R_2$=H, $R_4$=isobutyl and —A—$R_6$=$CH_2CH_2$-(1-pyrrolidinyl)) 0.24 g of 1-[[[[(3R,3aS,6aR)-hexahydrofuro[2,3-b]furan-3-yl]oxy]-carbonyl]oxy]-2,5-pyrrolidinedione and 0.10 g of triethylamine in 20 ml of dichloromethane was stirred at room temperature for 24 hours. After evaporation of dichloromethane under reduced pressure, the crude product was purified on silica gel eluting with 2% of ammonia in dichloromethane, yielding 0.54 g (88%) of intermediate b-9 ($R_2$=H, $R_4$=isobutyl, —A—$R_6$=$CH_2CH_2$-(1-pyrrolidinyl) and —L—$R_1$=[[(3R,3aS,6aR)-hexahydrofuro[2,3-b]furan-3-yl]oxy]carbonyl).

To a solution of 0.54 g of intermediate b-9 ($R_2$=H, $R_4$=isobutyl, —A—$R_6$=$CH_2CH_2$-(1-pyrrolidinyl) and —L—$R_1$=[[(3R,3aS,6aR)-hexahydrofuro[2,3-b]furan-3-yl]oxy]-carbonyl) and 0.16 g of triethylamine in 40 ml of dichloromethane under inert atmosphere was added 0.22 g of acetyl chloride. After stirring at room temperature for 2 hours and washing with water, the organic layer was dried and evaporated under reduced pressure to give 0.50 g (87%) of compound 19. Mass spectral data: m/z=744 (M+H)

Example 8

Preparation of Compound 16

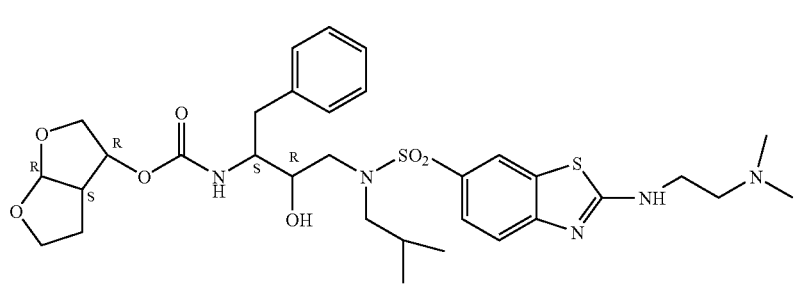
compound 16

To a solution of 4.91 g of [(1S,2R)-3-[[(4-aminophenyl)sulfonyl](2-methylpropyl)-amino]-2-hydroxy-1-(phenylmethyl)propyl]-carbamic acid, 1,1-dimethylethyl ester (prepared as described in U.S. Pat. No. 6,140,505) in 40 ml of anhydrous tetrahydrofuran, was added 1.78 g of 1,1'-thiocarbonyldiimidazole. This solution was refluxed 4 hours. After cooled at 25° C. 0.88 g of N,N-dimethylethylamine was added and then this solution was again refluxed 16 hours. After cooling at 25° C., evaporation of tetrahydrofuran under reduced pressure, dichloromethane was added, washed with water, the organic phase was dried and concentrated. This crude product was purified on silica gel eluting with 5% of methanol in dichloromethane, yielding 3.8 g (62%) of intermediate c-2 ($R_2$=H, $R_4$=isobutyl). Mass spectral data: m/z=622 (M+H), 566, 532.

To a solution of 2.5 g of the intermediate c-2 ($R_2$=H, $R_4$=isobutyl) in 10 ml of acetic acid was added a solution of 0.64 g of bromine in 10 ml acetic acid. After 2 hours, this crude product was concentrated, dichloromethane added and this organic phase washed with a saturated potassium carbonate solution. The organic phase was dried on magnesium sulfate, filtered and concentrated, yielding intermediate c-3 ($R_2$=H, $R_4$=isobutyl). Mass spectral data: m/z=620 (M+H), 564, 520, 261.

The intermediate c-3 ($R_2$=H, $R_4$=isobutyl) was diluted with 20 ml of dichloromethane and 5 ml of trifuoroacetic acid were added. This solution was stirred for 1 hour and then concentrated. This residue was washed with a potassium carbonate solution and extracted with dichloromethane. This crude material was purified on silica gel eluting with 5% of methanol in dichloromethane yielding 1.5 g (72%) of the intermediate c-4 ($R_2$=H, $R_4$=isobutyl).

1.5 g of the intermediate c4 ($R_2$=H, $R_4$=isobutyl), 0.81 g of 1-[[[[(3R,3aS,6aR)-hexahydrofuro[2,3-b]furan-3-yl]oxy]carbonyl]oxy]-2,5-pyrrolidinedione 0.67 g of triethylamine in 5 ml of dichloromethane was stirred for 4 hours at room temperature. This crude product was directly purified on silica gel eluting with 5% methanol in dichloromethane, yielding 0.80 g (39%) of compound 16.

Example 9

Preparation of Compound 27 olesulfonamide and 1.0 g triethylamine in dichioromethane was added 1.47 g 1-[[[[(3R,3aS,6aR)-hexahydrofuro[2,3-b]furan-3-yl]oxy]carbonyl]-oxy]-2,5-pyrrolidinedione. After overnight stirring the reaction mixture was washed with a saturated sodium bicarbonate solution, dried over magnesium sulfate, filtered and concentrated. The obtained residue was purified by column (dichloromethane:methanol 95:5) to afford 2.76 g intermediate d-1 ($R_2$=H, $R_4$=isobutyl, —A—$R_6$=H and —L—$R_1$=[[(3R,3aS,6aR)-hexahydrofuro[2,3-b]furan-3-yl]oxy]carbonyl) (88%).

To a mixture of intermediate d-1 ($R_2$=H, $R_4$=isobutyl, —A—$R_6$=H and —L—$R_1$=[[(3R,3aS,6aR)-hexahydrofuro[2,3-b]furan-3-yl]oxy]carbonyl) (2.0 g; 3.3 mmole) and triethylamine (1.16 g; 11.5 mmole) in dry 1,4-dioxane is added chloroacetylchloride (429 mg; 3.8 mmole). The resulting mixture was stirred at rt for 3 hours. Another portion of chloroacetylchloride (180 mg; 1.5 mmole) was added and stirring was continued for 3 hours. After evaporation of the compound 27

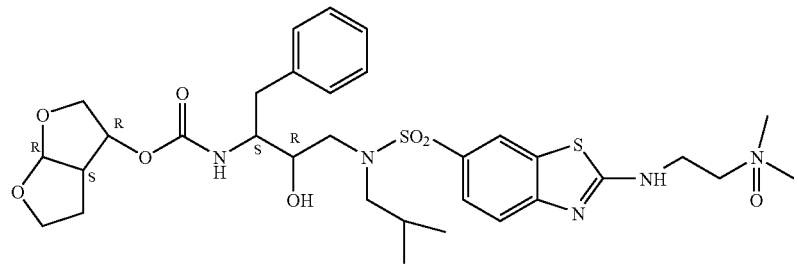

To 0.34 g of compound 16 in 5 ml of dichloromethane was added 0.08 g of sodium bicarbonate and 0.15 g (75%) of meta chloroperbenzoic acid. This solution was stirred 2 hours at room temperature. Water was added and the residue was extracted with dichloromethane. The organic phase was dried on magnesium sulfate, filtered and concentrated. This crude material was purified on silica gel eluting with 5% of methanol in dichloromethane yielding 0.09 g (26%) of compound 27. Mass spectral data: m/z=692 (M+H)

Example 10

Preparation of Compound 11 solvent the residue was purified by chromatography (dichloromethane:methanol 98:2) to afford 1.57 g (70%) of intermediate d-2 ($R_2$=H, $R_4$=isobutyl, —A—$R_6$=H and —L—$R_1$=[[(3R,3aS,6aR)-hexahydrofuro[2,3-b]furan-3-yl]oxy]carbonyl). Mass spectral data: (ES+): 681/683(M+H).

To a solution of the intermediate d-2 ($R_2$=H, $R_4$=isobutyl, —A—$R_6$=H and —L—$R_1$=[[(3R,3aS,6aR)-hexahydrofuro[2,3-b]furan-3-yl]oxy]carbonyl) (0.45 g; 0.66 mmole) in tetrahydrofuran was added 4.6 ml of an 40% wt aqueous dimethylamine solution. After stirring for two hours tetrahydrofuran was evaporated. The aqueous layer was extracted with dichloromethane. The combined organic layers were dried over magnesium sulfate. Concentration in compound 11

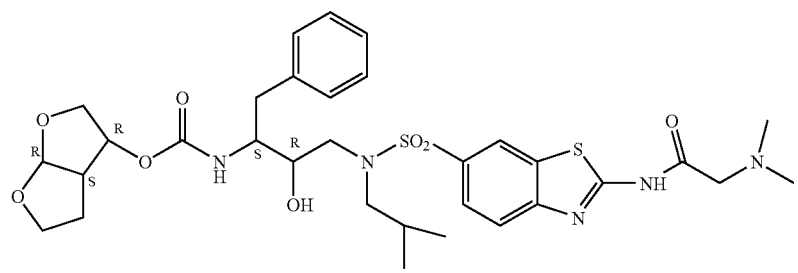

To a mixture of 2.32 g 2-amino-N-[(2R,3S)-3-amino-2-hydroxy-4-phenylbutyl]-N-(2-methylpropyl)-6-benzothiazvacuo yielded 0.42 g (92%) of compound 11. Mass spectral data: (ES+): 690 (M+H), 560.

Example 11

Preparation of Compound 12

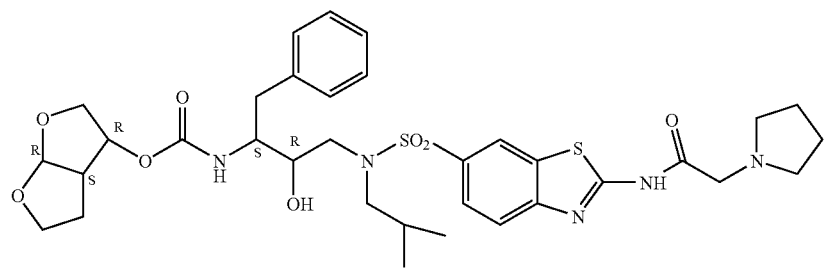
compound 12

To a solution of the intermediate d-2 ($R_2$=H, $R_4$=isobutyl, —A—$R_6$=H and —L—$R_1$=[[(3R,3aS,6aR)-hexahydrofuro[2,3-b]furan-3-yl]oxy]carbonyl) in dichloromethane was 1.5 eq. of pyrrolidine together with sodium carbonate as a base. After overnight stirring at room temperature the solvent was removed in vacuo. The residue was purified by chromatography (dichloromethane:methanol) to yield 76% of compound 12. Mass spectral data: (ES+) 715 (M+H)

Example 12

Preparation of Compound 43

A mixture of 6.13 g of intermediate e-1 ($R_2$=H, $R_4$=isobutyl and —A—$R_6$=H) and 10 g sodium carbonate in water/dioxane (1/2) was heated to 80° C. for 48 hours. Dioxane was removed in vacuo. The resulting aqueous phase was extracted twice with ethyl acetate. After drying over magnesium sulfate and filtration the combined organic phase was concentrated to yield 5.08 g of intermediate e-2 ($R_2$=H, $R_4$=isobutyl and —A—$R_6$=H). Mass spectral data (ES+): 549(M+H), 449.

To a mixture of 3.0 g 2-aminobenzothiazole intermediate e-2 ($R_2$=H, $R_4$=isobutyl and —A—$R_6$=H) and 1.1 g triethylamine in dry 1,4-dioxane was added 0.77 g chloroacetylchloride. The resulting mixture was stirred overnight. After evaporation of the solvent the residue was purified by chromatography (dichloromethane:methanol 98:2) to afford 2.7 g (78%) of intermediate e-3 ($R_2$=H, $R_4$=isobutyl and —A—$R_6$=H). Mass spectral data (ES+): 625/627(M+H).

To a solution of 0.8 g intermediate e-3 ($R_2$=H, $R_4$=isobutyl and —A—$R_6$=H) in tetrahydrofuran was added 8 ml of an 40% wt aqueous dimethylamine solution. After stirring for three hours tetrahydrofuran was evaporated. The aqueous layer was extracted with dichloromethane. The combined organic layers were dried over magnesium sulfate. Concentration in vacuo provided 0.58 g (85%) of intermediate e-4 ($R_2$=H, $R_4$=isobutyl, —A—$R_6$=H and $R_a$=$R_b$=$CH_3$). Mass spectral data (ES+): 634(M+H), 534.

To a solution of intermediate e-4 ($R_2$=H, $R_4$=isobutyl, —A—$R_6$=H and $R_a$=$R_b$=$CH_3$) in dichloromethane was

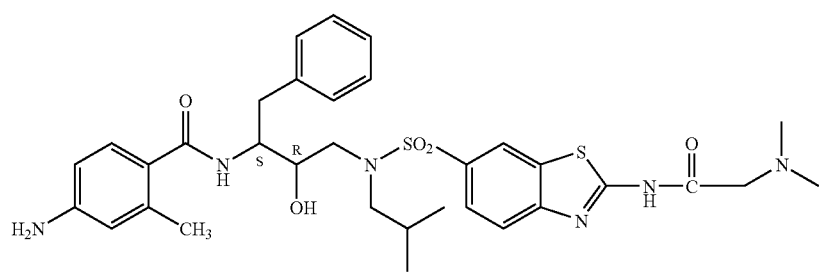
compound 43 added trifluoracetic acid (10 equivalents). After overnight stirring the organic phase was washed with saturated sodium bicarbonate and brine, dried over magnesium sulfate, filtered and concentrated to afford the intermediate e-5 ($R_2$=H, $R_4$=isobutyl, —A—$R_6$=H and $R_a$=$R_b$=$CH_3$).

To a solution of 0.35 g 4-amino-2-methylbenzoic acid in dichloromethane was added at 0° C. 0.09 g 1-hydroxybenzotriazole and 0.13 g EDC. After one half hour of stirring the temperature was allowed to rise to room temperature and stirring was continued for one more hour. After addition of the intermediate e-5 ($R_2$=H, $R_4$=isobutyl, —A—$R_6$=H and $R_a$=$R_b$=$CH_3$) the reaction mixture was stirred at room temperature for two days. Then the solvent was removed in vacuo and the obtained residue was purified by chromatography (dichloromethane:methanol 97:3) to afford 0.12 g (29%) of compound 43. Mass spectral data (ES+): 667(M+H).

Example 13

Preparation of the Intermediate f-2 ($R_2$=H and $R_4$=—$CH_2$-(2-pyridinyl))

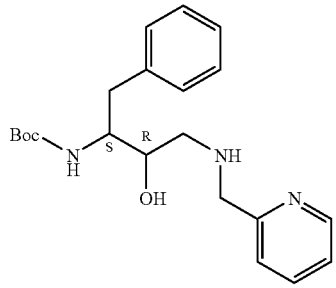

25 g of 2-pyridylmethylamine was stirred at reflux in 400 ml of isopropanol. Then a solution of 21 g of the 2S,3S-1,2-epoxy-3-(tert-butoxycarbonylamino)-4-phenylbutane, commercially available, in 200 ml of isopropanol was added dropwise. The reaction mixture was stirred overnight at reflux. After evaporation of the solvent, the residue was redissolved in dichloromethane and washed 4 times with water. The organic layer was dried and evaporated. The residue obtained was purified by chromatography (dichloromethane: 7N $NH_3$ in methanol, 98:2) to afford 24 g (84%) of intermediate f-2 ($R_2$=H and $R_4$=—$CH_2$-(2-pyridinyl)).

Example 14

Preparation of Compound 20

Compound 20 may also be prepared according to the method depicted in scheme G. The specific method is illustrated hereunder in scheme I.

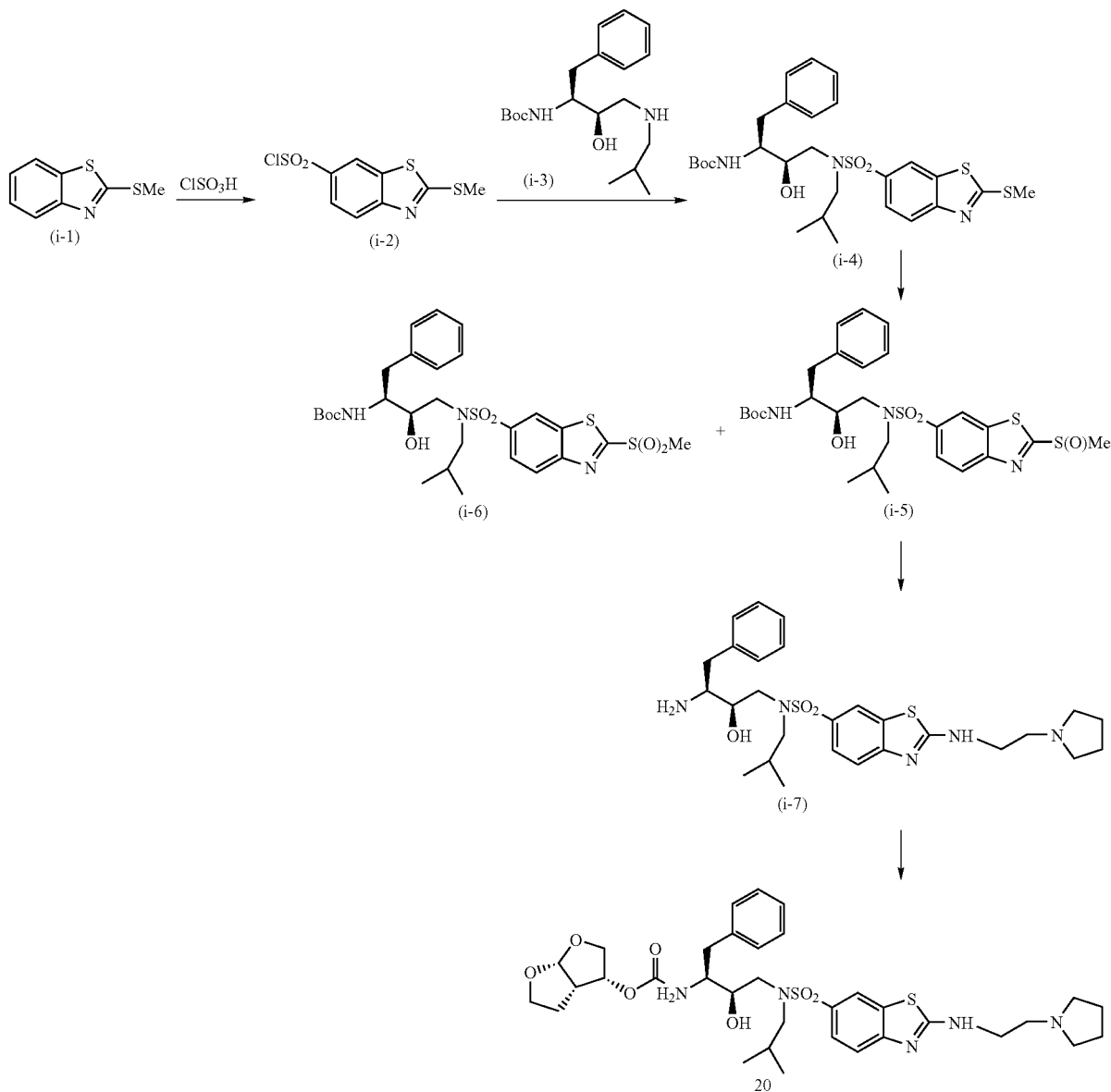

Chlorosulfonic acid (0.193 kg; 1.65 mol) was stirred at 10° C. under nitrogen. i-1 was added carefully. The reaction mixture was stirred for 3 hours at 90° C. The heating was stopped and thionylchloride (0.079 kg; 0.66 mol) was added slowly. The reaction mixture was stirred for another hour at 90° C. The reaction mixture was cooled until 35° C. and then 200 ml ethylacetate was added slowly. Another 200 ml of ethylacetate was added quickly after the beginning of the product precipitation. The precipitate was filtered and washed twice with 200 ml ethylacetate and twice with 1000 ml cold water. The precipitate was then stirred in a $NaHCO_3$ solution until pH=7. This mixture was filtered and the white solid i-2 was dried in a vacuum oven at 50° C. (0.123 kg, 80%). (LC/MS $MW^+$; 280, 282)

A mixture of 0.120 kg (0.36 mol) of intermediate i-3 and 0.073 kg (0.72 mol) of triethylamine in 2-methyltetrahydrofuran (1.150 kg) was stirred at 35° C. until dissolution of the reactants. Then 0.100 kg (0.36 mol) of intermediate i-2 was added and the reaction mixture was stirred for 1.5 hours at 55° C. After washing the reaction mixture with water (0.500 kg), the organic layer was separated and washed with 0.500 kg 1.5 N HCl solution. Then the organic layer was separated, dried and evaporated yielding i-4; 0.208 kg (100%). (LC/MS $MW^+$; 480, 481, 482)

0.208 kg (0.36 mol) of intermediate i-4 was stirred in a mixture of 1 kg 2-methyltetrahydrofuran, 0.060 kg $H_2O$ and 0.110 kg ethanol at 40° C. until dissolution of all the reactants. Then magnesium monoperoxyphtalate hexahydrate 0.200 kg (0.4 mol) was added. The mixture was stirred and heated for 15 min at 60° C. The reaction mixture was made alkaline with 0.400 kg $Na_2CO_3$ until pH=10. Intermediates i-5 and i-6. (about 70% i-5 and 30% i-6). (LC/MS $MW^+$i-5; 496, 497, 498 $MW^+$i-6; 511, 513) To this reaction mixture was added at 60° C. 0.050 kg (0.43 mol) N-(2-aminoethylpyrrolidine. This mixture was stirred for 20 hours at 70° C. Then the slurry was cooled to 40° C. and HCl concentrated (12 N) was added dropwise until pH=7-8. A phase precipitation was then observed. The organic layer was separated, evaporated and dried in the vacuum oven at 50° C. yielding Boc N-protected i-7; 0.217 kg (93%). (LC/MS $MW^+$; 646, 647, 648)

0.217 kg (0.36 mol) of intermediate Boc N-protected i-7 was dissolved in 1.4 kg isopropanol at 50° C. Then 0.370 L HCl 5 à 6 N (2 mol) was added and the mixture was heated and stirred for 2.5 hours at 70° C. This hot reaction mixture was added dropwise to 0.50 kg cold (0° C.-15° C.) isopropanol. The precipitate was filtered and washed with diisopropyl ether. The slightly brown solid was triturated in a DIPE/toluene (50/50) mixture and then filtered and dried in the vacuum oven at 50° C., yielding 0.170 kg (76%) of i-7 HCl-salt. (LC/MS $MW^+$; 546, 547, 548).

A mixture of 1.3 g of intermediate i-7, 0.774 g of 1-[[[[(3S,3aR,6aS)+(3R,3aS,6R)-hexahydrofuro[2,3-b]furan-3-yl]oxy]carbonyl]oxy]-2,5-pyrrolidinedione (prepared analogously to the procedure described in WO9967417) and 0.33 g of triethylamine in 100 ml of dichloromethane was stirred at room temperature for 24 hours. This crude product was washed with NaHCO3 solution. The organic layer was dried and the solvent evaporated under reduced pressure. The residue was purified on silica gel, yielding 0.74 g (45%) of compound 20. Mass spectra data: m/z=702(M+H).

Example 15

Preparation of the Compound 85 and its Intermediates $R_1$=isobutyl

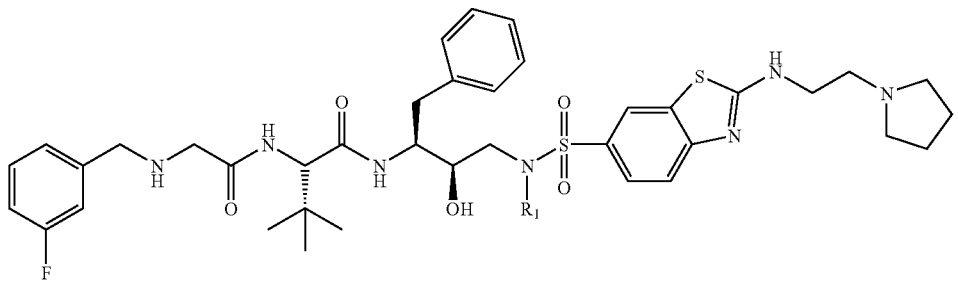

This compound was prepared following the procedure depicted in scheme H.

11 g of intermediate h-1 (PG=Boc, $R_1$=isobutyl) [(1S,2R)-2-hydroxy-3-[(2-methylpropyl)[[2-(methylthio)-benzothiazol-6-yl]sulfonyl]amino]-1-(phenyl methyl)propyl]carbamic acid, 1,1-dimethylethyl ester were dissolved in 300 mL of HCl in isopropanol and 100 mL of dichloromethane and the solution was stirred at room temperature overnight. The reaction mixture was then concentrated and treated with a mixture of dichloromethane and sodium hydroxide in water. The organic layer was then dried over $MgSO_4$ and evaporated to give 8.8 g (97%) of the deprotected intermediate N-[(2R,3S)-3-amino-2-hydroxy-4-phenylbutyl]-N-(2-methylpropyl)[2-(methylthio)-benzothiazol-6-yl]sulfonamide, as a free base. Mass spectral data: m/z=480 (M+H).

4.15 g of the previous intermediate, 2 g of Boc-L-tert-Leucine, 1.17 g of HOBt and 1.66 g of EDC were dissolved in 150 mL of dichloromethane and stirred at room temperature overnight. The reaction mixture was then successively washed with a solution of NaHCO3 in water, brine, dried over $MgSO_4$ and evaporated to give 6 g (100%) of intermediate h-2 [(1S)-1-[[[(1S,2R)-2-hydroxy-3-[(2-methylpropyl)[(2-(methylthio)-benzothiazol-6-yl)sulfonyl]amino]-1-(phenylmethyl)propyl]amino]-carbonyl]-2,2-dimethylpropyl]carbamic acid, 1,1-dimethylethyl ester. Mass spectral data: m/z=693 (M+H).

6 g of intermediate h-2 were dissolved in 100 mL of HCl in isopropanol, and stirred at room temperature during 2 h. The reaction mixture was then concentrated and treated with a mixture of dichloromethane and a solution of sodium carbonate in water. The organic phase was then washed with brine, dried over $MgSO_4$ and evaporated to give 3.9 g (76%) of the deprotected intermediate as a free base. Mass spectral data: m/z=593 (M+H).

3.9 g of the previous intermediate, 0.69 g of chloroacetic acid, 0.98 g of HOBt, and 1.38 g of EDC were dissolved in 100 mL of dichloromethane and stirred at RT overnight. The reaction mixture was then washed with brine, dried over MgSO$_4$ and evaporated. The crude compound was purified on silica gel eluting with 0 to 5% methanol in dichloromethane, yielding 3.72 g (85%) of the desired intermediate h-3 2-[(chloroacetyl)amino]-3,3-dimethyl-N-[(1S,2R)-2-hydroxy-3-[(2-methylpropyl)[[2-(methylthio)-benzothiazol-6-yl]sulfonyl]amino]-1-(phenylmethyl)propyl]-(2S)-butanamide. Mass spectral data: m/z=669 (M+H).

3.72 g of intermediate h-3 and 1.27 mL of meta-fluorobenzylamine were dissolved in DMF and stirred at 60° C. during 2 h. The reaction mixture was then concentrated and treated with a mixture of dichloromethane and a solution of sodium carbonate in water.

The organic phase was then dried over MgSO$_4$ and evaporated to yield 4.3 g (100%) of the desired intermediate N'-[(3-fluorophenyl)methyl]glycyl-N-[(1S,2R)-2-hydroxy-3-[(2-methylpropyl)[[2-(methylthio)benzothiazol-6-yl]sulfonyl]amino]-1-(phenylmethyl)propyl]-3-methyl-L-Valinamide. Mass spectral data: m/z=758 (M+H).

4.2 g of the previous intermediate, 1.2 g of Boc$_2$O and 0.77 mL of triethylamine were dissolved in 50 mL of dichloromethane. The reaction mixture was stirred overnight at room temperature and 1.2 g of Boc$_2$O were added. After 5 h, the reaction mixture was successively washed with a solution of sodium carbonate in water, brine, dried over MgSO$_4$ and evaporated. The crude compound was purified on silica gel eluting with 2 to 5% methanol in dichloromethane, yielding 3.2 g (67%) of the desired intermediate h-4 N'-[(1,1-dimethylethoxy)carbonyl]-N'-[(3-fluorophenyl)methyl]glycyl-N-[(1S,2R)-2-hydroxy-3-[(2-methylpropyl)[[2-(methylthio)benzothiazol-6-yl]sulfonyl]amino]-1-(phenylmethyl)propyl]-3-methyl-L-Valinamide. Mass spectral data: m/z=858 (M+H).

3.2 g of intermediate h-4 and 0.92 g of meta-chloroperoxybenzoic acid (mCPBA) were reacted in 100 mL of dichloromethane, at room temperature, during 1 h30. The reaction mixture was then washed with a solution of sodium carbonate in water, dried over MgSO$_4$ and evaporated to yield 3.45 g (100%) of the desired intermediate h-5 N'-[(1,1-dimethylethoxy)carbonyl]-N'-[(3-fluorophenyl)methyl]glycyl-N-[(1S,2R)-2-hydroxy-3-[(2-methylpropyl)[[2-(methylsulfinyl)benzothiazol-6-yl]sulfonyl]amino]-1-(phenylmethyl)propyl]-3-methyl-L-Valinamide. Mass spectral data: m/z=874 (M+H).

0.5 g of intermediate h-5 was reacted with 0.16 mL of N-(2-aminoethyl)pyrrolidine in 10 mL of acetonitrile, at 60° C., during 1 h 30. The reaction mixture was then evaporated and purified on silica gel eluting with 5 to 10% methanol in dichloromethane, yielding 0.24 g (46%) of the desired intermediate N'-[(1,1-dimethylethoxy)carbonyl]-N'-[(3-fluorophenyl)methyl]glycyl-N-[(1S,2R)-2-hydroxy-3-[(2-methylpropyl)[[2-[2-(pyrrolidin-1-yl)ethylamino]benzothiazol-6-yl]sulfonyl]amino]-1-(phenylmethyl)propyl]-3-methyl-L-Valinamide. Mass spectral data: m/z=924 (M+H).

0.15 g of the previous intermediate was dissolved in 5 mL of HCl in isopropanol. The reaction mixture was stirred at room temperature during 2 h, then evaporated. The crude compound was purified by preparative HPLC, yielding 60 mg of the desired final compound 85 N'-[(3-fluorophenyl)methyl]glycyl-N-[(1S,2R)-2-hydroxy-3-[(2-methylpropyl)[[2-[2-(pyrrolidin-1-yl)ethylamino]benzothiazol-6-yl]sulfonyl]amino]-1-(phenylmethyl)propyl]-3-methyl-L-Valinamide, bis-trifluoroacetate, obtained as a TFA salt. Mass spectral data: m/z=824 (M+H).

Example 16

Preparation of the Compound 86R$_1$=isobutyl)

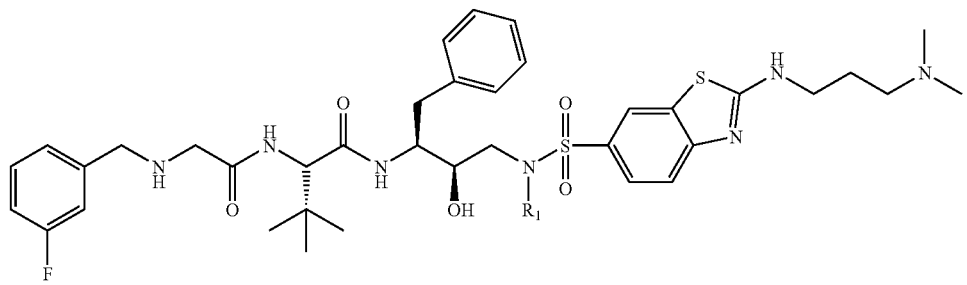

0.5 g of intermediate h-5 was reacted with 0.16 mL of 3-(dimethylamino)propylamine in 10 mL of acetonitrile, at 60° C., during 2 h. The reaction mixture was then evaporated, yielding 0.54 g (100%) of the desired intermediate N'-[(1,1-dimethylethoxy)carbonyl]-N'-[(3-fluorophenyl)methyl]glycyl-N-[(1S,2R)-2-hydroxy-3-[[[2-[3-(dimethylamino)propylamino]benzothiazol-6-yl]sulfonyl](2-methylpropyl)amino]-1-(phenylmethyl)propyl]-3-methyl-L-Valinamide. Mass spectral data: m/z=912 (M+H).

0.54 g of the previous intermediate was dissolved in 10 mL of HCl in isopropanol. The reaction mixture was stirred at room temperature during 2 h, then evaporated. The crude compound was purified by preparative HPLC, yielding 83 mg of the desired final compound 86 N'-[(3-fluorophenyl)methyl]glycyl-N-[(1S,2R)-2-hydroxy-3-[[[2-[3-(dimethylamino)propylamino]benzothiazol-6-yl]sulfonyl](2-methylpropyl)amino]-1-(phenylmethyl)propyl]-3-methyl-L-Valinamide, bis-trifluoroacetate, obtained as a TFA salt. Mass spectral data: m/z=812 (M+H).

Example 17

Preparation of the Compounds 87 ($R_1$=isobutyl)

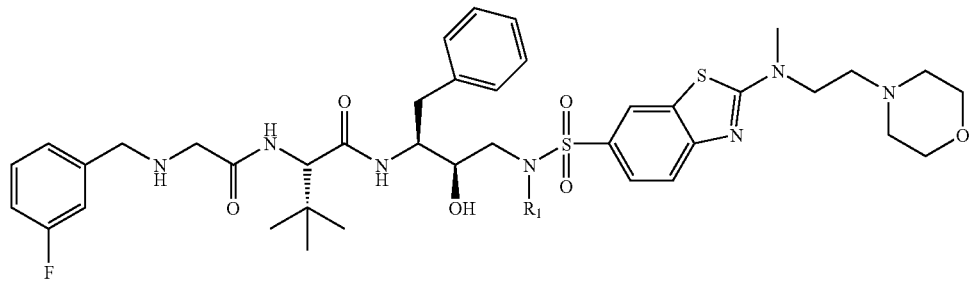

0.5 g of intermediate h-5 was reacted with 0.18 mg of N-methyl, N-(2-morpholin-4-ylethyl)amine in 10 mL of acetonitrile, at 60° C., overnight. 0.9 g of N-methyl, N-(2-morpholin-4-ylethyl)amine was then added again to the reaction mixture, which was further stirred during two days. The reaction mixture was then evaporated and purified on silica gel eluting with 5% methanol in dichloromethane, yielding 0.6 g (100%) of the desired intermediate N'-[(1,1-dimethylethoxy)carbonyl]-N'-[(3-fluorophenyl)methyl]glycyl-N-[(1S,2R)-2-hydroxy-3-[[[2-[N-methyl, N-(2-morpholin-4-ylethyl) amino]benzothiazol-6-yl]sulfonyl](2-methylpropyl) amino]-1-(pheriylmethyl)propyl]-3-methyl-L-Valinamide. Mass spectral data: m/z=954 (M+H).

0.6 g of the previous intermediate was dissolved in 100 mL of HCl in isopropanol. The reaction mixture was stirred at room temperature during 2 h, then evaporated and treated with a mixture of dichloromethane and a solution of sodium carbonate in water. The organic phase was then dried over $MgSO_4$ and evaporated. The crude compound was purified by preparative HPLC, yielding 424 mg (60%) of the desired final compound 87 N'-[(3-fluorophenyl)methyl]glycyl-N-[(1S, 2R)-2-hydroxy-3-[[[2-[N-methyl, N-(2-morpholin-4-ylethyl)amino]benzothiazol-6-yl]sulfonyl](2-methylpropyl) amino]-1-(phenylmethyl)propyl]-3-methyl-L-Valinamide, bis-trifluoroacetate, obtained as a TFA salt. Mass spectral data: m/z=854 (M+H).

The following tables list the compounds of formula (I) which were prepared following one of the above reaction schemes.

TABLE 1

| Co. No. | Scheme | $R_a$ | salt form/stereochemistry of bicyclic ring |
|---|---|---|---|
| 1 | A | —NH—CO—$CH_3$ | free base/(3R,3aS,6aR) + (3S,3aR,6aS) |
| 2 | A | —NH—COO—$C_2H_5$ | free base/(3R,3aS,6aR) + (3S,3aR,6aS) |
| 3 | D | —NH—CO—$CH_2$—$N(CH_3)_2$ | free base/(3R,3aS,6aR) + (3S,3aR,6aS) |
| 4 | B | —NH—$(CH_2)_2$—$N(CH_3)_2$ | free base/(3R,3aS,6aR) + (3S,3aR,6aS) |
| 5 | D | piperazinyl-acetamide | free base/(3R,3aS,6aR) + (3S,3aR,6aS) |
| 6 | D | —NH—$CH_2$—$COOCH_3$ | free base/(3R,3aS,6aR) + (3S,3aR,6aS) |
| 7 | D | pyrrolidinyl-acetamide | free base/(3R,3aS,6aR) + (3S,3aR,6aS) |

TABLE 1-continued

| Co. No. | Scheme | $R_a$ | salt form/stereochemistry of bicyclic ring |
|---|---|---|---|
| 8 | D | —NH—CO—CH₂—N(pyrrolidine) | HCl (1:1)/(3R,3aS,6aR) + (3S,3aR,6aS) |
| 9 | A | —N(CH₃)—COCH₃ | free base/(3R,3aS,6aR) + (3S,3aR,6aS) |
| 10 | D | —NH—CO—CH₂—N(morpholine) | free base/(3R,3aS,6aR) + (3S,3aR,6aS) |
| 11 | D | —NH—CO—CH₂—N(CH₃)₂ | free base/(3R,3aS,6aR) |
| 12 | D | —NH—CO—CH₂—N(pyrrolidine) | free base/(3R,3aS,6aR) |
| 13 | D | —NH—CO—CH₂—N(pyrrolidine) | fumarate (1:1)/(3R,3aS,6aR) |
| 14 | D | —NH—CO—CH₂—N(pyrrolidine) | HCl (1:1)/(3R,3aS,6aR) |
| 15 | D | —NH—CO—CH₂—N(pyrrolidine) | oxalate (1:1)/(3R,3aS,6aR) |
| 16 | C | —NH—(CH₂)₂—(CH₃)₂ | free base/(3R,3aS,6aR) |
| 17 | D | —NH—CO—CH₂—N(piperazine-NH) | free base/(3R,3aS,6aR) |
| 18 | B | —N(COCH₃)—(CH₂)₃—N(CH₃)₂ | free base/(3R,3aS,6aR) |
| 19 | B | —N(COCH₃)—(CH₂)₂—N(pyrrolidine) | free base/(3R,3aS,6aR) |
| 20 | B | —NH—(CH₂)₂—N(pyrrolidine) | free base/(3R,3aS,6aR) |

TABLE 1-continued
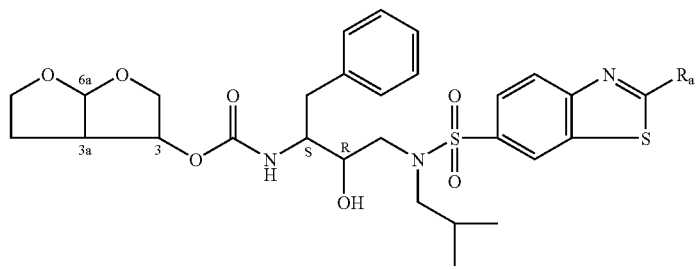
| Co. No. | Scheme | $R_a$ | salt form/stereochemistry of bicyclic ring |
|---|---|---|---|
| 21 | B | 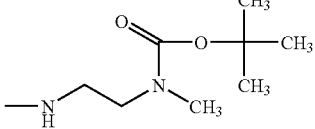 | free base/(3R,3aS,6aR) |
| 22 | B | —NH—(CH$_2$)$_3$—N(CH$_3$)$_2$ | free base/(3R,3aS,6aR) |
| 23 | B | —NH—(CH$_2$)$_2$—NH(CH$_3$) | free base/(3R,3aS,6aR) |
| 24 | B | 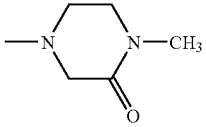 | free base/(3R,3aS,6aR) |
| 25 | B | 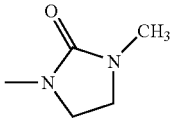 | free base/(3R,3aS,6aR) |
| 26 | B | 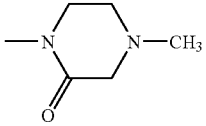 | free base/(3R,3aS,6aR) |
| 27 | C | 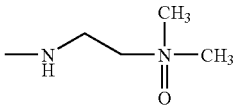 | free base/(3R,3aS,6aR) |
| 28 | B | 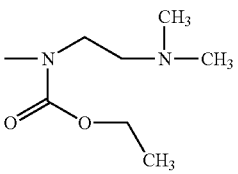 | free base/(3R,3aS,6aR) |

TABLE 2

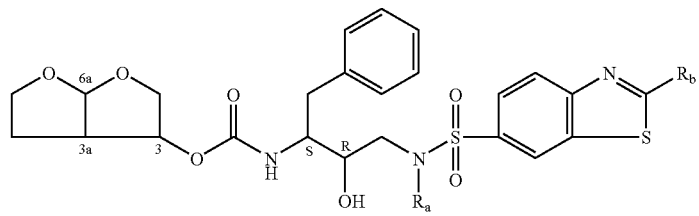

| Co. No. | Scheme | $R_a$ | $R_b$ | Salt/stereochemistry of bicyclic ring |
|---|---|---|---|---|
| 29 | A | —(CH$_2$)$_2$—NH—(2-pyridinyl) | —N—CO—CH$_3$ | free base/ (3R,3aS,6aR) + (3S,3aR,6aS) |

TABLE 3

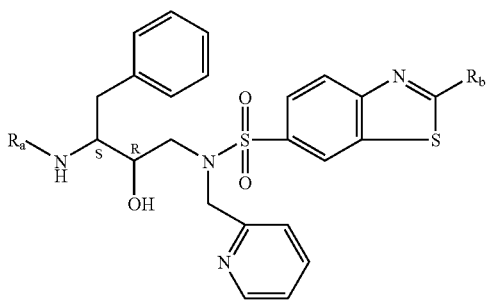

| Co. No. | Scheme | $R_a$ | $R_b$ | Salt/stereochemistry in $R_a$ group |
|---|---|---|---|---|
| 30 | D | ![2,6-dimethylphenoxy-CH2-CO-NH-CO-CH2-O-2,6-dimethylphenyl] | | free base/— |
| 31 | A | ![2,6-dimethylphenoxy-CH2-CO-] | —N(CH$_3$)—CO—CH$_3$ | free base/— |
| 32 | A | ![2,6-dimethylphenoxy-CH2-CO-] | —N(CH$_3$)—CO—CH$_3$ | trifluoroacetate (1:1)/— |
| 33 | A | ![bicyclic furofuran acetate] | —N(CH$_3$)—CO—CH$_3$ | free base/ (3R,3aS,6aR) + (3S,3aR,6aS) |

TABLE 4
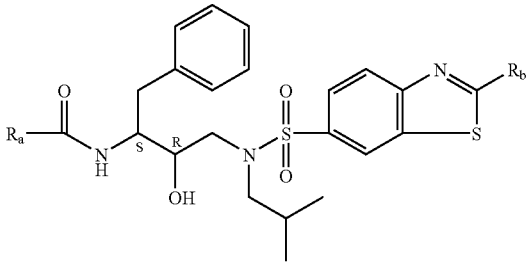
| Co. No. | Scheme | Ra | Rb | Salt/stereochemistry in Ra group |
|---|---|---|---|---|
| 34 | D | 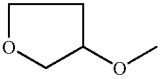 | —NH—CO—CH$_2$—N(CH$_3$)$_2$ | free base/3S |
| 35 | D | 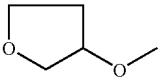 | 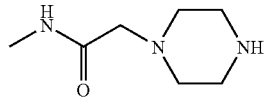 | free base/3S |
| 36 | D | 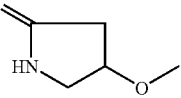 | —NH—CO—CH$_2$—N(CH$_3$)$_2$ | free base/3S |
| 37 | E | 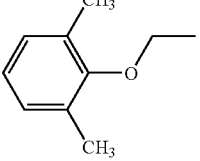 | 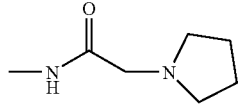 | free base/— |
| 38 | B | 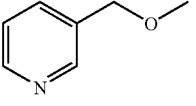 | —NH—(CH$_2$)$_2$—N(CH$_3$)$_2$ | free base/— |
| 39 | B | 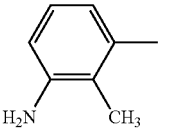 | —NH—(CH$_2$)$_2$—N(CH$_3$)$_2$ | free base/— |
| 40 | B | 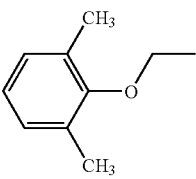 | —NH—(CH$_2$)$_2$—N(CH$_3$)$_2$ | free base/— |
| 41 | B | 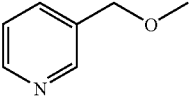 | 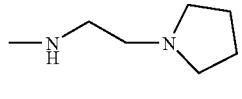 | free base/— |
| 42 | D | 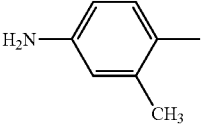 | 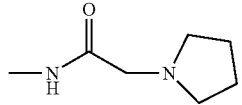 | free base/— |

TABLE 4-continued
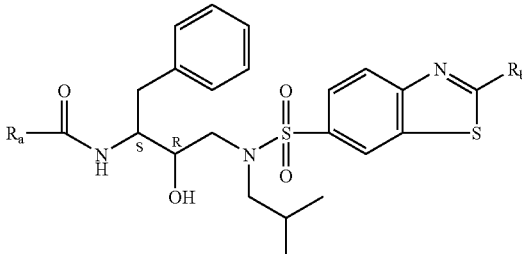
| Co. No. | Scheme | R$_a$ | R$_b$ | Salt/stereochemistry in R$_a$ group |
|---|---|---|---|---|
| 43 | D | 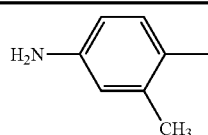 | —NH—CO—CH$_2$—N(CH$_3$)$_2$ | free base/— |
| 44 | B | 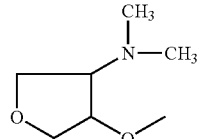 | —NH—(CH$_2$)$_2$—N(CH$_3$)$_2$ | free base/± trans |
| 45 | B | 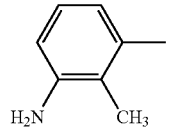 | 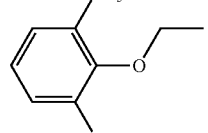 | free base/— |
| 46 | B | 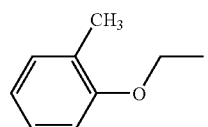 | 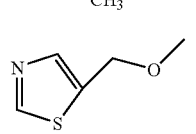 | free base/— |
| 47 | B | 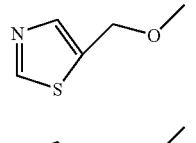 | 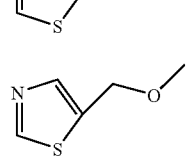 | trifluoroacetate (1:1)/— |
| 48 | B |  | —NH—(CH$_2$)$_2$—N(CH$_3$)$_2$ | free base/— |
| 49 | B |  | 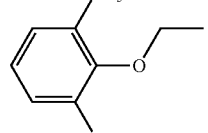 | free base/— |
| 50 | B |  | 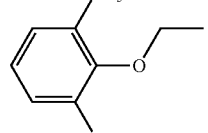 | trifluoroacetate (1:1)/— |
| 51 | B |  | —NH—(CH$_2$)$_3$—N(CH$_3$)$_2$ | free base/— |

TABLE 4-continued
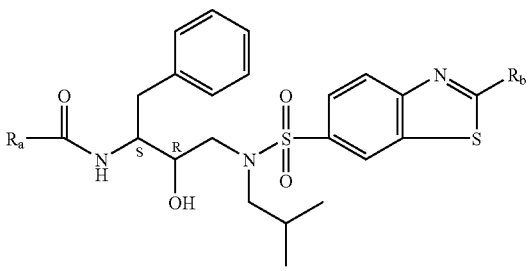
| Co. No. | Scheme | Rₐ | R_b | Salt/stereochemistry in Rₐ group |
|---|---|---|---|---|
| 52 | B | 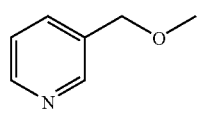 | —NH—(CH₂)₃—N(CH₃)₂ | free base/— |
| 53 | B | 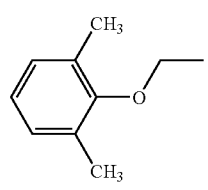 | —NH—(CH₂)₃—N(CH₃)₂ | free base/— |
| 54 | B | 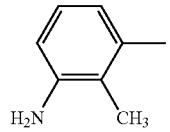 | —NH—(CH₂)₃—N(CH₃)₂ | free base/— |
| 55 | B | H | 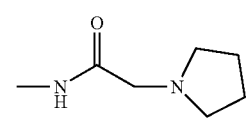 | free base/— |
| 56 | B | 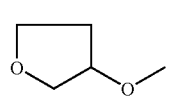 | —NH—(CH₂)₂—N(CH₃)₂ | free base/3S |
| 57 | B | 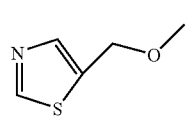 | 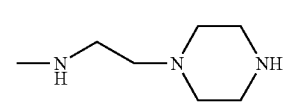 | free base/— |
| 58 | B | 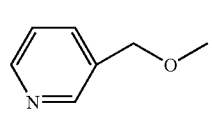 | 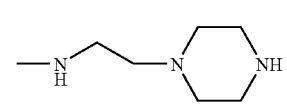 | free base/— |
| 59 | B | 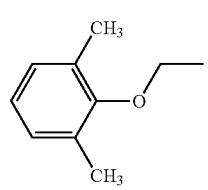 | 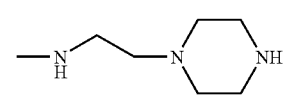 | free base/— |
| 60 | B | 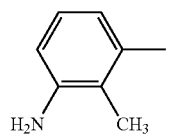 | 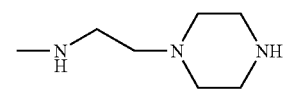 | free base/— |

TABLE 4-continued
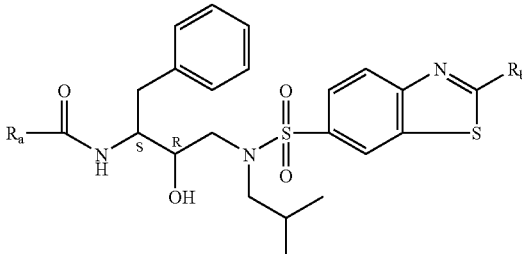
| Co. No. | Scheme | $R_a$ | $R_b$ | Salt/stereochemistry in $R_a$ group |
|---|---|---|---|---|
| 61 | D | 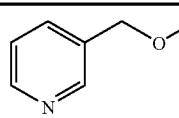 | 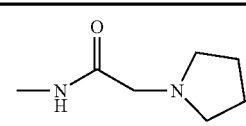 | free base/— |
| 62 | D | 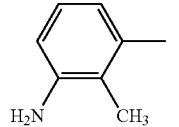 | 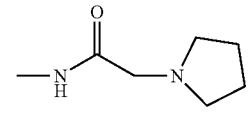 | free base/— |
| 63 | B | 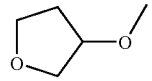 | 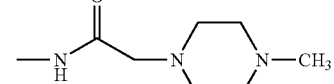 | free base/3S |
| 64 | B | 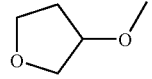 | 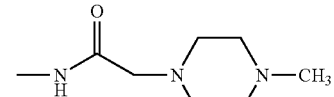 | Trifluoroacetate (1:1)/3S |
| 65 | B | 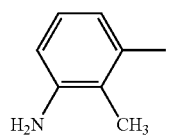 | 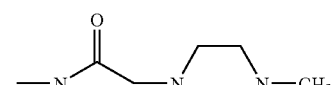 | free base/— |
| 66 | B | 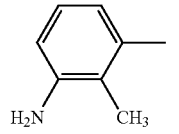 | 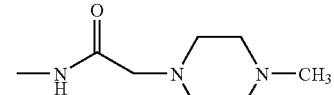 | Trifluoroacetate (1:1)/— |
| 67 | B | 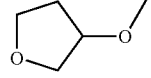 | 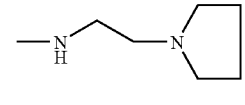 | free base/3S |
| 68 | B | 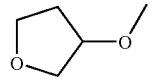 | 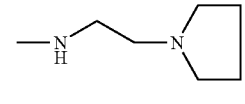 | Trifluoroacetate (1:1)/3S |
| 69 | B | 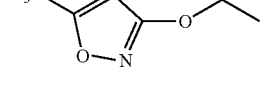 | 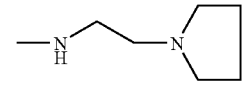 | free base/— |
| 70 | E | 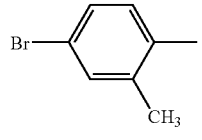 | 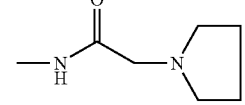 | free base/— |

TABLE 4-continued
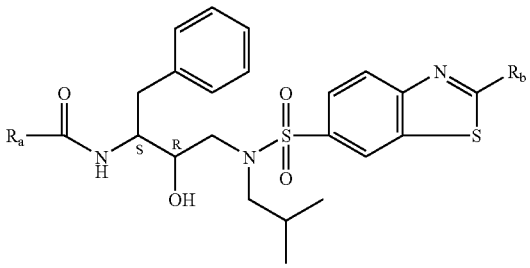
| Co. No. | Scheme | $R_a$ | $R_b$ | Salt/stereochemistry in $R_a$ group |
|---|---|---|---|---|
| 71 | B | 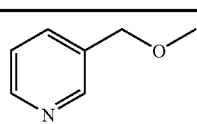 | 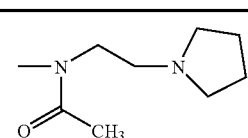 | free base/— |
| 72 | A | 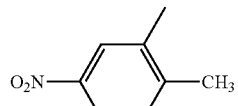 | —NH—CO—CH₃ | free base/— |
| 73 | A | 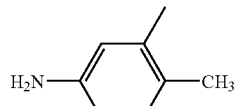 | —NH—CO—CH₃ | free base/— |
| 74 | A | 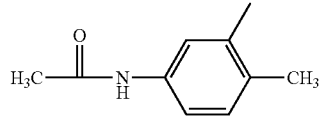 | —NH—CO—CH₃ | free base/— |
| 75 | E | 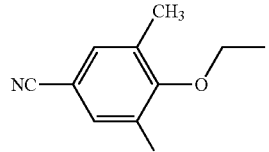 | 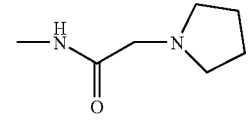 | free base/— |
| 76 | A | 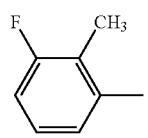 | 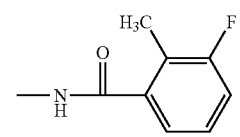 | free base/— |
| 77 | A | 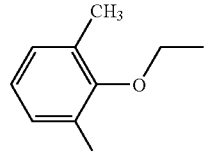 | —N(CH₃)—CO—CH₃ | free base/— |
| 78 | B | 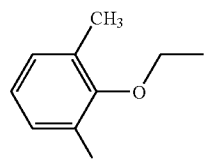 | 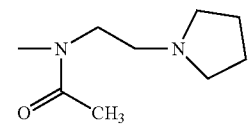 | free base/— |

TABLE 4-continued
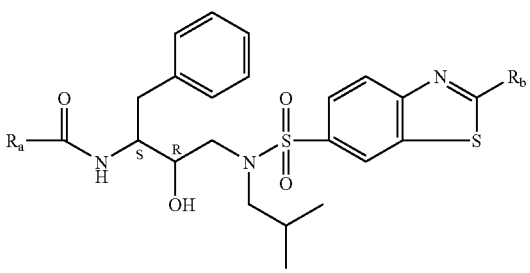
| Co. No. | Scheme | $R_a$ | $R_b$ | Salt/stereochemistry in $R_a$ group |
|---|---|---|---|---|
| 79 | A | 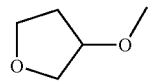 | —N(CH$_3$)—CO—CH$_3$ | free base/3S |
| 80 | A | 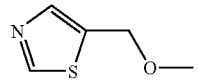 | —N(CH$_3$)—CO—CH$_3$ | free base/— |
| 81 | A | 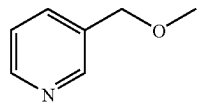 | —N(CH$_3$)—CO—CH$_3$ | free base/— |
| 82 | A | 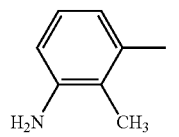 | —N(CH$_3$)—CO—CH$_3$ | free base/— |
| 83 | A | 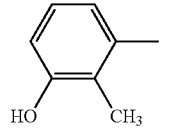 | —N(CH$_3$)—CO—CH$_3$ | free base/— |
| 84 | A | 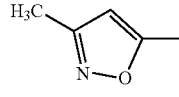 | —NH—CO—CH$_3$ | free base/— |
TABLE 5
| Co | Structure |
|---|---|
| 04 | 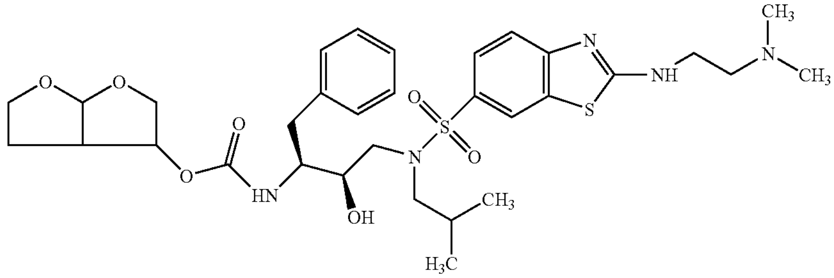 |

TABLE 5-continued
| Co | Structure |
|---|---|
| 16 | 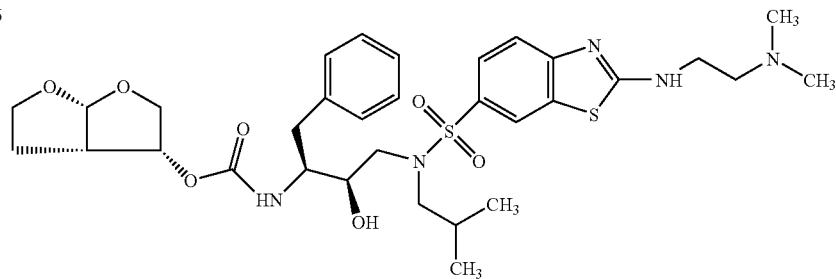 |
| 90 | 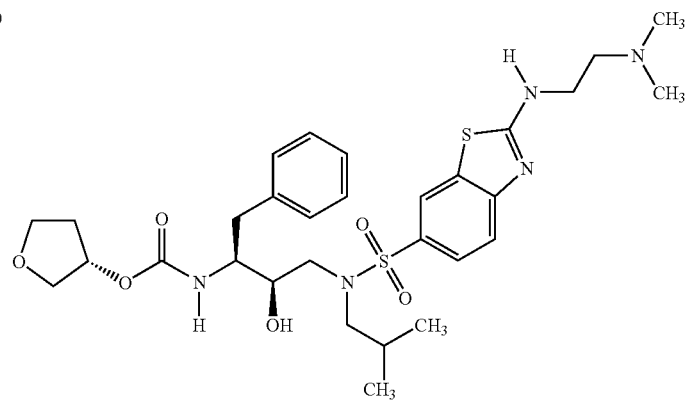 |
| 20 | 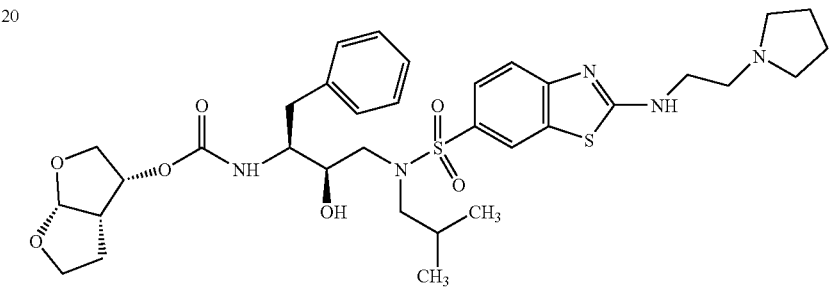 |
| 88 | 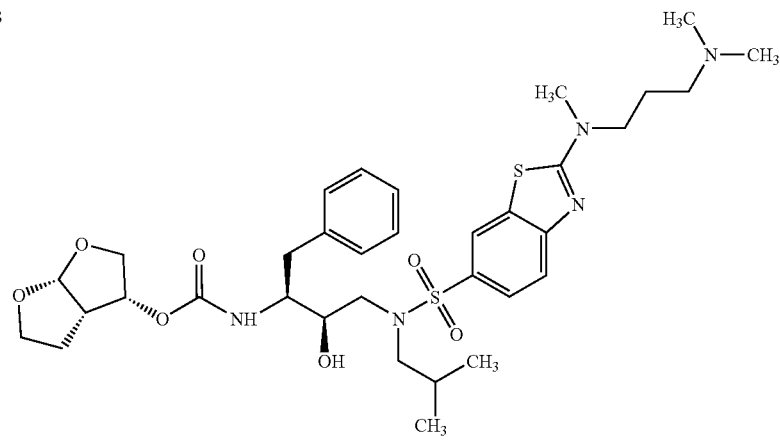 |

TABLE 5-continued
| Co | Structure |
|---|---|
| 93 | 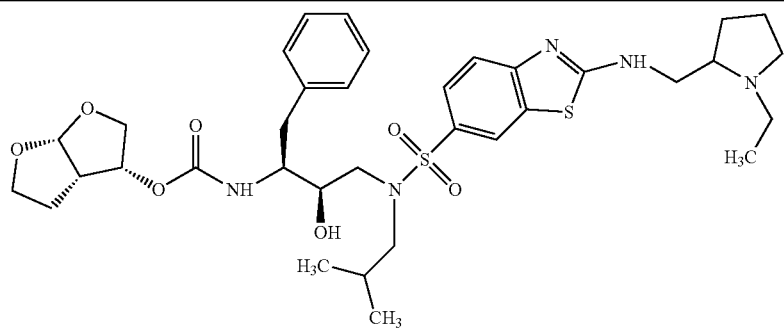 |
| 87 | 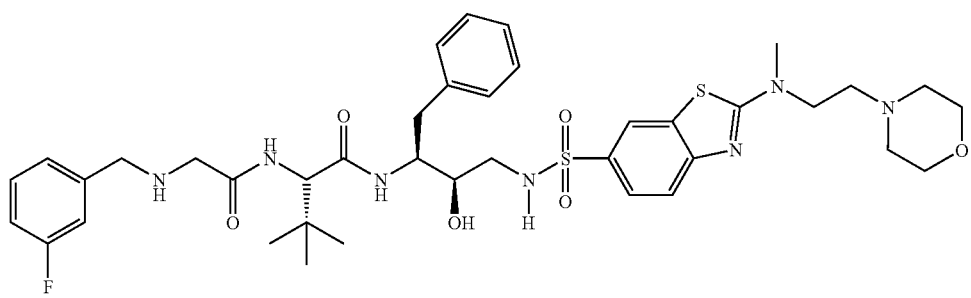 |
| 86 | 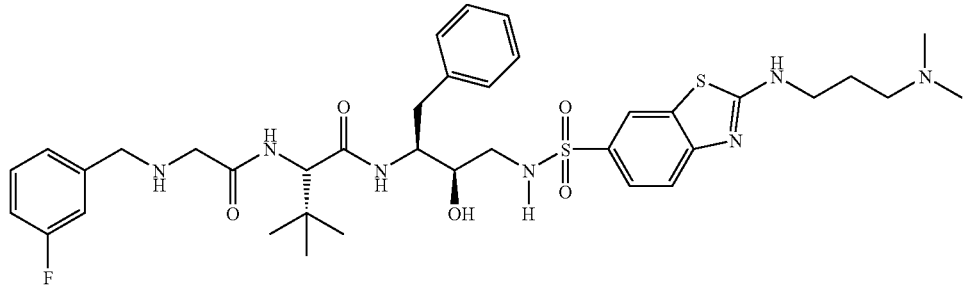 |
| 85 | 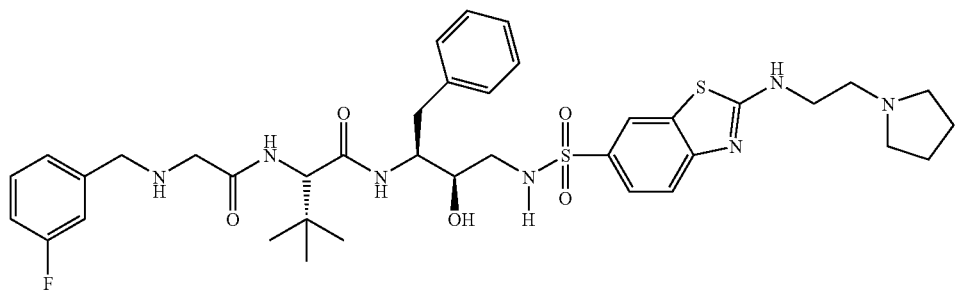 |

TABLE 6

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 100 | 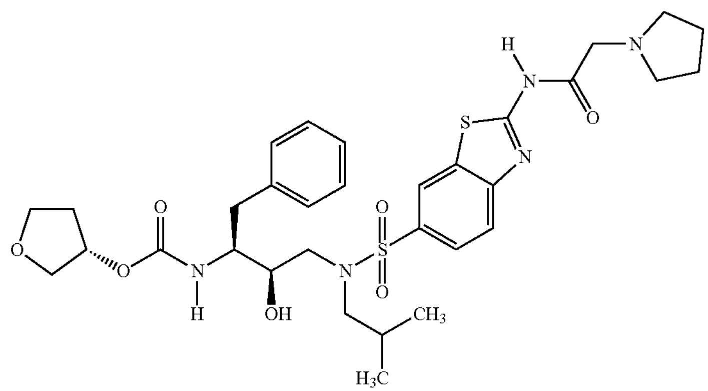 | 8.88 | 7.36 | 7.15 |
| 101 | 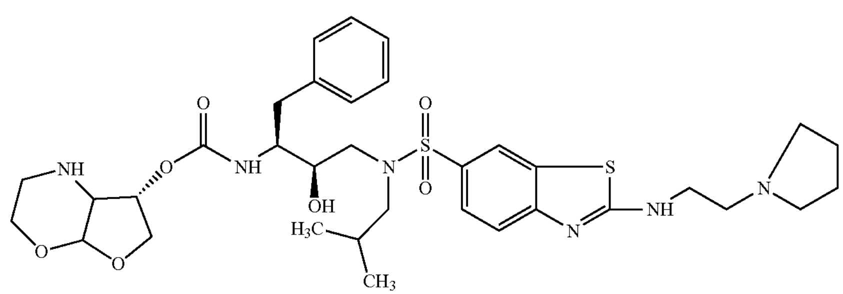 | 6.62 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 102 | 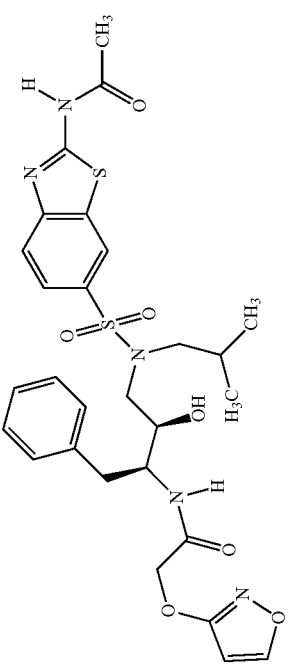 | 7.92 | 6.88 | 6.02 |
| 103 | 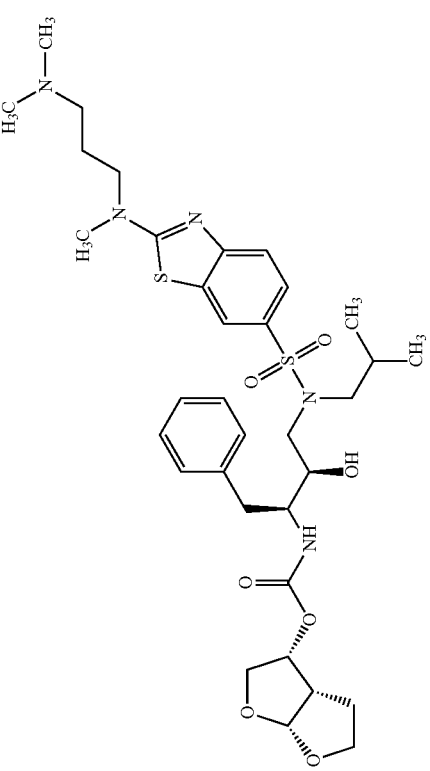 | 7.7 | 6.76 | 6.28 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 104 | 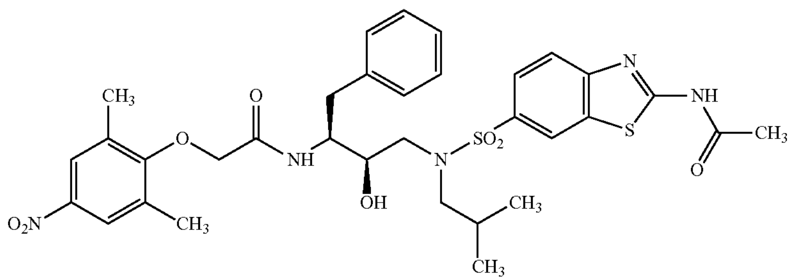 | 7.18 | | |
| 105 | 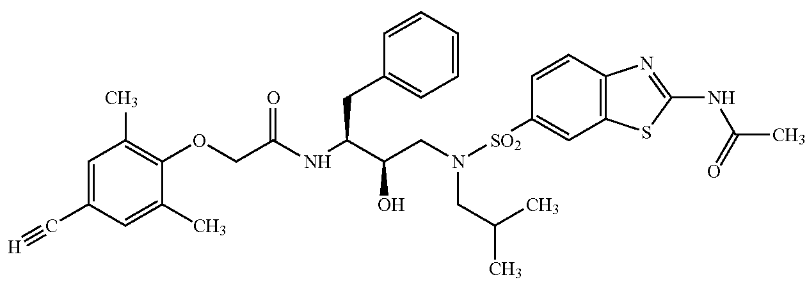 | 7.33 | 7.25 | 6.32 |
| 106 | 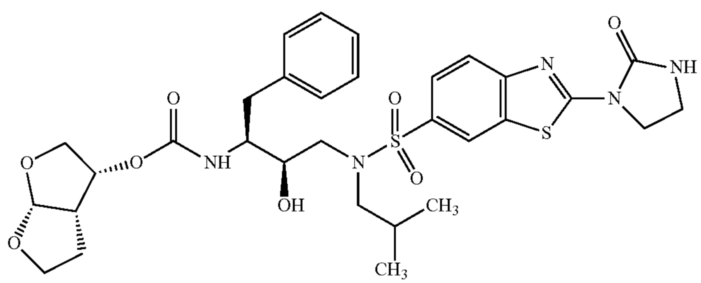 | 7.96 | 7.26 | 6.66 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 107 | 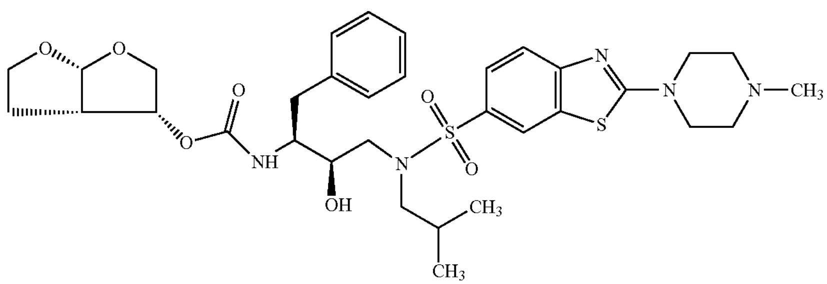 | 8.7 | 6.8 | 6.18 |
| 108 | 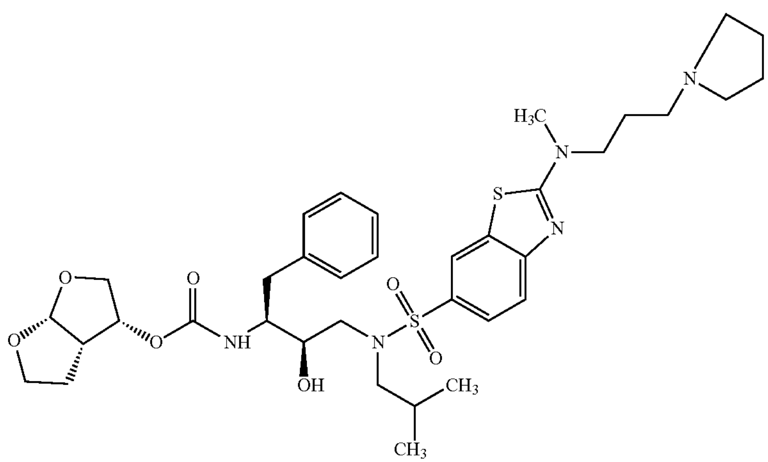 | 7.61 | 6.54 | 6.09 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 109 | 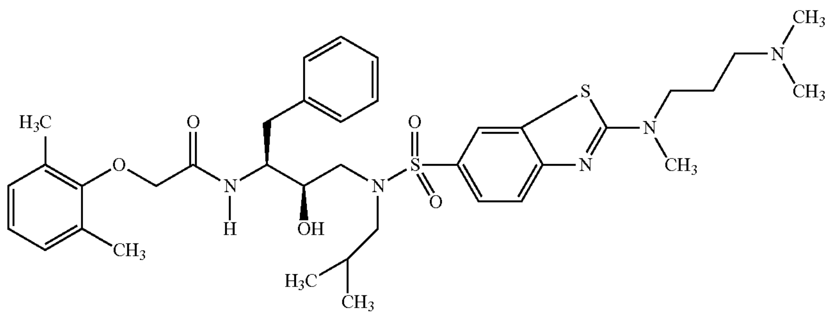 | 5.68 | 5.38 | |
| 110 | 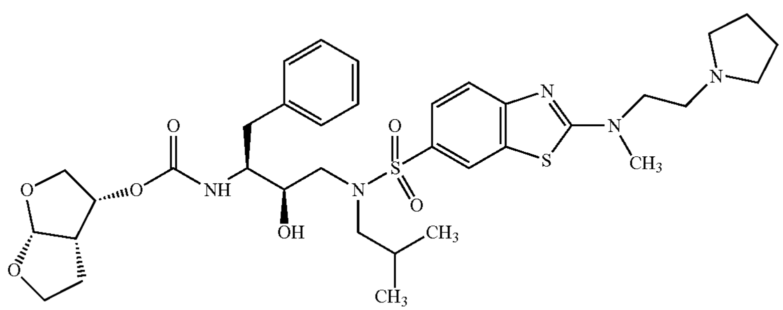 | 8.09 | 6.17 | 5.81 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 111 | 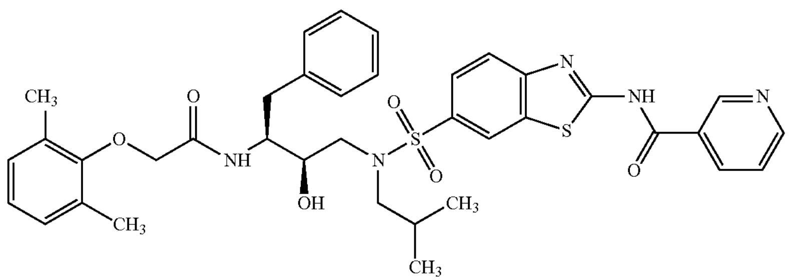 | 7.61 | 6.63 | 6.18 |
| 112 | 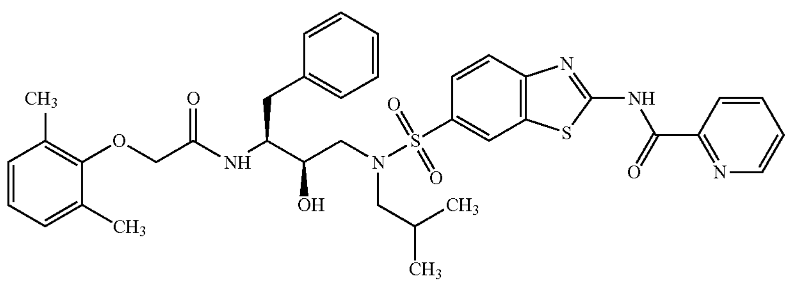 | 8 | 6.91 | 6.82 |
| 113 | 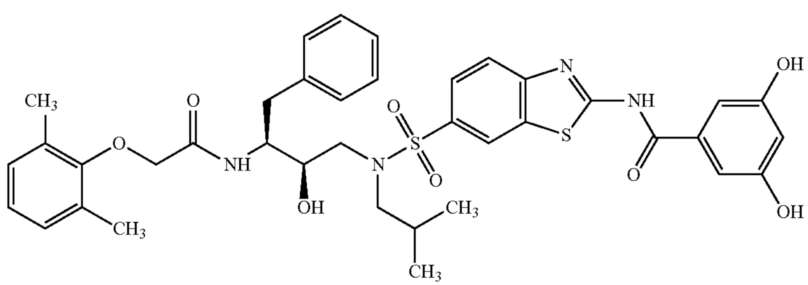 | 8.29 | 7.61 | 7.36 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 114 | 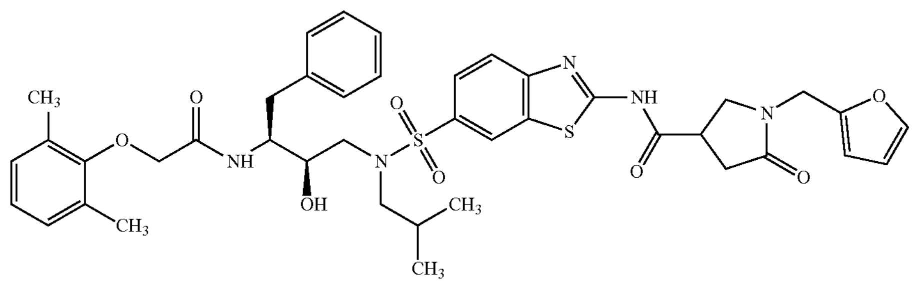 | 7.69 | 7.47 | 6.85 |
| 115 | 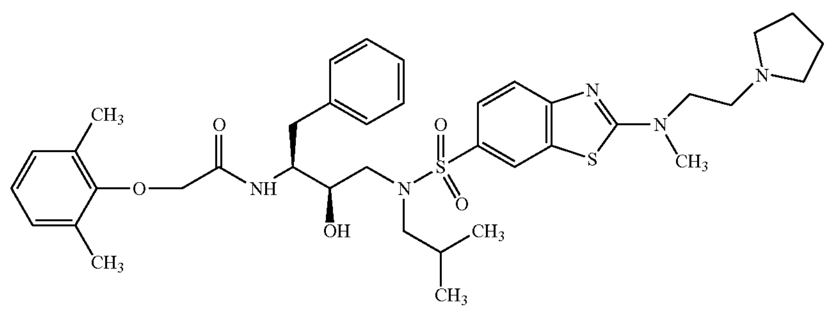 | 6.12 | 5.21 | 5 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 116 | 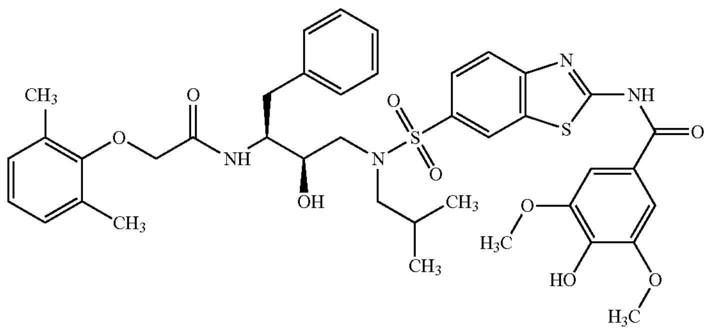 | 7.5 | 7.49 | 7.36 |
| 117 | 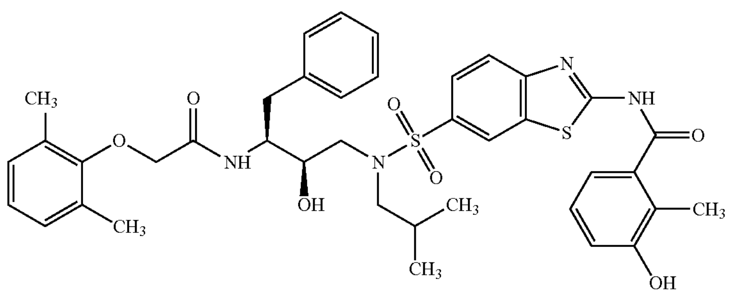 | 7.32 | 7.45 | 6.72 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 118 | 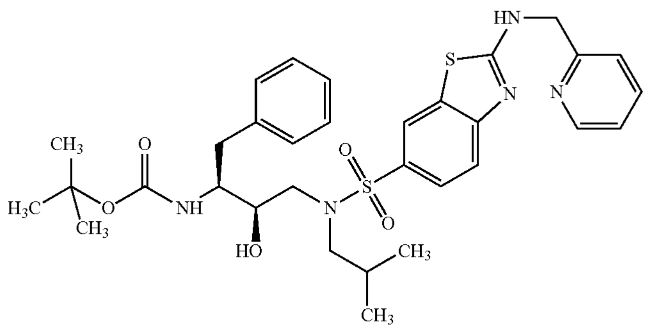 | 6.52 | | |
| 119 | 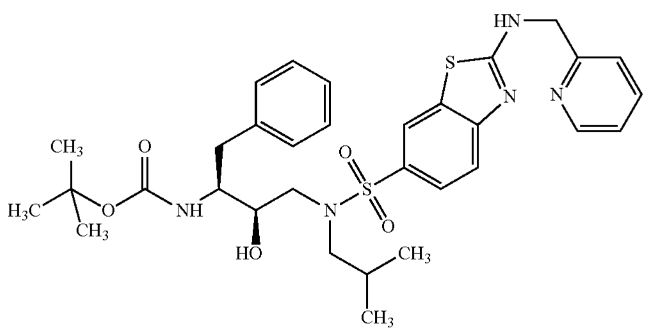 | 6.48 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 120 | 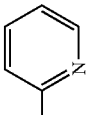 | 6.5 | | |
| 121 | 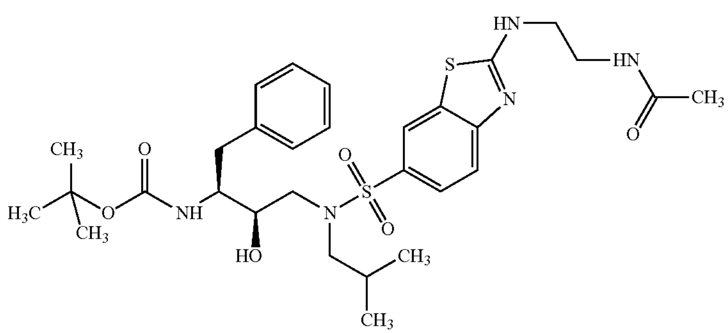 | 7.68 | 5.55 | 5 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 122 | 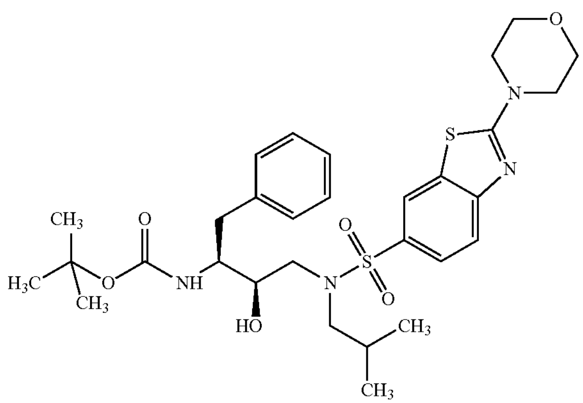 | 5.92 | | |
| 123 | 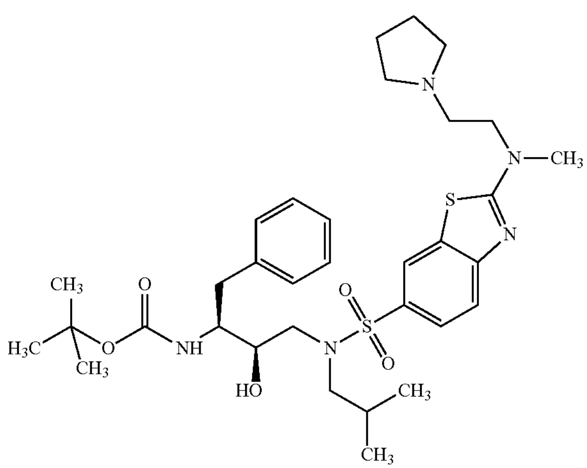 | 5.8 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 124 | 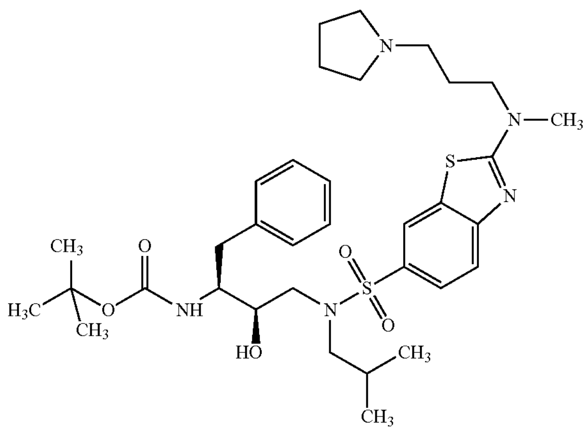 | 5.7 | | |
| 125 | 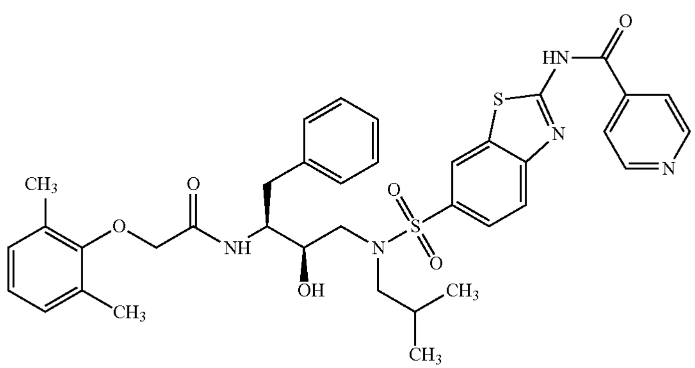 | 8.2 | 7.57 | 6.84 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 126 | 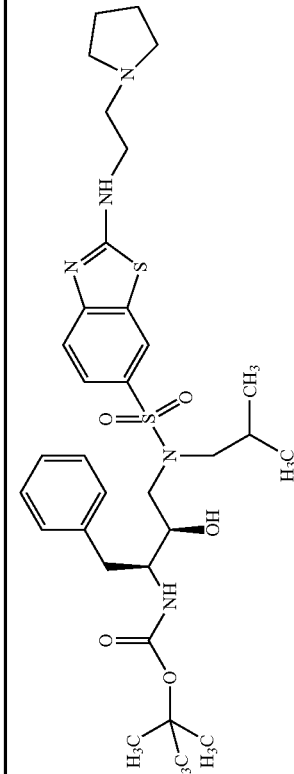 | 7.31 | 5.5 | 5 |
| 127 | 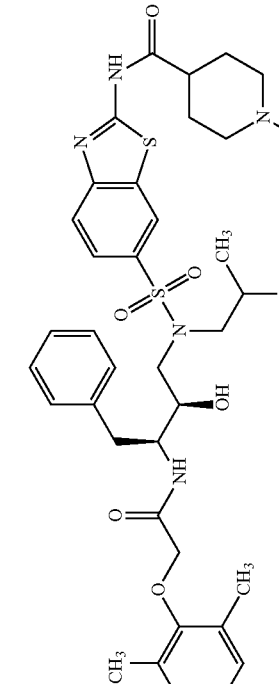 | 7.78 | 7.5 | 6.87 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 128 | 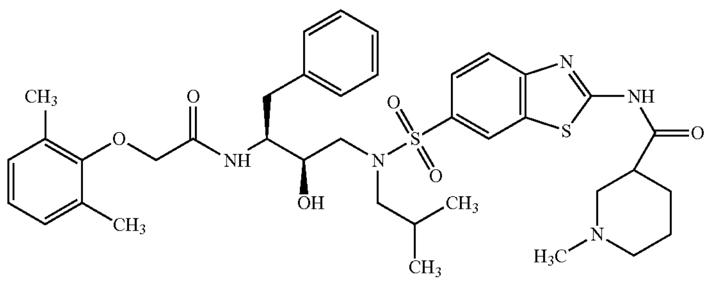 | 8.23 | 7.72 | 7.25 |
| 129 | 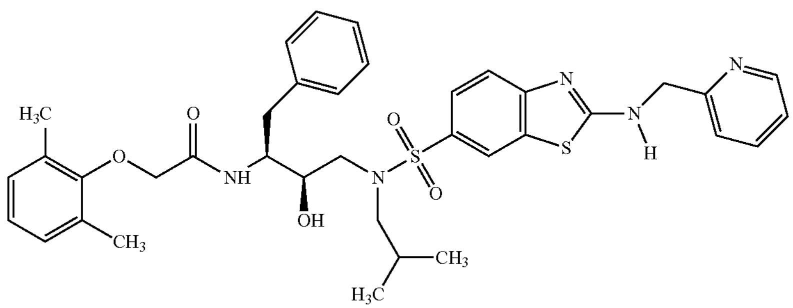 | 7.2 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 130 | 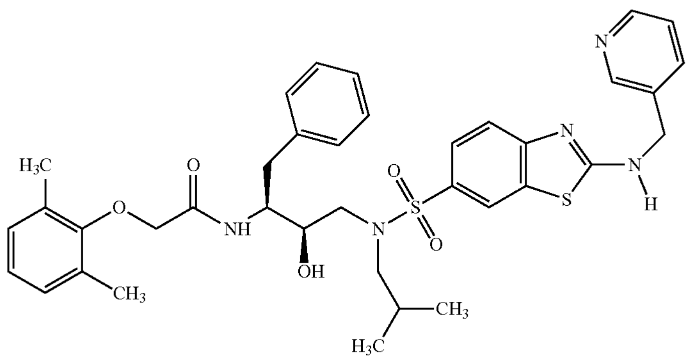 | 7.23 | | |
| 131 | 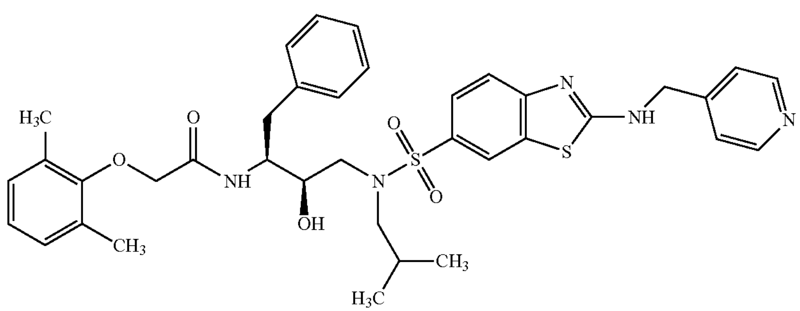 | 7.33 | 6.08 | 5.98 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 132 | 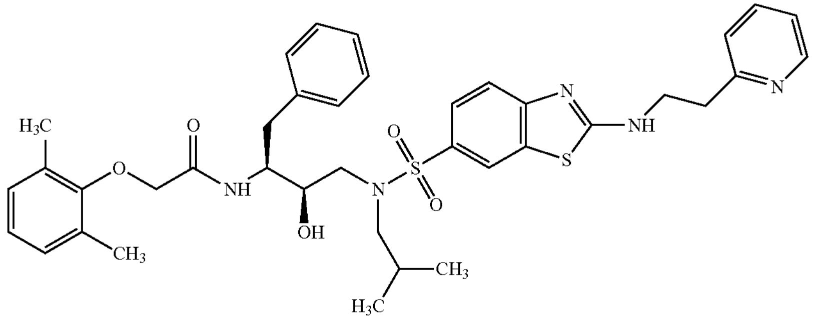 | 7.19 | | |
| 133 | 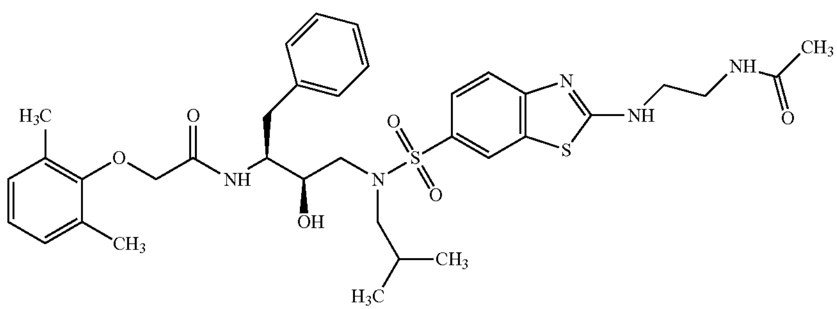 | 7.67 | 7.47 | 6.8 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 134 | 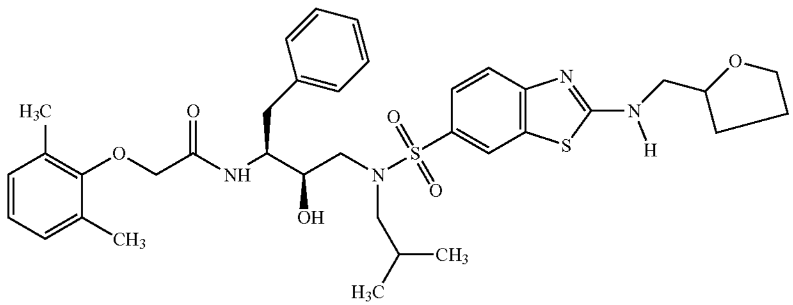 | 7.21 | | |
| 135 | 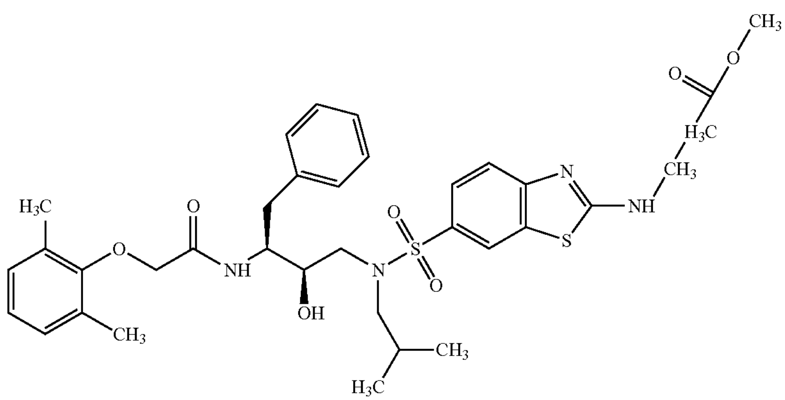 | 7.18 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 136 | 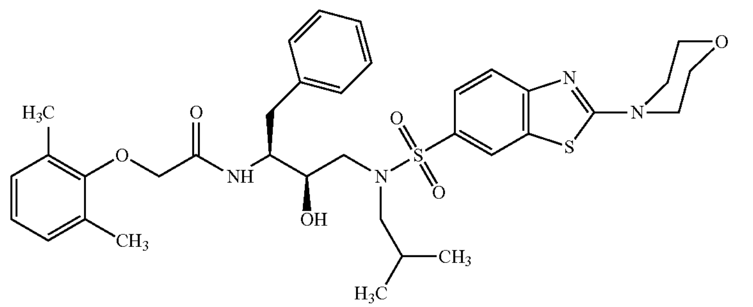 | 6.14 | | |
| 137 | 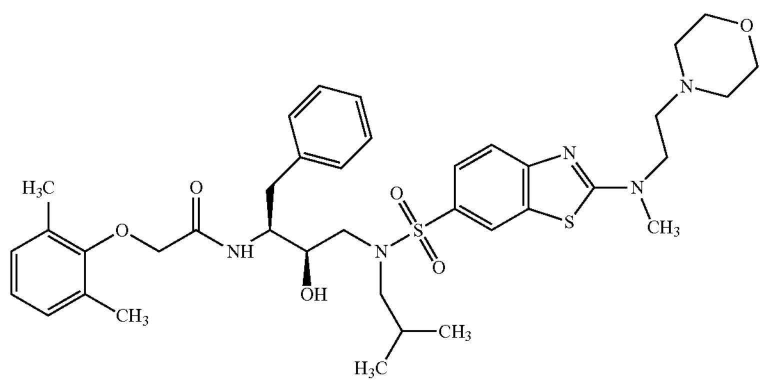 | 5.77 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 138 | 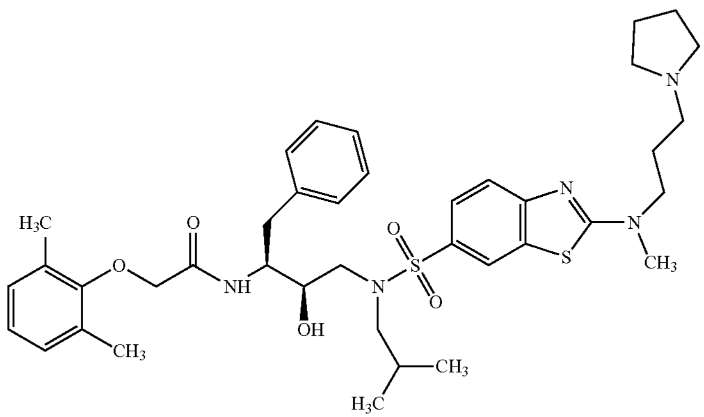 | 5.84 | | |
| 139 | 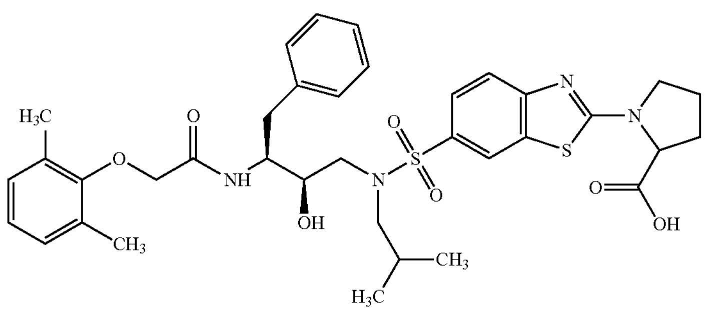 | 5.68 | 5.51 | 5 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 140 | 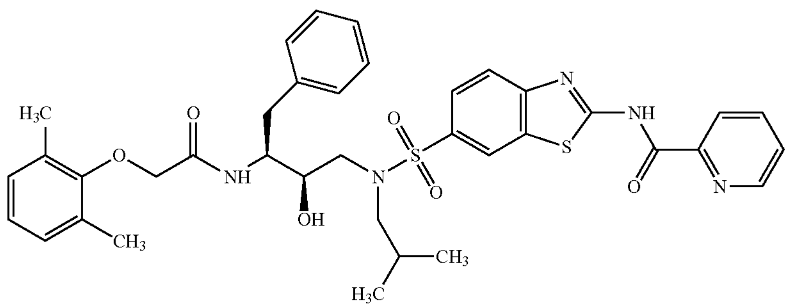 | 8.34 | 8.12 | |
| 141 | 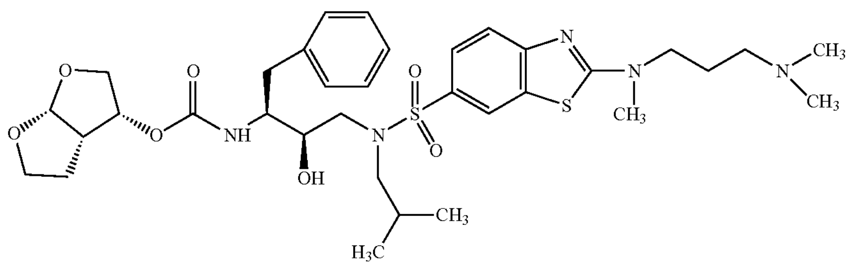 | 7.83 | 6.49 | 6.02 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 142 | 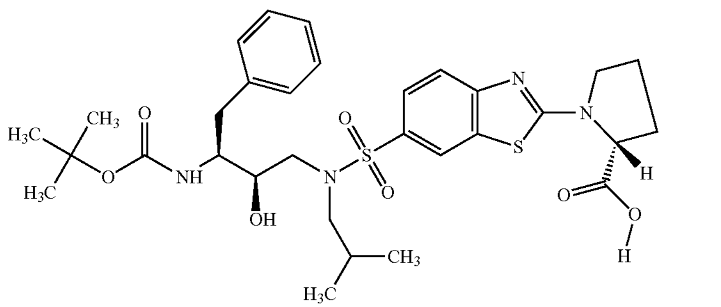 | 5.25 | | |
| 143 | 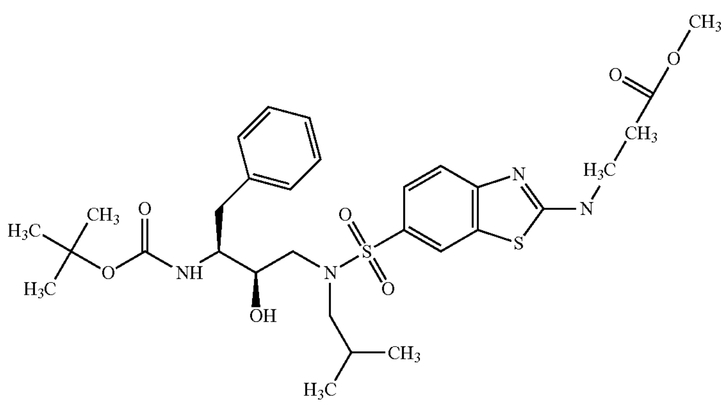 | 7.13 | 5 | 5 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 144 | 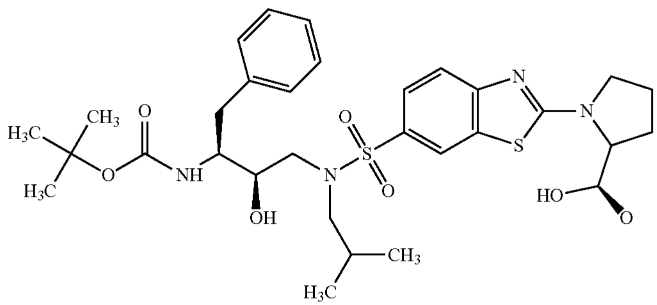 | 0 | | |
| 145 | 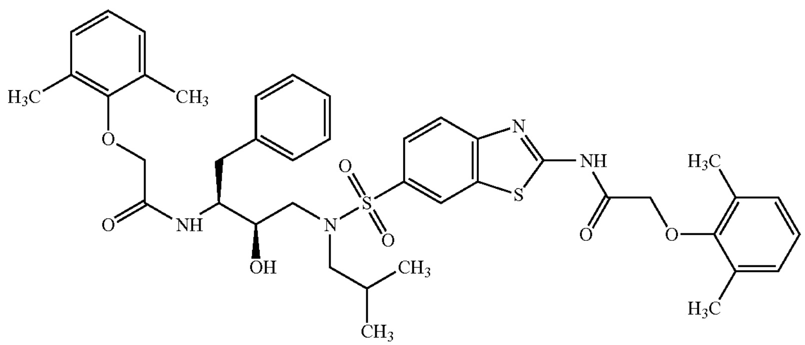 | 7.9 | 7.4 | 6.84 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 146 | 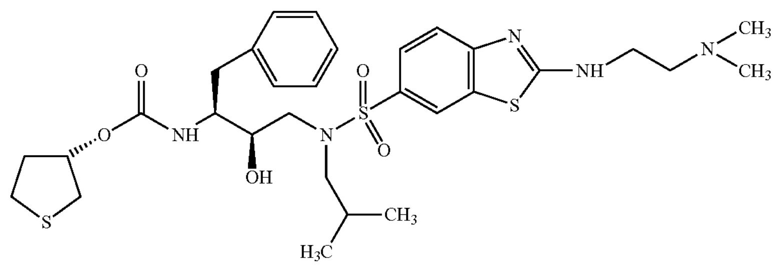 | 8.02 | 6.52 | 6 |
| 147 | 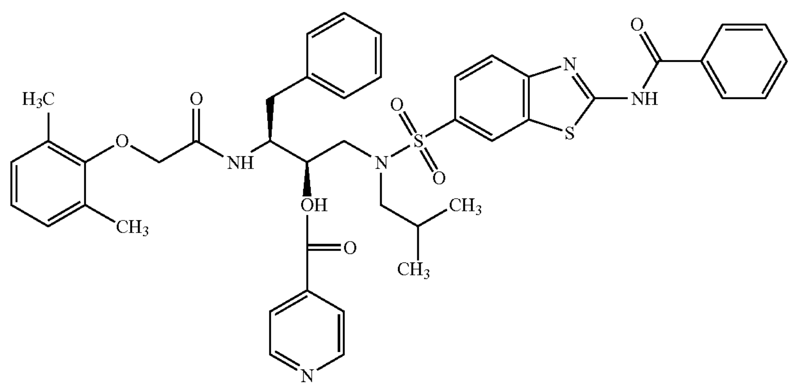 | 6.47 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 148 | | 6.43 | 6.51 | 6.56 |
| 149 | 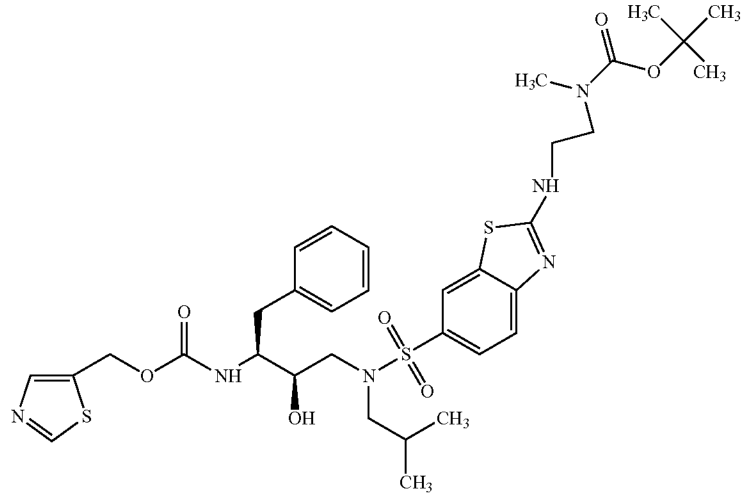 | 7.29 | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MIT-IIIB-2-002 pEC50 | HIV-AVE-MT4-MIT-R13025-2-002 pEC50 | HIV-AVE-MT4-MIT-R13080-2-002 pEC50 |
|---|---|---|---|---|
| 150 | 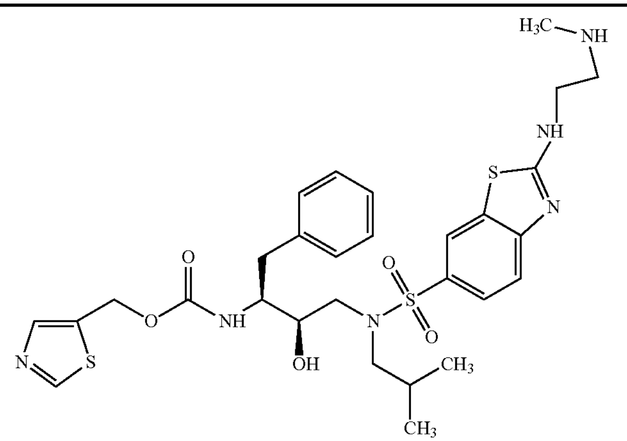 | 7.37 | 6.79 | 6.18 |
| 151 | 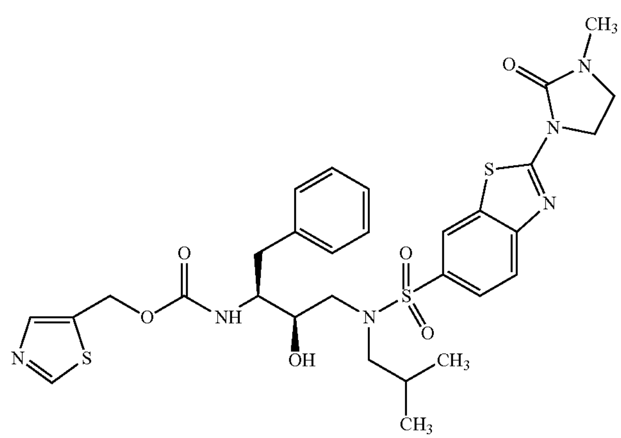 | 6.97 | 6.09 | 5.57 |

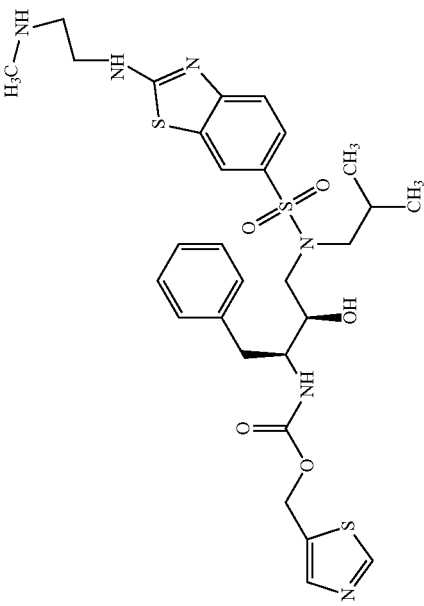

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 152 | 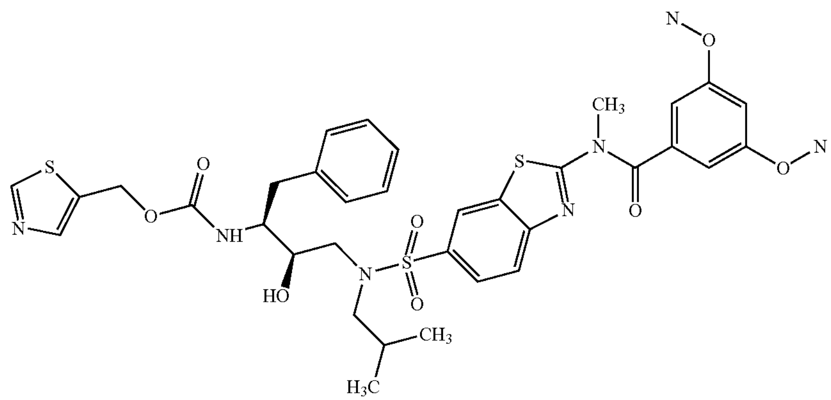 | 7.48 | 6.25 | 5.76 |
| 153 | 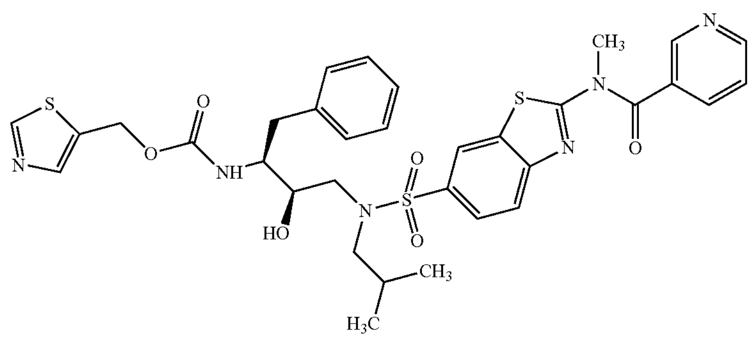 | 8.13 | 7.34 | 6.47 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 154 | 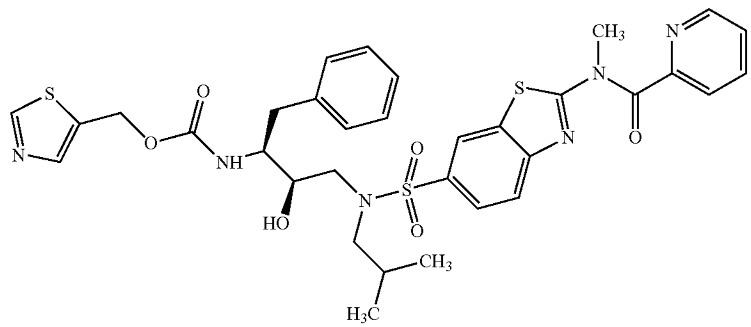 | 8.26 | 7.42 | 6.43 |
| 155 | 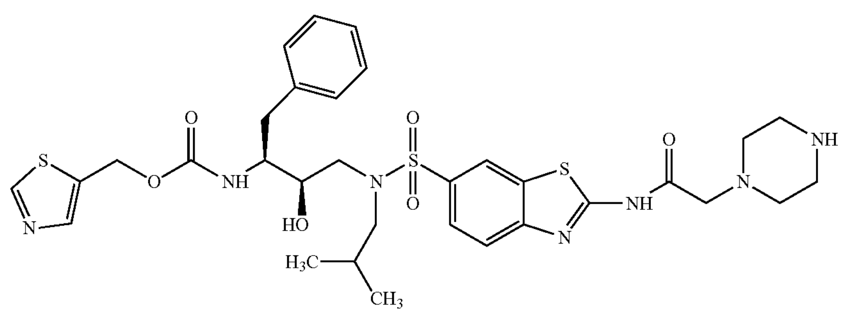 | 7.37 | 7.61 | 7.49 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 156 | 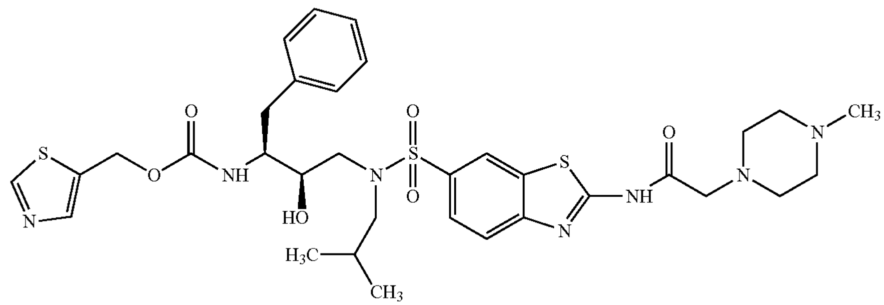 | 8.14 | 8.27 | 7.56 |
| 157 | 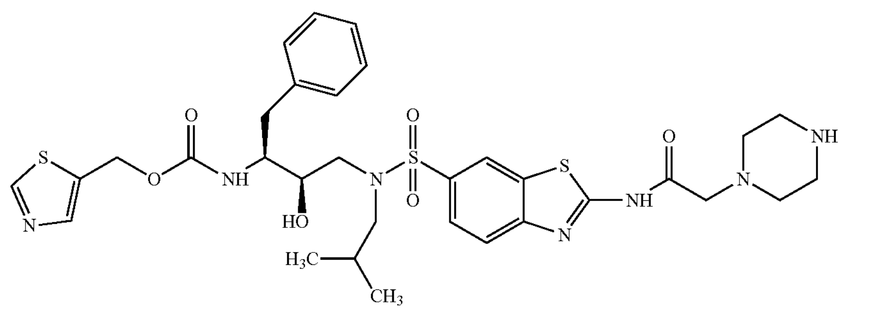 | 7.54 | 7.5 | 6.85 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 158 | 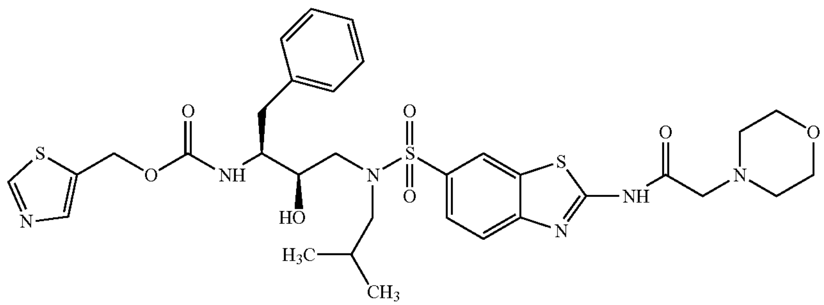 | 8.48 | 8.1 | 7.52 |
| 159 | 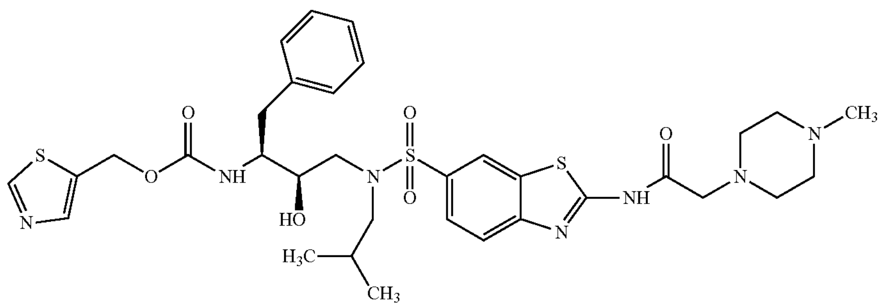 | 8.1 | 7.78 | 7.46 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 160 | 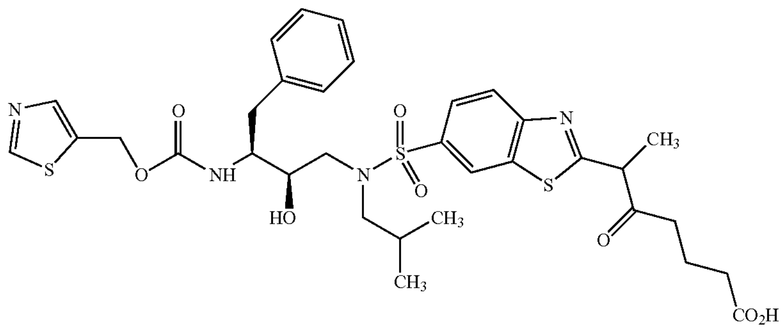 | 7.29 | 6.32 | 5.61 |
| 161 | 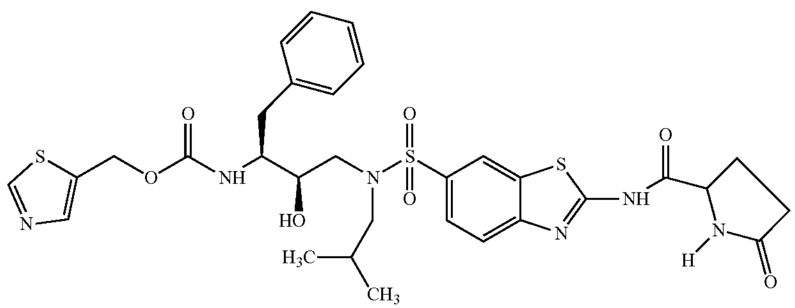 | 8.04 | 7.76 | 7.47 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
| --- | --- | --- | --- | --- |
| 162 | 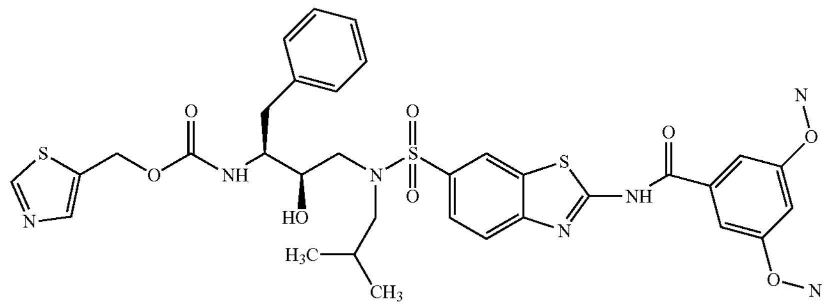 | 7.69 | 7.33 | 6.8 |
| 163 | 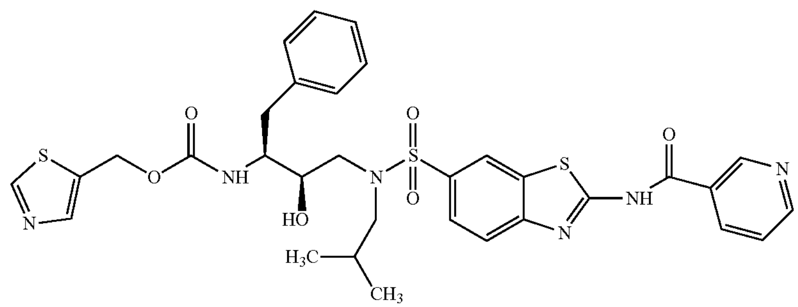 | 7.94 | 7.31 | 6.67 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 164 | 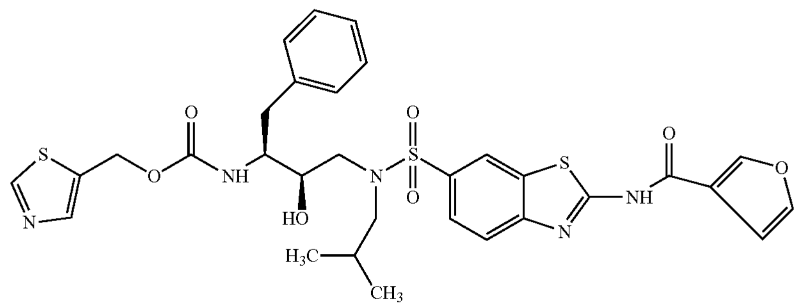 | 8.15 | 7.47 | 6.8 |
| 165 | 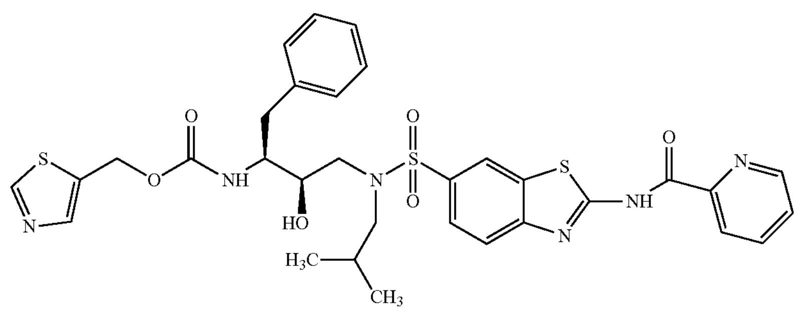 | 7.35 | 6.91 | 6.2 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 166 | 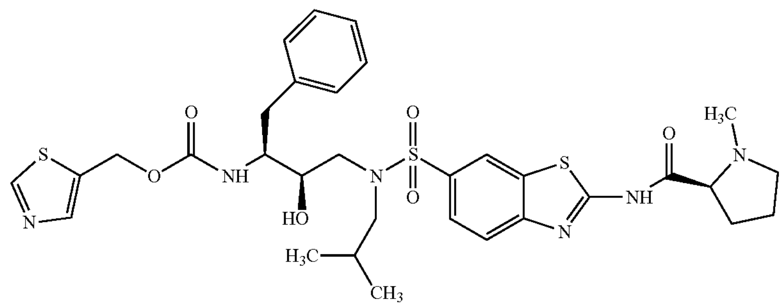 | 8.2 | 7.66 | 7.13 |
| 167 | 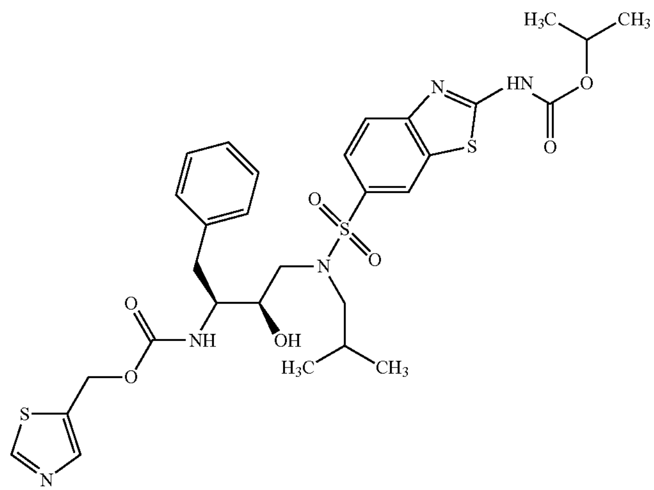 | 8.31 | 7.51 | 6.85 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 168 | 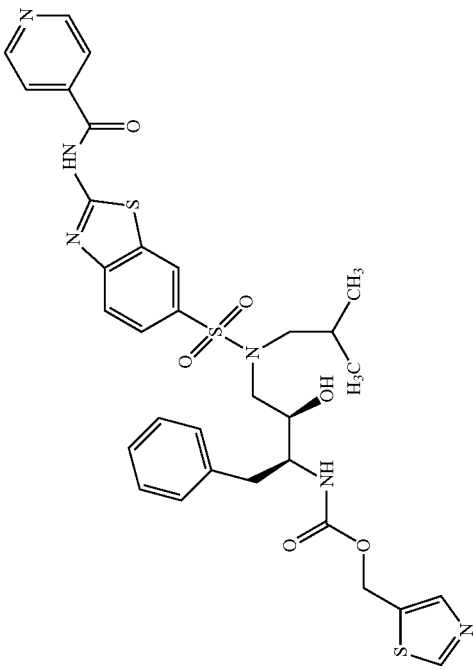 | 7.61 | 7.5 | 6.87 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 169 | 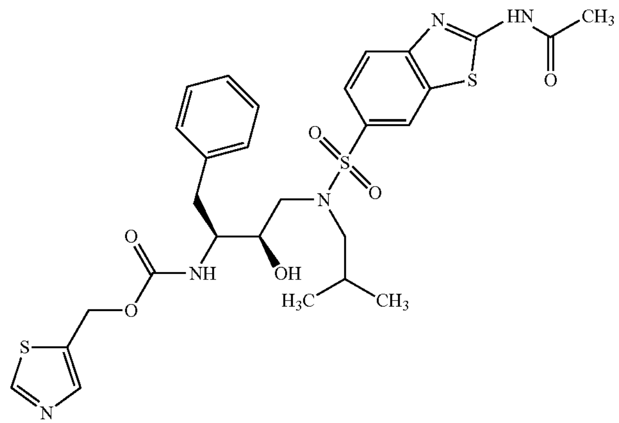 | 8.07 | 8.17 | 7.45 |
| 170 | 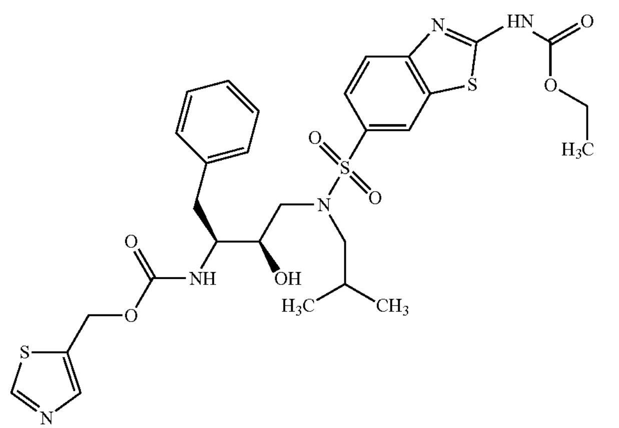 | 8.12 | 7.76 | 6.79 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 171 | 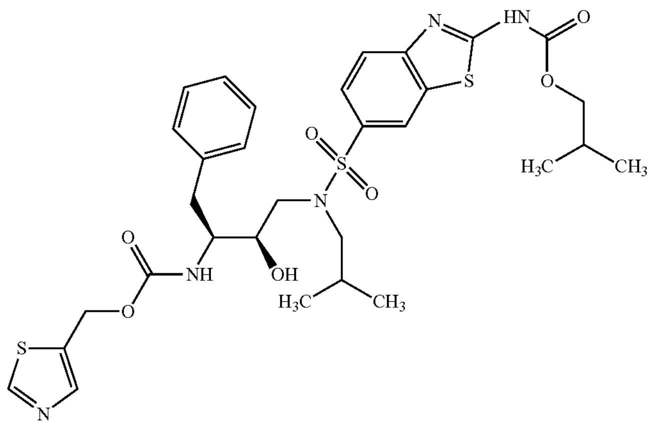 | 7.29 | 6.73 | 6.07 |
| 172 | 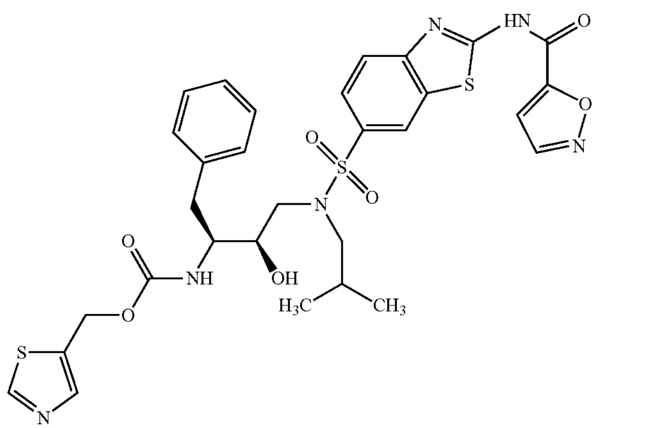 | 7.37 | 6.61 | 6.09 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 173 | 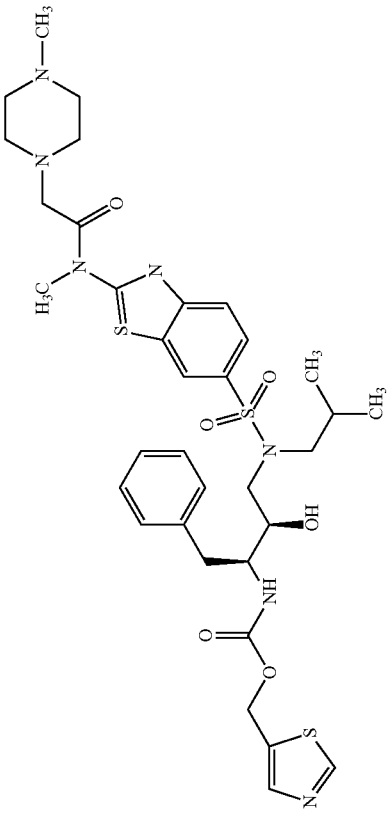 | 8.25 | 7.52 | 6.81 |
| 174 | 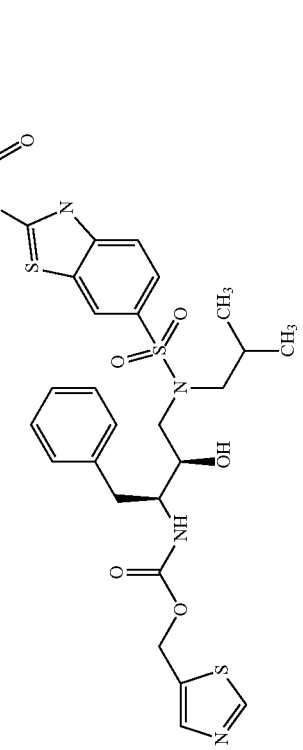 | 8.04 | 6.88 | 6.18 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 175 | 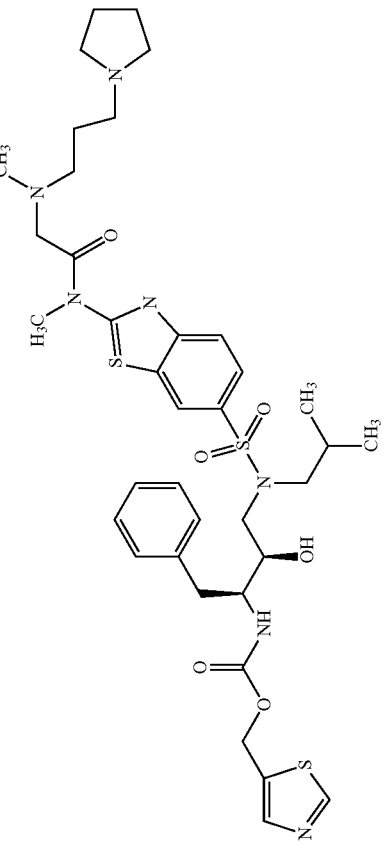 | 7.3 | 6.03 | 5.5 |
| 176 | 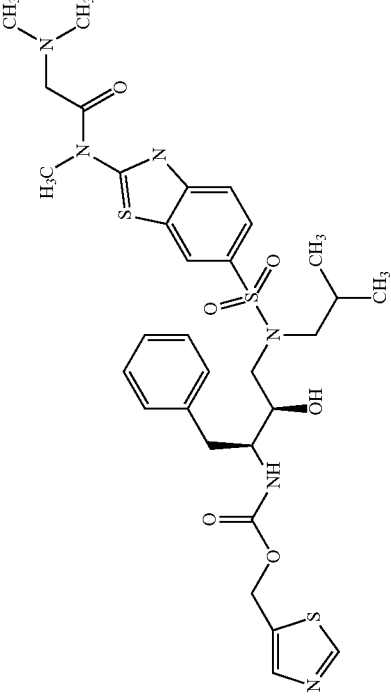 | 8.39 | 7.2 | 6.65 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 177 | 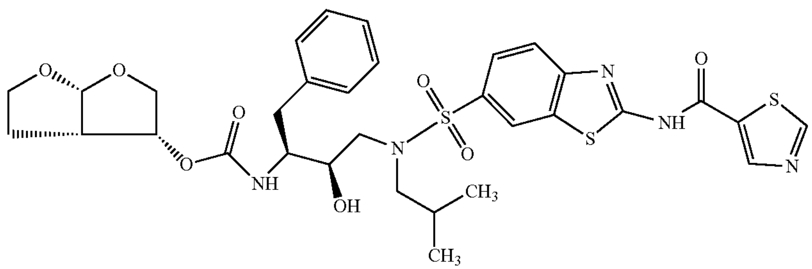 | 7.43 | 8.12 | 7.31 |
| 178 | 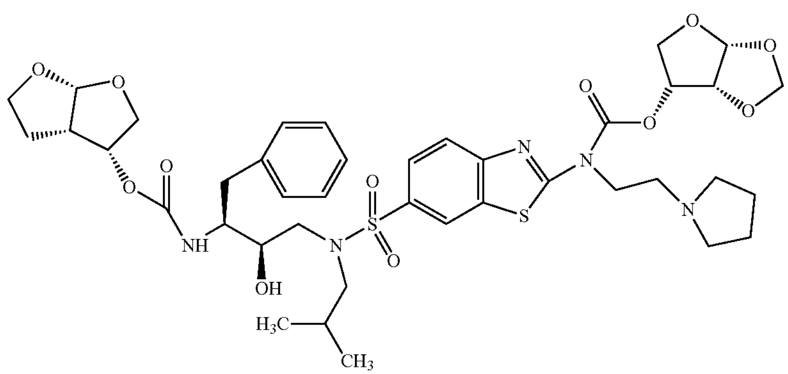 | 7.76 | 7.97 | 7.47 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MT-IIIB-2-002 pEC50 | HIV-AVE-MT4-MT-R13025-2-002 pEC50 | HIV-AVE-MT4-MT-R13080-2-002 pEC50 |
|---|---|---|---|---|
| 179 | 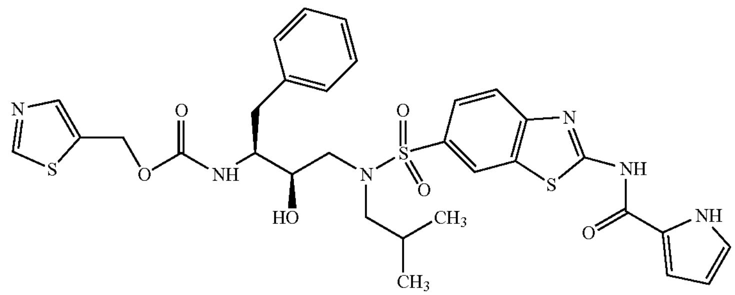 | 8.05 | 7.24 | 7.32 |
| 180 | 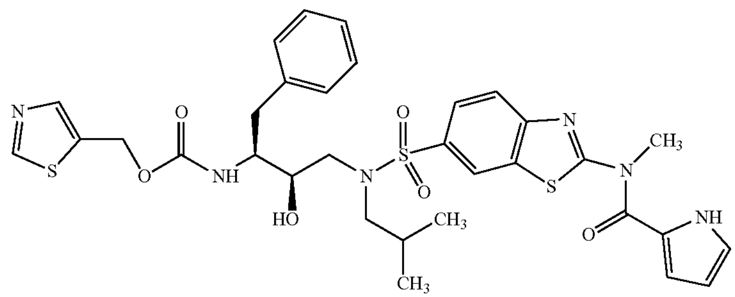 | 6.81 | 6.05 | 5 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 181 | 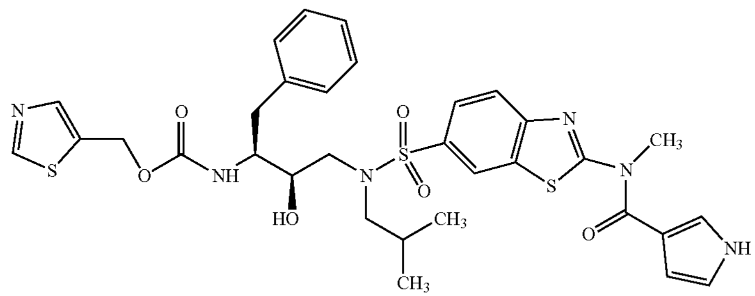 | 7.48 | 6.28 | 5.74 |
| 182 | 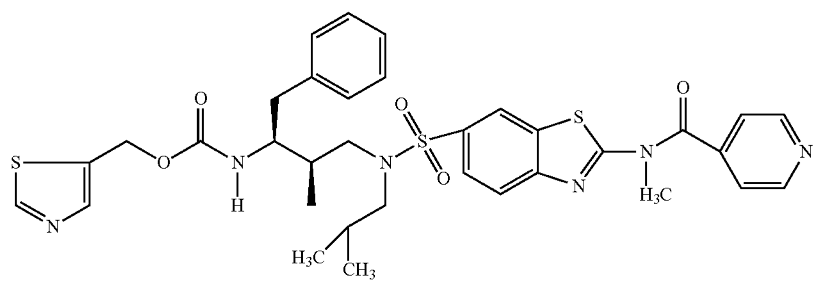 | 8.32 | 7.44 | 6.77 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 183 | 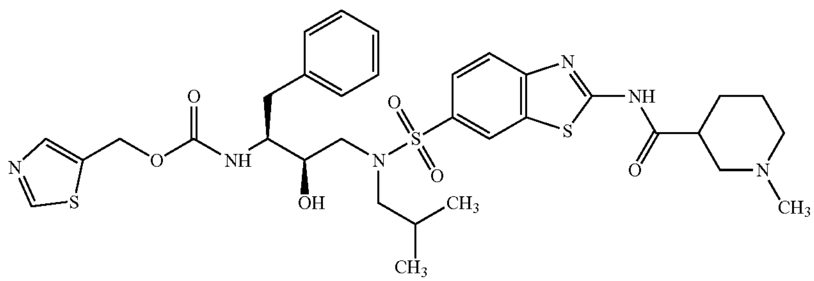 | 8.45 | 8.77 | 8.15 |
| 184 | 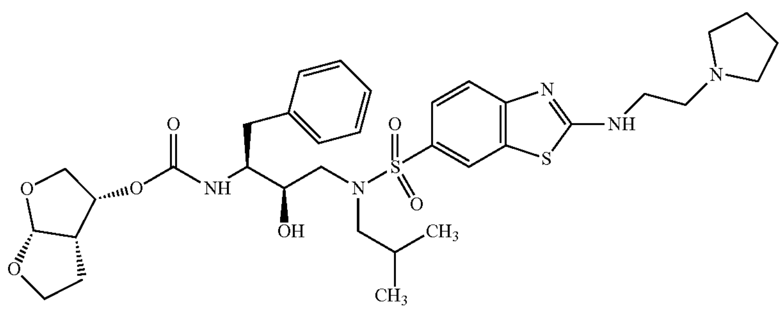 | 7.76 | 8.35 | 7.57 |
| 185 | 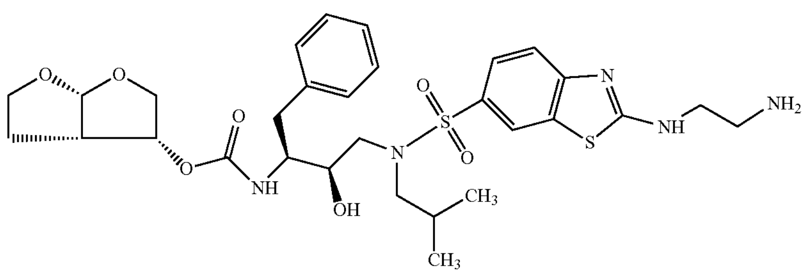 | 7.34 | 7.48 | 7.46 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 85 | 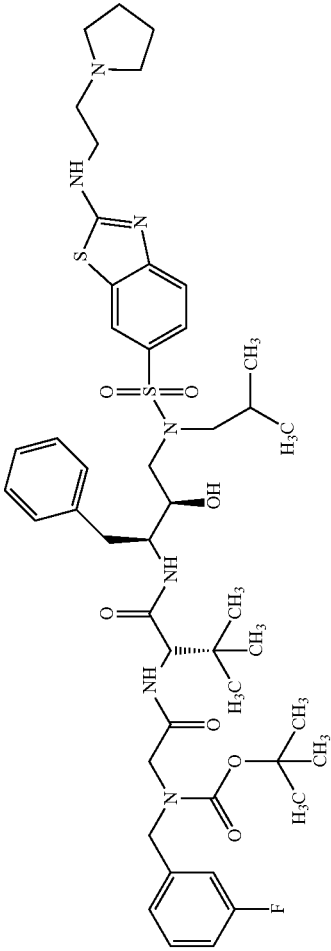 | 7.24 | | |
| 186 | 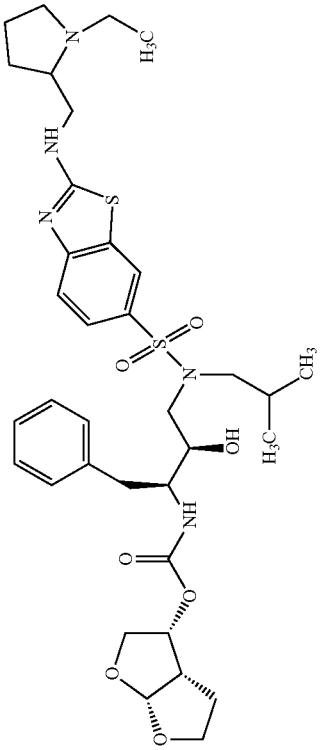 | 8.21 | 8.18 | 7.54 |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 86 | 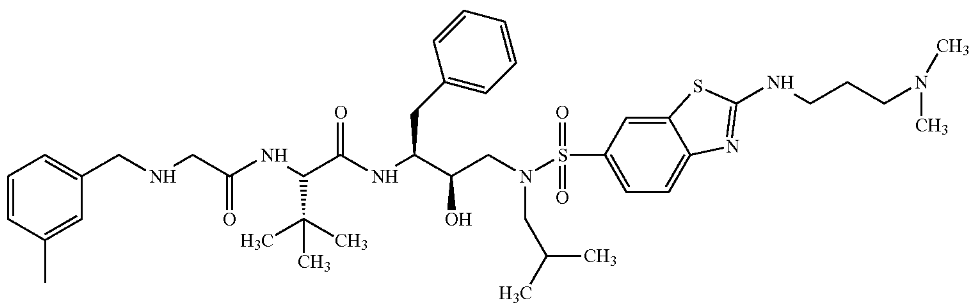 | | | |
| 187 | 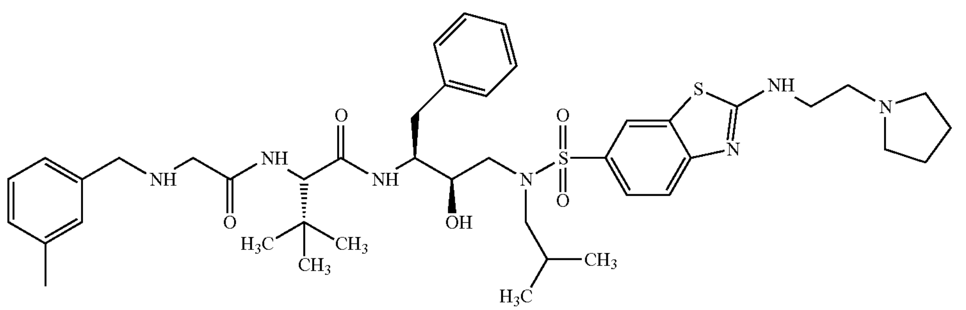 | | | |

TABLE 6-continued

The following compounds were also prepared. The compounds were evaluated according to the methods described infra. Column 3 displays the results as pEC50 against wild type virus (IIIB). Column 4 displays the results as pEC50 against wild virus strain F (R13025). Column 5 displays the results as pEC50 against wild virus strain S (R13080).

| Compound number | Structure | HIV-AVE-MT4-MTT-IIIB-2-002 pEC50 | HIV-AVE-MT4-MTT-R13025-2-002 pEC50 | HIV-AVE-MT4-MTT-R13080-2-002 pEC50 |
|---|---|---|---|---|
| 188 | 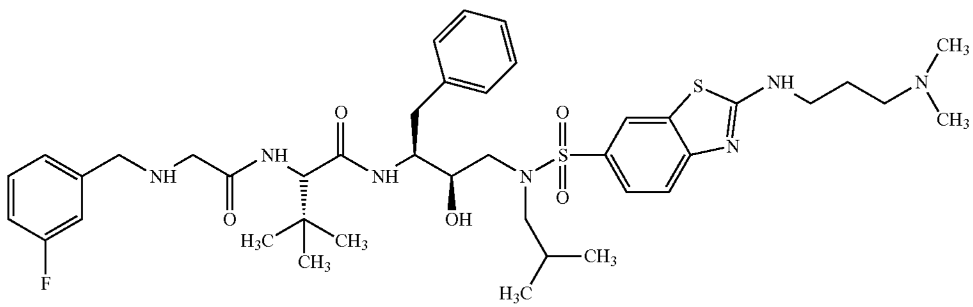 | 6.7 | 7.03 | 6.88 |
| 189 | 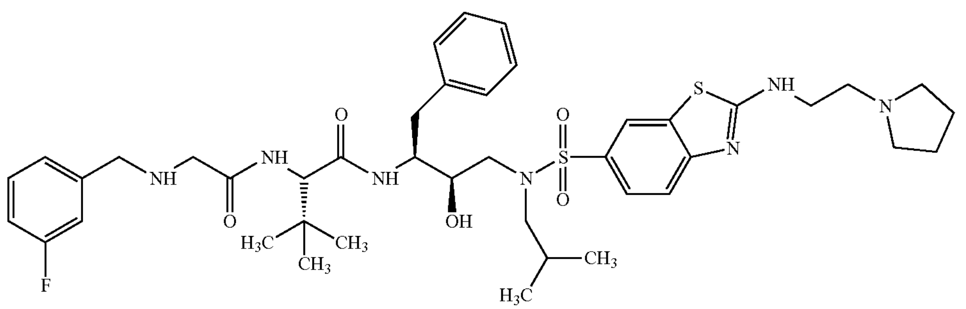 | 7.35 | 6.99 | 6.86 |

Antiviral Analyses:

The compounds of the present invention were examined for anti-viral activity in a cellular assay. The assay demonstrated that these compounds exhibited potent anti-HIV activity against a wild type laboratory HIV strain (HIV-1 strain LAI). The cellular assay was performed according to the following procedure.

Cellular Assay Experimental Method:

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as $EC_{50}$ and $EC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor.

The compounds 1-4, 7, 9-19, 21, 24-26, 28, 33-35, 37-43, 45, 46, 49, 50, 56, 61-64, 66, 68, 70, 71, 75, 79-83 and 88-93 all have an $EC_{50}$ value against HIV-1 strain LAI of less than 50 nM. The SI for these compounds ranges between about 400 up to more than 47000.

The compounds 5, 6, 20, 22, 23, 29, 36, 44, 47, 48, 51-55, 58, 59, 69, 72-74, 76-78 and 84 all had an $EC_{50}$ value against HIV-1 strain LAI between 50 nM and 500 nM. The SI for these compounds ranges between about 26 up to more than 1900.

The compounds 27, 30, 31, 57 and 60 have an $EC_{50}$ against HIV-1 strain LAI of more than 500 nM. The SI for these compounds ranges between more than 13 up to more than 183.

Antiviral Spectrum:

Because of the increasing emergence of drug resistant HIV strains, the present compounds were tested for their potency against clinically isolated HIV strains harboring several mutations. These mutations are associated with resistance to protease inhibitors and result in viruses that show various degrees of phenotypic cross-resistance to the currently commercially available drugs such as for instance saquinavir, ritonavir, nelfinavir, indinavir and amprenavir.

Results:

As a measure of the broad spectrum activity of the present compounds, the fold resistance (FR) defined as FR=$EC_{50}$ (mutant strain)/$EC_{50}$(HIV-1 strain LAI). Table 7 shows the results of the antiviral testing in terms of fold resistance. As can be seen in this table, the present compounds are effective in inhibiting a broad range of mutant strains.

TABLE 7

| | | STRAIN | | | | | | | | | | | | | | | | | | | |
|---|---|---|---|---|---|---|---|---|---|---|---|---|---|---|---|---|---|---|---|---|---|
| Co | LAI | A | B | C | D | E | F | G | H | I | J | K | L | M | N | O | P | Q | R | S | T |
| 1 | 1 | 0.4 | 0.3 | 0.7 | 0.7 | 0.6 | 0.8 | 0.3 | 0.9 | 0.8 | 0.5 | 0.4 | 0.2 | 0.5 | 1.0 | 0.4 | 0.2 | 0.8 | 0.7 | 1.0 | 5.1 |
| 2 | 1 | 0.3 | 0.2 | 0.2 | 0.3 | 0.4 | 1.1 | 0.2 | 1.0 | 0.7 | 0.4 | 0.2 | 0.2 | 0.3 | 1.1 | 0.8 | 0.2 | 0.3 | 0.3 | 1.7 | 29.6 |
| 3 | 1 | 0.4 | 0.4 | 0.4 | 0.8 | 0.4 | 1.1 | 0.4 | 1.0 | 0.8 | 0.4 | 0.4 | 0.3 | 0.4 | 2.3 | 1.0 | 0.4 | 0.5 | 0.5 | 1.8 | 34.2 |
| 4 | 1 | — | — | — | — | — | 2.2 | — | 1.9 | 1.2 | 0.5 | — | — | — | — | 0.5 | — | — | — | 2.9 | 48.8 |
| 5 | 1 | — | — | — | — | — | 0.5 | — | 0.6 | 0.6 | 0.3 | — | — | — | — | 0.4 | — | — | — | 0.6 | 2.6 |
| 6 | 1 | — | — | — | — | — | 24.0 | — | 7.7 | 5.3 | 5.6 | — | — | — | — | 4.7 | — | — | — | 30.7 | 104.3 |
| 7 | 1 | 0.2 | 0.3 | 0.5 | 0.5 | 0.3 | 0.5 | 0.2 | 0.5 | 0.5 | 0.4 | 0.3 | 0.1 | 0.1 | 0.5 | 0.4 | 0.1 | 0.4 | 0.4 | 2.0 | 12.4 |
| 9 | 1 | 1.5 | 1.5 | 1.6 | 5.7 | 2.3 | 13.0 | 1.5 | 6.7 | 2.3 | 6.2 | 1.0 | 0.7 | 0.5 | 1.5 | 3.7 | 0.2 | 1.8 | 1.2 | 29.3 | 550.9 |
| 10 | 1 | 0.4 | 0.4 | 0.6 | 0.5 | 0.4 | 0.5 | 0.5 | 0.4 | 0.4 | 0.3 | 0.3 | 0.2 | 0.3 | 0.0 | 0.4 | 0.3 | 0.3 | 0.3 | 0.5 | 4.9 |
| 11 | 1 | 0.3 | 0.4 | 0.5 | 0.3 | — | 0.7 | 0.5 | 0.9 | 0.5 | 0.4 | 0.4 | 0.3 | 0.4 | 1.6 | 0.7 | 0.3 | 0.0 | 0.5 | 1.1 | 7.3 |
| 12 | 1 | 0.3 | 0.4 | 0.3 | 0.4 | 0.4 | 0.4 | 0.2 | 0.4 | 0.4 | 0.3 | 0.2 | 0.1 | 0.2 | 0.4 | 0.4 | 0.1 | 0.4 | 0.4 | 0.8 | 5.9 |
| 13 | 1 | 0.2 | 0.2 | 0.2 | 0.2 | 0.2 | 0.6 | 0.2 | 0.6 | 0.3 | 0.2 | 0.2 | 0.1 | 0.2 | 1.0 | 0.3 | 0.2 | 0.4 | 0.2 | 1.0 | 5.8 |
| 14 | 1 | 0.2 | 0.2 | 0.2 | 0.2 | 0.3 | 0.4 | 0.2 | 0.5 | 0.4 | 0.3 | 0.2 | 0.1 | 0.2 | 0.9 | 0.3 | 0.2 | 0.3 | 0.2 | 0.7 | 5.9 |
| 15 | 1 | 0.3 | 0.2 | 0.3 | 0.3 | 0.3 | 0.5 | 0.3 | 0.5 | 0.3 | 0.3 | 0.3 | 0.1 | 0.2 | 0.4 | 0.2 | 0.1 | 0.2 | 0.2 | 0.8 | 7.2 |
| 16 | 1 | 0.2 | 0.3 | 0.2 | 0.2 | 0.3 | 0.4 | 0.2 | 0.3 | 0.3 | 0.3 | 0.2 | 0.1 | 0.2 | 0.4 | 0.3 | 0.1 | 0.2 | 0.2 | 1.6 | 6.6 |
| 17 | 1 | — | — | — | — | — | 0.3 | — | 0.8 | 0.7 | 0.2 | — | — | — | — | 0.3 | — | — | — | 0.6 | 1.0 |
| 18 | 1 | — | — | — | — | — | 1.0 | — | 1.0 | 0.9 | 0.9 | — | — | — | — | 0.9 | — | — | — | 1.0 | 5.4 |
| 19 | 1 | — | — | — | — | — | 2.4 | — | 2.1 | 1.1 | 0.6 | — | — | — | — | 0.5 | — | — | — | 2.2 | 10.5 |
| 20 | 1 | — | — | — | — | — | 0.5 | — | 0.5 | 0.4 | 0.2 | — | — | — | — | 0.2 | — | — | — | 0.5 | 2.6 |
| 21 | 1 | — | — | — | — | — | 16.6 | — | 4.8 | 3.7 | 3.3 | — | — | — | — | 3.4 | — | — | — | 38.6 | 380.0 |
| 22 | 1 | — | — | — | — | — | 0.3 | — | 0.4 | 0.6 | 0.4 | — | — | — | — | 0.4 | — | — | — | 1.4 | 6.0 |
| 23 | 1 | — | — | — | — | — | 1.1 | — | 1.2 | 1.0 | 1.0 | — | — | — | — | 0.9 | — | — | — | 1.1 | 1.2 |
| 24 | 1 | — | — | — | — | — | 16.6 | — | 4.7 | 1.1 | 4.5 | — | — | — | — | 1.6 | — | — | — | 24.1 | 174.9 |
| 25 | 1 | — | — | — | — | — | 26.0 | — | 4.7 | 3.5 | 6.0 | — | — | — | — | 5.6 | — | — | — | 42.5 | 619.8 |
| 26 | 1 | — | — | — | — | — | 29.6 | — | 20.3 | 6.6 | 9.2 | — | — | — | — | 10.6 | — | — | — | 34.1 | 345.6 |
| 27 | 1 | — | — | — | — | — | 1.4 | — | 1.2 | 1.3 | 0.7 | — | — | — | — | 0.6 | — | — | — | 5.1 | 5.4 |
| 28 | 1 | — | — | — | — | — | 2.3 | — | 1.8 | 1.4 | 0.7 | — | — | — | — | 0.8 | — | — | — | 4.4 | 12.7 |
| 30 | 1 | — | — | — | — | — | — | — | — | — | — | — | — | — | — | — | — | — | — | — | — |
| 31 | 1 | — | — | — | — | — | — | — | — | — | — | — | — | — | — | — | — | — | — | — | — |
| 33 | 1 | — | — | — | — | — | 7.6 | — | 6.8 | 7.1 | 5.9 | — | — | — | — | 3.4 | — | — | — | 467.3 | 467.3 |
| 34 | 1 | 5.0 | 5.9 | 5.5 | 6.6 | 4.5 | 61.9 | 3.2 | 11.4 | 5.6 | 5.8 | 1.3 | 1.2 | 1.2 | 4.0 | 5.0 | 0.9 | 4.0 | 1.1 | 99.6 | 802.7 |
| 35 | 1 | 0.5 | 0.9 | 0.6 | 0.5 | 0.9 | 2.1 | 0.5 | 0.8 | 0.8 | 0.8 | 0.4 | 0.2 | 0.6 | 1.1 | 0.3 | 0.2 | 0.9 | 0.9 | 4.3 | 22.2 |
| 36 | 1 | — | — | — | — | — | 0.2 | — | 0.6 | 0.5 | 0.2 | — | — | — | — | 0.2 | — | — | — | 0.2 | 0.2 |
| 37 | 1 | 6.1 | 1.9 | 3.8 | 1.4 | 1.6 | 6.1 | 1.3 | 4.1 | 6.8 | 5.0 | 0.5 | 2.1 | 5.0 | 1.4 | 7.3 | 0.3 | 3.8 | 1.5 | 10.0 | 185.8 |
| 38 | 1 | — | — | — | — | — | 12.4 | — | 2.0 | 1.1 | 3.9 | — | — | — | — | 1.2 | — | — | — | 11.9 | 230.4 |

TABLE 7-continued

| | | STRAIN | | | | | | | | | | | | | | | | | | | |
|---|---|---|---|---|---|---|---|---|---|---|---|---|---|---|---|---|---|---|---|---|---|
| Co | LAI | A | B | C | D | E | F | G | H | I | J | K | L | M | N | O | P | Q | R | S | T |
| 39 | 1 | — | — | — | — | — | 19.7 | — | 2.3 | 2.4 | 2.2 | — | — | — | — | 1.7 | — | — | — | 16.5 | 249.9 |
| 40 | 1 | — | — | — | — | — | 7.2 | — | 2.1 | 6.4 | 2.7 | — | — | — | — | 3.2 | — | — | — | 12.8 | 87.8 |
| 41 | 1 | — | — | — | — | — | 44.4 | — | 2.3 | 2.5 | 5.6 | — | — | — | — | 2.0 | — | — | — | 37.6 | 252.5 |
| 42 | 1 | 0.9 | 0.4 | 0.9 | 0.5 | 0.3 | 1.2 | 0.7 | 0.9 | 1.9 | 1.6 | 0.5 | 0.6 | 0.7 | 1.0 | 2.1 | 0.2 | 1.1 | 1.0 | 2.4 | 24.5 |
| 43 | 1 | 1.1 | 0.9 | 1.1 | 0.9 | 0.7 | 1.1 | 0.6 | 1.3 | 1.5 | 3.4 | 0.4 | 1.0 | 1.2 | 1.2 | 2.4 | 0.2 | 1.1 | 1.0 | 3.0 | 31.4 |
| 44 | 1 | — | — | — | — | — | 80.2 | — | 29.4 | 7.5 | 29.5 | — | — | — | — | 11.2 | — | — | — | 89.3 | 89.3 |
| 45 | 1 | — | — | — | — | — | 17.3 | — | 1.2 | 4.0 | 1.1 | — | — | — | — | 1.3 | — | — | — | 19.9 | 103.0 |
| 46 | 1 | — | — | — | — | — | 4.7 | — | 1.3 | 3.3 | 2.8 | — | — | — | — | 3.2 | — | — | — | 7.1 | 44.4 |
| 47 | 1 | — | — | — | — | — | — | — | — | — | — | — | — | — | — | — | — | — | — | — | — |
| 48 | 1 | — | — | — | — | — | 9.4 | — | 2.5 | 2.5 | 6.5 | — | — | — | — | 4.3 | — | — | — | 13.8 | 175.0 |
| 49 | 1 | — | — | — | — | — | 12.8 | — | 3.6 | 2.9 | 5.5 | — | — | — | — | 3.9 | — | — | — | 17.8 | 114.0 |
| 50 | 1 | — | — | — | — | — | 8.6 | — | 1.4 | 1.7 | 7.0 | — | — | — | — | 3.5 | — | — | — | 27.9 | 165.5 |
| 51 | 1 | — | — | — | — | — | 2.9 | — | 1.8 | 2.6 | 0.9 | — | — | — | — | 0.6 | — | — | — | 2.1 | 51.8 |
| 52 | 1 | — | — | — | — | — | 10.2 | — | 1.8 | 1.3 | 2.7 | — | — | — | — | 1.6 | — | — | — | 20.3 | 124.5 |
| 53 | 1 | — | — | — | — | — | 2.1 | — | 0.6 | 1.3 | 1.4 | — | — | — | — | 1.6 | — | — | — | 3.8 | 49.8 |
| 54 | 1 | — | — | — | — | — | 3.6 | — | 0.6 | 0.9 | 0.4 | — | — | — | — | 0.4 | — | — | — | 1.8 | 1.4 |
| 55 | 1 | — | — | — | — | — | 26.2 | — | 10.0 | 9.1 | 26.2 | — | — | — | — | 26.2 | — | — | — | 26.2 | 26.2 |
| 56 | 1 | — | — | — | — | — | 33.1 | — | 4.6 | 3.2 | 2.8 | — | — | — | — | 2.1 | — | — | — | 67.1 | 509.6 |
| 57 | 1 | — | — | — | — | — | 1.3 | — | 1.6 | 1.3 | 1.3 | — | — | — | — | 1.3 | — | — | — | 1.6 | 9.0 |
| 58 | 1 | — | — | — | — | — | 2.1 | — | 1.6 | 0.7 | 2.0 | — | — | — | — | 1.7 | — | — | — | 4.4 | 27.0 |
| 59 | 1 | — | — | — | — | — | 2.3 | — | 1.2 | 1.2 | 1.7 | — | — | — | — | 2.0 | — | — | — | 4.7 | 22.2 |
| 60 | 1 | — | — | — | — | — | 1.2 | — | 1.3 | 1.3 | 0.6 | — | — | — | — | 1.1 | — | — | — | 1.4 | 4.1 |
| 61 | 1 | — | — | — | — | — | 32.7 | — | 5.2 | 4.8 | 10.6 | — | — | — | — | 7.1 | — | — | — | 80.0 | 1090.0 |
| 62 | 1 | — | — | — | — | — | 14.5 | — | 3.2 | 2.8 | 2.4 | — | — | — | — | 2.7 | — | — | — | 16.1 | 277.9 |
| 63 | 1 | — | — | — | — | — | — | — | — | — | — | — | — | — | — | — | — | — | — | — | — |
| 64 | 1 | 0.7 | 0.7 | 0.6 | 0.6 | 0.7 | 4.6 | 0.6 | 0.9 | 1.3 | 1.0 | 0.7 | 0.2 | 0.7 | 0.9 | 0.8 | 0.2 | 2.3 | 0.6 | 17.0 | 165.5 |
| 66 | 1 | — | — | — | — | — | 4.0 | — | 0.9 | 1.0 | 1.2 | — | — | — | — | 1.0 | — | — | — | 5.6 | 87.9 |
| 68 | 1 | — | — | — | — | — | 65.2 | — | 7.3 | 2.4 | 3.9 | — | — | — | — | 3.5 | — | — | — | 180.7 | 775.2 |
| 69 | 1 | — | — | — | — | — | — | — | — | — | — | — | — | — | — | — | — | — | — | — | — |
| 70 | 1 | — | — | — | — | — | 4.7 | — | 3.1 | 3.7 | 3.3 | — | — | — | — | 3.2 | — | — | — | 10.4 | 145.1 |
| 71 | 1 | — | — | — | — | — | 29.6 | — | 2.7 | 2.2 | 7.0 | — | — | — | — | 5.0 | — | — | — | 79.6 | 321.5 |
| 72 | 1 | — | — | — | — | — | 67.0 | — | 24.9 | 26.2 | 11.4 | — | — | — | — | 24.4 | — | — | — | 118.0 | 641.1 |
| 73 | 1 | — | — | — | — | — | 43.1 | — | 9.8 | 12.1 | 14.1 | — | — | — | — | 20.7 | — | — | — | 966.6 | 966.6 |
| 74 | 1 | — | — | — | — | — | — | — | — | — | — | — | — | — | — | — | — | — | — | — | — |
| 75 | 1 | — | — | — | — | — | 16.3 | — | 3.6 | 7.4 | 19.4 | — | — | — | — | 18.7 | — | — | — | 19.0 | 93.6 |
| 76 | 1 | — | — | — | — | — | — | — | — | — | — | — | — | — | — | — | — | — | — | — | — |
| 77 | 1 | — | — | — | — | — | 8.9 | — | 2.2 | 8.3 | 11.0 | — | — | — | — | 11.7 | — | — | — | 11.6 | 144.7 |
| 78 | 1 | — | — | — | — | — | 4.8 | — | 2.6 | 3.9 | 2.9 | — | — | — | — | 8.9 | — | — | — | 12.1 | 60.5 |
| 79 | 1 | — | — | — | — | — | 113.0 | — | 12.1 | 3.9 | 9.8 | — | — | — | — | 7.4 | — | — | — | 313.0 | 893.1 |
| 80 | 1 | — | — | — | — | — | 17.4 | — | 5.7 | 3.9 | 17.6 | — | — | — | — | 8.1 | — | — | — | 26.6 | 457.6 |
| 81 | 1 | — | — | — | — | — | 106.8 | — | 5.6 | 6.1 | 29.6 | — | — | — | — | 20.4 | — | — | — | 121.0 | 387.6 |
| 82 | 1 | — | — | — | — | — | 13.8 | — | 5.0 | 4.4 | 5.5 | — | — | — | — | 8.0 | — | — | — | 17.9 | 214.1 |
| 83 | 1 | — | — | — | — | — | 106.6 | — | 4.6 | 7.4 | 8.4 | — | — | — | — | 1.5 | — | — | — | 132.1 | 438.6 |
| 84 | 1 | — | — | — | — | — | 54.3 | — | 11.7 | 13.0 | 19.6 | — | — | — | — | 6.1 | — | — | — | 195.4 | 195.4 |
| 88 | 1 | | | | | | 8.7 | | | | | | | | | | | | | | 26.3 | |
| 89 | 1 | | | | | | 21.9 | | | | | | | | | | | | | | 64.6 | |
| 90 | 1 | | | | | | 28.8 | | | | | | | | | | | | | | 128.8 | |
| 91 | 1 | | | | | | 64.6 | | | | | | | | | | | | | | 323.6 | |
| 92 | 1 | | | | | | 31.6 | | | | | | | | | | | | | | 104.7 | |
| 93 | 1 | | | | | | 1.1 | | | | | | | | | | | | | | 4.68 | |

| Strain | Resistance associated mutations |
|---|---|
| A | L10I, K20R, M36I, I54V, A71V, V82T, I84V |
| B | L10I, K20R, L24I, M36I, I54V, L63P, A71V, V82T, I84V |
| C | L10I, K20R, M36I, M46I, I54V, L63P, A71V, V82T, L90M |
| D | L10I, M36I, I54V, L63P, A71V, G73S, I84V, L90M |
| E | L10I, K20R, L24I, M36I, M46I, I54V, L63P, A71V, G73S, V82T, I84V, L90M |
| F | L10I, M46I, L63P, A71V, I84V |
| G | L10I, L24I, M36V, M46I, I54V, L63P, A71V, V82T, I84V |
| H | L10I, K20R, M36I, L63P, A71V, G73S, V77I, I84V, L90M |
| I | L10I, K20M, I54V, L63P, A71V, I84V, L90M |
| J | L10I, M36I, M46I, L63P, A71V, V77I, I84V, N88D, L90M |
| K | L10I, M36I, I54V, L63P, A71V, V82T, L90M |
| L | L10I, L24I, G48V, I54V, V77I, V82T, L90M |
| M | L10I, L24I, M36I, I54V, L63P, V82T, L90M |
| N | L10I, M46I, I54V, L63P, A71V, V82A, L90M |
| O | L10I, L24I, M36I, I54V, L63P, A71V, I84V |
| P | L10I, D30N, L63P, V77I, N88D |
| Q | L10I, K20R, I54L, L63P, A71V, G73S, L90M |
| R | L10I, M46I, I54V, L63P, A71T, V77I, V82A, L90M |
| S | L10F, M46I, L63P, A71V, I84V |
| T | V32I, M36I, M46I, I47V, I50V, L63P, L90M |
| U | L10F, M46I, I47V, L63P, A71V, I84V |

Biovailability:

The bioavailability of the present compounds was measured in rats. The compounds were administered orally or intra peritoneal. Animals were sacrificed at different time points after administration, whole blood was collected and serum prepared by standard methods. Concentration of the compound in serum was determined by titrating the anti-HIV activity present in the sample according to the procedure described above. Serum concentrations were also measured by HPLC-MS.

Protein Binding Analyses:

Human serum proteins like albumin (HSA) or alpha-1 acid glycoprotein (AAG) are known to bind many drugs, resulting in a possible decrease in the effectiveness of those compounds. In order to determine whether the present compounds would be adversely effected by this binding, the anti-HIV activity of the compounds was measured in the presence of human serum, thus evaluating the effect of the binding of the protease inhibitors to those proteins.

Pharmacokinetic Data

The pharmacokinetic properties of compounds 20, 88 and 90 were tested on rats and dogs. The compounds were evaluated in Whistar rats, source Iffa Credo, weighing approximately 350 g. Before dosing the animals were fasted overnight (approximately 12 h fasting period). The compounds were dissolved in DMSO. The results represented in the table concern the results from the oral dosing of the compounds. Blood was sampled at 30 min, 1 h, 2 h, 3 h, no pre-dose sample was taken. The amount of the compound in the biological sample was determined using LC-MS. In the table below "or" means oral dosing, "mpk" means mg per kilogram.

The results are illustrated in Table 8.

TABLE 8

| Compound | $C_{max}$ (ng/ml) (or, rat, 10 mpk, DMSO) | $C_{3hours}$ (ng/ml) (or, rat, 10 mpk, DMSO) | $C_{max}$ (ng/ml) (or, dog, 10 mpk, DMSO) |
|---|---|---|---|
| 20 | 1425 | 401 | 713 |
| 88 | 254 | 225 | 379 (PEG) |
| 90 | 893 | 684 | 550 |

A high plasma level can be observed for these compounds and more specifically for the compound such as compound 20, which is due to the good solubility of said compounds in water.

The invention claimed is:

1. A compound chosen from the group consisting of

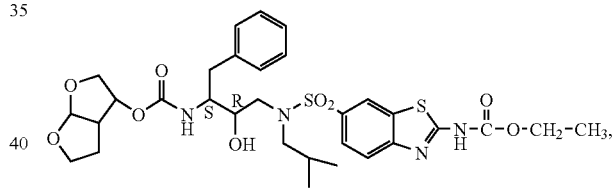

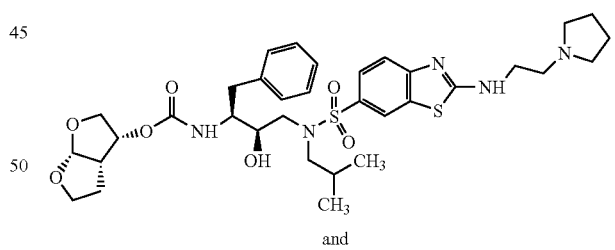

and

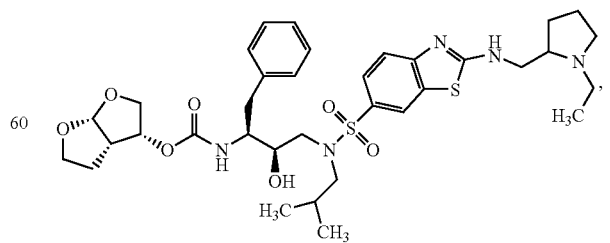

and the pharmaceutically acceptable salt forms thereof.

2. A compound according to claim 1, wherein said compound is
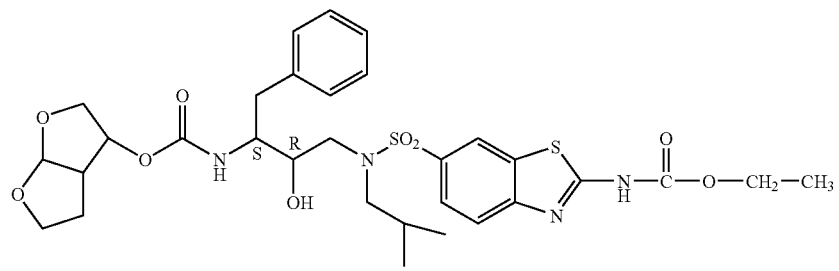
(6-{[3-(Hexahydro-furo[2,3-h]furan-3-yloxycarbony-lamino)-2-hydroxy-4-phenyl-butyl]-isobutyl-sulfamoyl}-benzothiazol-2-yl)-carbamic acid ethyl ester.
* * * * *

UNITED STATES PATENT AND TRADEMARK OFFICE
CERTIFICATE OF CORRECTION

PATENT NO. : 7,659,404 B2  
APPLICATION NO. : 10/467609  
DATED : February 9, 2010  
INVENTOR(S) : Surleraux et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (401) days Delete the phrase "by 401 days" and insert -- by 737 days --

Signed and Sealed this

Twenty-fourth Day of August, 2010

David J. Kappos  
*Director of the United States Patent and Trademark Office*